(12) United States Patent
Arnould et al.

(10) Patent No.: US 7,842,489 B2
(45) Date of Patent: Nov. 30, 2010

(54) USE OF MEGANUCLEASES FOR INDUCING HOMOLOGOUS RECOMBINATION EX VIVO AND IN TOTO IN VERTEBRATE SOMATIC TISSUES AND APPLICATION THEREOF

(75) Inventors: Sylvain Arnould, Paris (FR); Sylvia Bruneau, Paris (FR); Jean-Pierre Cabaniols, Saint Leu la Foret (FR); Patrick Chames, Paris (FR); Andre Choulika, Paris (FR); Philippe Duchateau, Cerny (FR); Jean-Charles Epinat, Paris (FR); Agnes Gouble, Paris (FR); Emmanuel Lacroix, Paris (FR); Frederic Paques, Bourg la Reine (FR); Christophe Perez-Michaut, Paris (FR); Julianne Smith, Paris (FR); David Sourdive, Levallois-Perret (FR)

(73) Assignee: Cellectis, Romainville (FR)

( * ) Notice: Subject to any disclaimer, the term of this patent is extended or adjusted under 35 U.S.C. 154(b) by 0 days.

(21) Appl. No.: 12/710,969

(22) Filed: Feb. 23, 2010

(65) Prior Publication Data

US 2010/0144012 A1    Jun. 10, 2010

Related U.S. Application Data

(63) Continuation of application No. 10/543,557, filed as application No. PCT/IB2004/000848 on Jan. 28, 2004.

(60) Provisional application No. 60/442,911, filed on Jan. 28, 2003, provisional application No. 60/491,535, filed on Aug. 1, 2003.

(51) Int. Cl.
*C12N 9/22* (2006.01)
*C12N 15/55* (2006.01)

(52) U.S. Cl. ............... 435/199; 435/196; 435/183; 435/69.7; 530/350

(58) Field of Classification Search .............. None
See application file for complete search history.

(56) References Cited

U.S. PATENT DOCUMENTS

| | | | |
|---|---|---|---|
| 4,179,337 A | 12/1979 | Davies et al. | |
| 5,006,333 A | 4/1991 | Saifer et al. | |
| 5,272,071 A | 12/1993 | Chappel | |
| 5,436,150 A | 7/1995 | Chandrasegaran | |
| 5,474,896 A | 12/1995 | Dujon et al. | |
| 5,641,670 A | 6/1997 | Treco et al. | |
| 5,792,632 A | 8/1998 | Dujon et al. | |
| 5,801,030 A | 9/1998 | McVey et al. | |
| 5,830,729 A | 11/1998 | Jaisser et al. | |
| 5,843,701 A | 12/1998 | Gold et al. | |
| 5,866,361 A | 2/1999 | Dujon et al. | |
| 5,948,678 A | 9/1999 | Dujon et al. | |
| 5,962,327 A | 10/1999 | Dujon et al. | |
| 6,037,162 A | 3/2000 | Raveh et al. | |
| 6,063,630 A | 5/2000 | Treco et al. | |
| 6,232,112 B1 | 5/2001 | Catcheside | |
| 6,238,924 B1 | 5/2001 | Dujon et al. | |
| 6,395,959 B1 | 5/2002 | Dujon et al. | |
| 6,528,313 B1 | 3/2003 | Le Mouellic et al. | |
| 6,528,314 B1 | 3/2003 | Le Mouellic et al. | |
| 6,610,545 B2 | 8/2003 | Dujon et al. | |
| 7,309,605 B1 | 12/2007 | Dujon et al. | |
| 7,462,758 B2 | 12/2008 | Biesgen et al. | |
| 2003/0096249 A1 | 5/2003 | Westphal et al. | |
| 2003/0228583 A1 | 12/2003 | Amacher et al. | |
| 2004/0002092 A1 | 1/2004 | Arnould et al. | |
| 2005/0064474 A1 | 3/2005 | Urnov et al. | |
| 2005/0172365 A1 | 8/2005 | Puchta et al. | |
| 2006/0206949 A1 | 9/2006 | Arnould et al. | |

FOREIGN PATENT DOCUMENTS

| | | |
|---|---|---|
| EP | 419 621 | 12/1995 |
| WO | WO 91/17271 | 11/1991 |
| WO | WO 91/18980 | 12/1991 |
| WO | WO 91/19818 | 12/1991 |
| WO | WO 93/08278 | 4/1993 |
| WO | WO 94/18313 | 8/1994 |
| WO | WO 95/09233 | 4/1995 |
| WO | WO 96/14408 | 5/1996 |
| WO | WO 00/46385 | 8/2000 |
| WO | WO 00/46386 | 8/2000 |
| WO | WO 00/47775 | 8/2000 |

(Continued)

OTHER PUBLICATIONS

Ngo et al. in The Protein Folding Problem and Tertiary Structure Prediction, 1994, Merz et al. (ed.), Birkhauser, Boston, MA, pp. 433 and 492-495.*

(Continued)

*Primary Examiner*—Richard G Hutson
(74) *Attorney, Agent, or Firm*—Kenyon & Kenyon LLP

(57) ABSTRACT

A single chain homing endonuclease, comprising a first variant of I-CreI having the amino acid sequence of accession number pdb 1g9y (SEQ ID NO: 23 is residues 1-153 of pdb Ig9y) and a second variant of I-CreI variant having the amino acid sequence of accession number pdb 1g9y (SEQ ID NO: 23 is residues 1-153 of pdb Ig9y) in a single polypeptide.

7 Claims, 22 Drawing Sheets

FOREIGN PATENT DOCUMENTS

| WO | WO 01/70946 | 9/2001 |
|---|---|---|
| WO | WO 02/42497 | 5/2002 |
| WO | 02/099105 A2 | 12/2002 |
| WO | 03/078619 A1 | 9/2003 |
| WO | WO 2004/067736 | 8/2004 |

OTHER PUBLICATIONS

Epinat, et al., "A novel engineered meganuclease induces homologous recombination in yeast and mammalian cells", Nucleic Acids Research, vol. 31, No. 11, pp. 2952-2962, 2003.

Seligman, et al., "Mutations altering the cleavage specificity of an homing endonuclease", Nucleic Acids Research, vol. 30, No. 17, pp. 3870-3879, 2002.

Seligman, et al., "Genetic Analysis of the Chlamydomonas reinhardtii I-CreI Mobile Intron Homing System in *Escherichia coli*", Genetics, vol. 147, pp. 1653-1664, 1997.

Jurica, et al., "DNA Recognition and Cleavage by the LAGLIDADG Homing Endonuclease I-CreI" Molecular Cell, vol. 2, pp. 469-476, Oct. 1998.

Lucas, et al., "Rapid evolution of the DNA-binding site in LAGLIDADG Homing Endonucleases", Nucleic Acids Research, vol. 29, No. 4, pp. 960-969, 2001.

Chevalier, et al., "Design, Activity, and Structure of a Highly Specific Artificial Endonuclease", Molecular Cell, vol. 10, pp. 895-905, Oct. 2002.

Aiuti et al., "Correction of ADA-SCID by Stem Cell Gene Therapy Combined with Nonmyeloablative Conditioning," Science, 196: 2410-2413 (2002).

Aiuti et al., "Gene Therapy for Immunodeficiency Due to Adenosine Deaminase Deficiency," The New England Journal of Medicine, vol. 360, No. 5, 447-458 (2009).

Biet et al., Homologous Recombination and Gene Targeting (in French with English abstract), Compes Renducs-Biologics, 326(1): 51-64 (2003).

Cavazzana-Calvo et al., "Gene Therapy of Human Sever Combined Imminodificiency (SCID)-X1 Disease," Science, 288: 669-672 (2000).

Delacote et al., "Importance of the cell cycle Pphase for the choice of the appropriate DSB repair pathway, for genome stability maintenance", Cell Cycle, 7:1, 33-38 (2008).

Feigin et al., "Modulation of Metabolic Brain Networks After Subthalamic Gene Therapy for Parkinson's Disease," PNAS, 104: 1959-19564 (2007).

Fischer et al., "LM02 and Gene Therapy for Severe Combined Immunodificiency," The New England Journal of Medicine, 2526-2527 (2004).

Gaspar et al., "Gene Therapy of X-Linked Severe Combined Immunodeficiency by Use of a Pseudotyped Gammaretroviral Vector," Lancet, 364: 2181-2187 (2004).

Guo et al., Group II Introns Designed to Insert into Therapeutically Relevant DNA Target Sites in Human Cells, 289: 452-457 (2000).

Hacein-Bey-Abina et al., "LMO2-Associated Clonal T Cell Proliferation in Two Patients after Gene Therapy for SCID-X1," Science, 415-419 (2003).

Harding et al., "Intravenous Administration of an AAV-2 vector for the expression of factor IX in mice and a dog model of hemophilia B", Gene Therapy, 11:204-213 (2004).

Jasin, "Genetic Manipulation of genomes with Rare-Cutting Endonucleases," Trends in Genetics, vol. 12, No. 6, 224-228 (1996).

Kaplitt et al., "Safety and Tolerability of Gene Therapy with an Adeno-Associated Virus (AAV) Borne GAD Gene for Parkinson's Disease: An Open Label, Phase 1 Trial," Lancet, 369: 2097-2105 (2007).

Kohn et al., "Occurrence of Leukaemia Following Gene Therapy of X-Linked Scid," Nature Reviews-Cancer, (3):477-488 (2003).

Liu et al., "Naked DNA in Gene Therapy," Encyclopedia of Life Science, 1-4 (2005).

Logan et al., "Advances in Lentiviral Vector Design for Gene-Modification of Hematopoietic Stem Cells," Current Opinion in Biotechnology, 13: 429-436 (2002).

Miller et al., "Retroviral Vectors in Gene Therapy", Encyclopedia of Life Science, 1-5 (2005).

Pfeifer et al., "Transduction of Liver Cells by Lentiviral Vectors: Analysis in Living Animals by Fluorescence Imaging", Molecular Therapy, vol. 3, No. 3 (2001).

Philpott et al., "Viral Vectors for Gene Therapy," Encyclopedia of Life Sciences, 1-6 (2007).

Russell, "Replicating Vectors for Gene Therapy of Cancer: Risks, Limitations and prospects," European Journal Cancer, 30A(8): 1165-117.

Sirven et al., "The Human Immunodeficiency Virus Type-1 Central DNA Flap is a Crucial Determinant of Lentiviral Vector Nuclear Import and Gene Transduction of Human Hematopoietc Stem Cells," Blood, vol. 96, No. 13, 4103-4110 (2000).

Thomas et al., "Progress and Problems with the Use of Viral Vectors for Gene Therapy," Nature, vol. 346, No. 4: 335-346 (2003).

Verma et al., "Gene Therapy: Promises, Problems and Prospects," Nature, vol. 389, 239-242 (1997).

Wilson et al., "Good News on the Clinical Gene Transfer Front," Human Gene Therapy, 19: 429-430 (2008).

Zennou et al., "HIV-1 Genome Nuclear Import is Mediated by a Central DNA Flap," Cell, 101: 173-185 (2000).

Zhong et al., "Adeno-Associated viral Vectors in Gene Therapy," Encyclopedia of Life Sciences, 1-8 (2007).

Wilson, "Pointing Fingers at the Limiting Step in Gene Targeting," Nature Biotechnology, 21(7): 759-760 (2003).

International Search Report of PCT/IB2004/000848 dated Jul. 23, 2004.

Arimondo et al., "Directing Topoisomerase I Mediated DNA Cleavage to Specific Sites by Camptothecin Tethered to Minor- and Major-Groove Ligands," Angew Chem Int. Ed Engl, 40:3045-3048 (2001).

Arimondo et al., "Design of New Anti-Cancer Agents Based on Topoisomerase Poisons Targeted to Specific DNA Sequences," Curr Med. Chem Anti-Canc Agents, 1:219-235 (2001).

Bae et al., "Human Zinc Fingers as Building Blocks in the Construction of Artificial Transcription Factors," Nat. Biotechnol, 21: 275-280 (2003).

Bell-Pedersen et al., "A Site-Specific Endonuclease and Co-conversion of Flanking Exons Associated with the Mobile td Intron of Phage T4," Gene, 82:119-126 (1989).

Bell-Pedersen et al., "Intron Mobility in Phage T4 is Dependent Upon a Distinctive Class of Endonucleases and Independent of DNA Sequences Encoding the Intron Core: Mechanistic and Evolutionary Implications," Nucleic Acids Res, 18: 3763-3770 (1990).

Bibikova et al., "Stimulation of Homologous Recombination Through Targeted Cleavage by Chimeric Nucleases," Mol. Cell Biol, 21: 289-297 (2001).

Bibikova et al., "Enhancing Gene Targeting with Designed Zinc Finger Nucleases," Science, 300, 764 (2003).

Bonetta, "Getting Proteins Into Cells: The Discovery and Commercialization of Protein Transduction Domains Frees Researchers from Transfection Troubles," The Scientist, 16: 38-40 (2002).

Buerstedde et al., "Increased Ratio of Targeted to Random Integration after Transfection of Chicken B Cell Lines," Cell, 67: 179-188 (1991).

Chealier et al., "Design, Activity, and Structure of a Highly Specific Artificial Endonuclease," Molecular Cell, 10:895-905 (2002).

Chevalier et al, "Homing Endonucleases: Structural and Functional Insight Into Catalysts of Intron/Intein Mobility," Nucleic Acids Resarch, 29: 3757-3774 (2001).

Chevalier et al, "The Homing Endonuclease I-CreI Uses Three Metals, One of Which is Shared Between the Two Active Sites," Nat Struct Biol, 8:312-316 (2001).

Chiurazzi et al., "Enhancement of Somatic Intrachromosomal Homologous Recombination in Arabidopsis by the HO Endonuclease," Plant Cell, 8:2057-2066 (1996).

Choulika et al., "Induction of Homologous Recombination if Mammalian Chromosomes by Using the I-SceI System of *Saccharomyces cerevisiae*," Mol Cell Biol, 15: 1968-1973 (1995).

Cohen-Tannoudji et al., "I-SceI-Induced Gene Replacement at Natural Locus in Embryonic Stem Cells," Mol Cell Biol, 18: 1444-1448 (1998).

Colleaux et al., "Recognition and Cleavage Site of the Intron-encoded Omega Transposase," PNAS, 85:6022-6026 (1998).
Doetschman et al., "Targeted Mutation of the Hprt Gene in Mouse Embryonic Stem Cells," PNAS, 85: 8583-8587 (1988).
Donoho et al., "Analysis of Gene Targeting and Intrachromosomal Homologous Recombination Stimulated by Genomic Double-Strand Breaks in Mouse Embryonic Stem Cells," Mol Cell Biol, 18: 4070-4078 (1998).
Duan et al., "Crystal Structure of PI-SceI, a Homing Endonuclease with Protein Splicing Activity," Cell, 89: 555-564 (1997).
Eisenschmidt et al., "A Fluorimetric Assay for On-line Detection of DNA Cleavage by Restriction Endonucleases," Journal of Biotechnology, 96: 185-191 (2002).
Essers et al., "Disruption of Mouse RAD54 Reduces Ionizing Radiation Resistance and Homologous Recombination," Cell, 89: 195-204 (1997).
Fairhead et al., "Consequences of Unique Double-Stranded Breaks in Yeast Chromosomes: Death or Homozygosis," Mol Gen Genet, 240:170-188 (1993).
Fischer et al., "Gene Therapy for Human Severe Combined Immunodeficiencies," Isr. Med. Assoc J. 4:51-54 (2002).
Fishman-Lobell et al., "Removal of Nonhomologous DNA Ends in Double-Strand Break Recombination: The Role of the Yeast Ultraviolet Repair Gene RAD 1," Science, 258: 480-484 (1992).
Ford et al., "Protein Transduction: An Alternative to Genetic Intervention?" Gene Ther, 8: 1-4 (2001).
Gasior et al., "Assembly of RecA-like Recombinases: Distinct Roles for Mediator Proteins in Mitosis and Meiosis," PNAS, 98: 8411-8418 (2001).
Goncz et al., "Application of SHFR to Gene Therapy of Monogenic Disorders," Gene Therapy, 9: 691-69 (2002).
Gorman et al., "Directed Gene Modification via Triple Helix Formation," Curr Mol. Med, 1: 391-399 (2001).
Haber, "Mating-Type Gene Switching in *Saccharomyces cerevisiae*," Annu Rev Genet, 32: 561-599 (1998).
Haber, "In Vivo Biochemistry: Physical Monitoring of Recombination Induced by Site-specific Endonucleases," Bioessays, 17: 609-620 (1995).
Hanes et al., "In Vitro Selection and Evolution of Functional Proteins by Using Ribosome Display," PNAS, 94: 4937-4942 (1997).
He et al., "Antibody-ribosome-mRNA (ARM) Complexes as Efficient Selection Particles for In Vitro Display and Evolution of Antibody Combining Sites," Nucl. Acids Res, 25: 5132-5143 (1997).
Heath et al., "The Structure of I-CreI, a Group I Intron-encoded Homing Endonuclease," Nat. Struct Biol, 4: 468-476 (1997).
Henry I et al., "Lago Z and LagZ, Two Genes Derived from the LacZ Gene to Study Epigenetics," C R Acad Sci III, 322, 1061-1070 (1999).
Hu et al., "Probing the Structure of the PI-SceI-DNA Complex by Affinity Cleavage and Affinity Photocross-linking," J Biol Chem, 275: 2705-2712 (2000).
Ichiyanagi et al., "Crystal Structure of an Archaeal Intein-encoded Homing Enconuclease PI-Pful," J Mol Biol, 300: 889-901 (2000).
Isalan et al., "Engineering Nucleic Acid-Binding Proteins by Phage Display," Methods Mol Biol, 148: 417-429 (2001).
Isalan et al., "A Rapid, Generally Applicable Method to Engineer Zinc Fingers Illustrated by Targeting the HIV-1 Promoter," Nat. Biotechnol, 19: 656-660 (2001).
Isalan et al., "Rapid, High-Throughput Engineering of Sequence-Specific Zinc Finger DNA-Binding Proteins," Methods Enzymol, 340: 593-609 (2001).
Jacquier et al., "An Intron-Encoded Protein Is Active in a Gene Conversion Process That Spread an Intron into a Mitochondrial Gene," Cell, 41: 383-394 (1985).
Kadyk et al., "Sister Chromatids Are Preferred Over Homologs as Substrates for Recombinational Repair in *Saccharomyces cerevisiae*," Genetics, 132:387-402 (1992).
Karberg et al., "Group II Introns as Controllable Gene Targeting Vectors for Genetic Manipulation of Bacteria," Nat. Biotechnol, 19: 1162-1167 (2001).
Kim et al., "Hybrid Restriction Enzymes: Zinc Finger Fusions to Fok I Cleavage Domain," PNAS, 93:1156-1160 (1996).
Kim et al., "Chimeric Restriciton Endonuclease," PNAS, 91: 883-887 (1994).
Kim, et al., "Use of the Human Elongation Factor 1α Promoter as a Versatile and Efficient Expression System," Gene, 91:217-223 (1990).
Lanio et al., "On the Possibility and Limitation of Rational Protein Design to Expand the Specificity of Restriction Enzyme: A Case Study Employing EcoRV as the Target," Protein Eng., 13: 275-281 (2000).
Liang et al., "Homology-directed Repair is a Major Double-Strand Break Repair Pathway in Mammalian Cells," PNAS, 95: 5172-5177 (1998).
Lin et al., "Capture of DNA Sequences at Double-Strand Breaks in Mammalian Chromosomes," Genetics, 158:1665-1674 (2001).
Liu et al., "Dydrodynamics-based Transfection in Animals by Systemic Administration of Plasmid DNA," Gene Therapy, 6: 1258-1266 (1999).
Miller et al., "Human Gene Targeting by Adeno-Associated Virus Vectors Is Enhanced by DNA Double-Strand Breaks," Mol Cell Biol, 23: 3550-3557 (2003).
Moore et al., "Design of Polyzin Finger Peptides with Structured Linkers," PNAS, 98: 1432-1436 (2001).
Moore et al., "Improved DNA Binding Specificity from Polyzinc Finger Peptides by Using Strings of Two-finger Units," PNAS, 98: 1437-1441 (2001).
Mueller et al., "Exon Conconversion Biases Accompanying Intron Homing: Battle of the Nucleases," Genes Dev, 10: 2158-2166 (1996).
Murphy, "Use of Bacteriophage λ Recombination Functions to Promote Gene Replacement in *Escherichia coli*," J. Bacteriol, 180:2063-2071(1998).
Papworth et al., "Inhibition of Herpes Simplex Virus 1 Gene Expression by Designer Zinc-finger Transcription Factors," PNAS, 100:1621-1626 (2003).
Paques et al., "Multiple Pathways of Recombination Induced by Double-Strand Breaks in *Saccharomyces cerevisiae*," Microbial Mol Biol Rev, 63: 349-404 (1999).
Paques et al., "Two Pathways for Removal of Nonhomologous DNA Ends During Double-Strand Break Repair in *Saccharomyces cerevisiae*," Mol. Cell. Boil, 17: 6765-6771 (1997).
Perrin et al., "Asymmetrical Recognition and Activity of the I-SceI Endonuclease on its Site and on Intron-exon Junctions," Embo J, 12: 2939-2947 (1993).
Plessis et al., "Site-Specific Recombination Determine by I-SceI, a Mitochondrial Group I Intron-Encoded Endonuclease Expressed in the Yeast Nucleus," Genetics, 130:451-460 (1992).
Poland et al., "Structural Insights into the Protein Splicing Mechanism of PI-SCeI," J Biol Chem, 275: 16408-16413 (2000).
Porteus et al., "Chimeric Nucleases Stimulate Gene Targeting in Human Cells," Science, 300, 763 (2003).
Porteus et al., "Efficient Gene Targeting Mediated by Adeno-Assocaited Virus and DNA Double-Strand Breaks," Mol Cell biol, 23: 3558-3565 (2003).
Posfai et al., "Markerless Gene Replacement in *Escherichia coli* Stimulated by a Double-strand Break in the Chromosome," N.A.R., 27:4409-4415 (1999).
Puchta et al., "Two Different but Related Mechanisms are Used in Plants for the Repair o Genomic Double-strand Breaks by Homologous Recombination," PNAS, 93:5055-5060 (1996).
Puchta, "Double-Strand Break-Induced Recombination Between Ectopic Homologous Sequences in Somatic Plant Cells," Genetics, 152:1173-1181 (1999).
Puchta et al., "Homologous Recombination in Plant Cells is Enhanced by in vivo Induction of Double Strand Breaks into DNA by a Site-specific Endonuclease," Nucleic Acids Res, 21: 5034-5040 (1993).
Reynolds et al., "Represion of the HIV-1 5' LTR Promoter and Inhibition of HIV-1 Replication by Using Engineered Zinc-finger Transcription Factors," PNAS, 100:1615-1620 (2003).
Rong et al., "Targeted Mutagenesis by Homologous Recombination I D. Melanogaster," Genes Dev, 16:1568-1581 (2002).
Rouet et al., "Introduction of Double-Strand Breaks into the Genome of Mouse Cells by Expression of a Rare-Cutting Endonuclease," Mol Cell Biol, 14: 8096-8106 (1994).

Rudin et al., "Genetic and Physical Analysis of Double-Stranded Break Repair and Recombination in *Saccharomyces cerevisiae*," Genetics, 122: 519-534 (1989).

Schaefer et al., "Efficient Gene Targeting in the Moss Physcomitrella Patens," Plant J, 11(6): 1195-1206 (1997).

Siebert et al., "Efficient Repair of Genomic Double-Strand Breaks by Homologous Recombination Between Directly Repeated Sequences in the Plant Genome," The Plant Cell, 14: 1121-1131 (2002).

Silva et al., "Crystal Structure of the Thermostable Archael Intron-encoded Endonuclease I-Dmol," J Mol Biol, 286:1123-1136 (1999).

Smith et al., "Requirements for Double-Strand Cleavage by Chimeric Restriction Enzymes with Zinc Finger DNA-recognition Domains," Nucleic Acid Research, 28:3361-3369 (2000).

Smith et al., "A Detailed Study of the Substrate Specificity of a Chimeric Restriction Enzyme," Nucleic Acids Research, 27: 674-681 (1999).

Tabuchi et al., "An In Vitro DNA Virus for In Vitro Evolution," FEBS Letters, 508: 309-312 (2001).

Thomas et al., "Introduction of Homologous DNA Sequences into Mammalian Cells Induces Mutations in the Cognate Gene," Nature, 324: 34-38 (1986).

Thomas et al., "High Frequency Targeting of Genes to Specific Sites in the Mammalian Genome," Cell, 44: 419-428 (1986).

Thomas et al., "Targeting of Genes to Specific Sites in the Mammalian Genome," Cold Spring Harb Symp Quant Biol, 51:1101-1113 (1986).

Takata et al., "Homologous Recombination and Non-homologous End-joining Pathways of DNA Double-Strand Break Repair Have Overlapping Roles in the Maintenance of Chromosomal Integrity in Vertebrate Cells," Embo J. 17: 5497-5508 (1998).

Joung et al., "A Bacterial Two-hybrid Selection System for Studying Protein-DNA and Protein-protein Interactions," PNAS, 97:7382-7387 (2000).

Yoon et al., "Targeted Gene Correction of Episomal DNA in Mammalian Cells Mediated by a Chimeric RNA-DNA Oligonucleotide," PNAS, 93: 2071-2076 (1996).

Wadia et al., "Protein Transduction Technology," Curr Opin Biotechnol, 13: 52-56 (2002).

Zhang et al., "A New Logic for DNA Engineering Using Recombination in *Escherichia coli*," Nat. Genet, 20: 123-128 (1998).

Zhang et al., "High Levels of Foreign Gene Expression in Hepatocytes after Tail Vein Injections of Naked Plasmid DNA," Human Gene Therapy, 10:1735-1737 (1999).

Arnould et al., "Engineering of Large Numbers of Highly Specific Homing Endonucleases that Induce Recombination on Novel DNA Targets," J. Mol. Biol, 355: 443-458 (2006).

Cabaniols et al., "Robust Cell Lin Development Using Meganucleases," Methods in Molecular Biology, vol. 435: 31-45.

Chames et al., "In Vivo Selection of Engineered Homing Endonucleases using Double-Strand Break Induced Homologous Recombination," Nucleic Acids Res., 33: e178 (2005).

Chevalier et al., "Design, Activity, and Structure of a Highly Specific Artificial Endonuclease," Molecular Cell, 10: 895-905 (2002).

Choulika et al., "The Yeast I-Sce I Meganuclease Induces Site-Directed Chromosomal Recombination in Mammalian Cells," C R Acad Sci III,1994 317:1013-9 (1994).

Colleaux et al., "Universal Code Equivalent of a Yeast Mitochondrial Intron Reading Frame Is Expressed into *E. coli* as a Specific Double Strand Endonuclease," Cell, 44:521-533 (1986).

Delahodde et al., "Site-Specific DNA Endonuclease and RNA Mautrase Activities of Two Homologous Intron-Encoded Proteins from Yeast Mitochondria," Cell, 56: 431-441 (1989).

Dujon et al., "Group I Introns as Mobile Genetic Elements: Facts and Mechanistic Speculations—a Review," Gene, 82: 91-126 (1989).

Dujon et al., "Cellectis. Celletis' 5th Scientific Advisory Board Meeting. Report of the Meeting," p. 1-4, Dec. 16 and 17, 2004.

Dujon et al., "Homing Endonucleases and the Yeast Mitochondrial Locus—A Historical Perspective," Nucleic Acids and Molecular Biology, 16: 11-31 (2005).

Durrenberger et al., "Chloroplast Ribosomal Intron of Chlamydomonas Reinhardtil: In Vitro Self-Splicing, DNA Endonuclease Activity and In Vivo Mobility," the EMBO J, 10:3495-3501 (1991).

Epinat et al., "A Novel Engineered Meganuclease Induces Homologous Recombination in Yeast and Mammalian Cells", Nucleic Acids Research, 31: 2952-2962 (2003).

Galetto et al., "Target Approaches for Gene Therapy and the Emergence of Engineered Meganucleases," Expert Opin. Biol. Ther, 9:1289-1303 (2009).

Lacroix et al., "Automated Discovery and Design of Novel Meganucleases," Cellectis S.A., 1-21.

Maggos, "Technology, Industrializing DNA Modification," BioCentury, Cellectis091508, PREC197169 (Jan. 22, 2007).

Marcaida et al., "Crystal Structure of I-Dmol in Complex with its Target DNA Provides New Insights into Meganuclease Engineering," PNAS, 105: 16888-16893 (2008).

Meganuclease I-Sce I (Omega-Nuclease), Cat No. 11 362 399 001, Version Nov. 2004. Roche.

Paques et al., "Meganucleases and DNA Double-Strand Break-Induced Recombination: Perspectives for Gene Therapy," Current Gene Therapy, 7: 49-66 (2007).

Plaintiff Cellectis's Brief in Support of its Proposed Claim Construction, Nov. 2, 2009.

Prieto et al., "Generation and Analysis of Mesophilic Variants of the Thermostable Archael I-DMOI Homing Endonuclease," J. Biol. Chem., 283: 4364-4374 (2008).

Quirk et al., "Intron Mobility in the T-Even Phages: Hight Frequency Inheritance of Group I Introns Promoted by Intron Open Reading Frames," Cell, 56: 455-465 (1989).

Redondo et al., "Molecular Basis of Xeroderma Pigmentosum Group C DNA Recognition by Engineered Meganucleases," Nature, 456: 107- (2008).

Schiestl et al., "Integration of DNA Fragments by Illegitimate Recombination in *Saccharonmyces cerevisiae*," Proc. Natl. Acad. Sci., 88: 7585-7589 (1991).

Seligman et al., "Mutations Altering the Cleavage Specificity of a Homing Endonuclease," Nucleic Acids Research, 30: 3870-3879 (2002).

Smith et al., "A Combinatorial Approach to Create Artificial Homing Endonucleases Cleaving Chosen Sequences," Nucleic Acids Research, 34: e149 (2006).

Stoddard, Expert Report of Bary L. Stoddard, Ph.D. on the Meaning of the Asserted Claims in Cellectis's Patents, Jan. 16, 2009.

Thierry et al., "Cleavage of Yeast and Bacteriophage T7 Genomes at a Single Site Using the Rare Cutter Endonuclease I-Sce I," Nucleic Acids Research, 19:189-190 (1991).

Watson et al., p. 41-Recombinant DNA, 1983.

Coffin, "Chapter 26, Retroviridae: The Viruses and their Replication," Fundamental Virology, 3rd ed., B.N. Fields, Lippincott-Raven Publishers, Philadelphia, 1996.

Interlocutory Decision in Opposition Proceedings issued for EP 03744485.8-2405, Feb. 8, 2010.

Ausubel et al., "Chapter 8, Mutagenesis in Cloned DNA", Current Protocol in Molecular Biology, John Wiley and Sons.

Haines et al., Table of Content, Current Protocol in Human Genetics, John Wiley and Sons.

Hess et al., Table of Content, Pharmaceutical Dosage Forms and Their Use, 1985.

Rowe et al., Table of Content, , The Handbook of Pharmaceutical Excipients, 2003.

Office Action from related U.S. Appl. No. 10/543,556, mailed May 14, 2009, and Aug. 19, 2008.

Office Action from related U.S. Appl. No. 11/908,934, mailed Oct. 14, 2010, and Jan. 25, 2010.

Office Action from related U.S. Appl. No. 10/388,230, mailed May 24, 2010, Nov. 25, 2008, Jun. 14, 2007, and Feb. 9, 2006.

Office Action from related U.S. Appl. No. 10/507,736, mailed Jun. 25, 2010, Aug. 5, 2009, and Aug. 1, 2008.

Office Action from related U.S. Appl. No. 11/908,798, mailed Sep. 2, 2010.

Notice of Opposition to a European Patent No. 1 485 475, dated Jun. 5, 2008.

Summons to Attend Oral Proceedings issued for European Patent No. 1 485475, dated Jun. 30, 2009.

Response to Summons to Attend Oral Proceedings for European Patent No. 1 485475, filed Sep. 18, 2009.

Response to Opposition to European Patent No. 1 485475, filed Jan. 13, 2009.

Response to Oral Proceedings to European Patent No. 1 485475, filed Sep. 18, 2009.

Appeal filed for European Patent No. 1 485475, filed Jun. 8, 2010. (French).

Appeal filed for European Patent No. 1 485475, filed Jun. 17, 2010.

* cited by examiner

Amino acid sequence of a Single chain I-Cre I (SEQ ID NO: 1)

```
  1 MANTKYNKEF LLYLAGFVDG DGSIIAQIKP NQSYKFKHQL SLTFQVTQKT
 51 QRPWFLDKLV DEIGVGYVRD RGSVSDYILS EIKPLHNFLT QLQAMLERIR
101 LFNMREPLLY LAGFVDGDGS IIAQIKPNQS YKFKHQLSLT FQVTQKTQRR
151 WFLDKLVDEI GVGYVRDRGS VSDYILSEIK PLHNFLTQLQ PFLKLKQKQA
201 NLVLKIIEQL PSAKESPDKF LEVCTWVDQI AALNQSKTRK TTSETVRAVL
251 DSLSEKKKSS PAAD
```

Polynucleotide sequence encoding the Single chain I-Cre I (SEQ ID NO: 2)

```
  1 ATGGCCAACA CTAAGTACAA TAAAGAATTT CTCCTGTATC TGGCAGGTTT
 51 CGTCGACGGC GATGGCTCCA TTATCGCACA GATCAAGCCG AATCAGAGCT
101 ACAAGTTTAA ACACCAACTG TCTCTCACTT TCCAGGTTAC CCAGAAAACT
151 CAACGTCGCT GGTTCCTGGA TAAGCTGGTA GATGAGATCG GTGTGGCTA
201 TGTACGCGAC CGTGGCTCTG TGAGCGACTA TATCCTGTCT GAGATTAAAC
251 CACTGCATAA TTTTCTGACC CAGCTGCAGG CTATGCTGGA GCGTATCCGT
301 CTGTTCAACA TGCGTGAGTT CCTGCTGTAC CTGGCCGGCT TTGTGGACGG
351 TGACGGTAGC ATCATCGCTC AGATTAAACC AAACCAGTCT TATAAATTCA
401 AGCATCAGCT GTCCCTGACC TTTCAGGTGA CTCAAAAGAC CCAGCGCCGT
451 TGGTTTCTGG ACAAACTGGT GGATGAAATT GGCGTTGGTT ACGTACGTGA
501 TCGCGGTAGC GTTTCCGATT ACATTCTGAG CGAAATCAAG CCGCTGCACA
551 ACTTCCTGAC TCAACTGCAA CCGTTTCTGA AACTGAAACA GAAACAGGCA
601 AACCTGGTTC TGAAAATTAT CGAACAGCTG CCGTCTGCAA AAGAATCCCC
651 GGACAAATTC CTGGAAGTTT GTACCTGGGT GGATCAGATT GCAGCTCTGA
701 ACGATTCTAA GACGCGTAAA ACCACTTCTG AAACCGTTCG TGCTGTGCTG
751 GACAGCCTGA GCGAGAAGAA GAAATCCTCC CCGGCGGCCG ACTAG
```

*Fig. 1*

Fig. 2A (SEQ ID NO: 3)

```
  1 ATGGCCAATA CCAAATATAA CAAAGAGTTC CTGCTGTACC TGGCCGGCTT
 51 TGTGGACGGT GACGGTAGCA TCATCGCTCA GATTAAACCA AACCAGTCTT
101 ATAAATTCAA GCATCAGCTG TCCCTGACCT TTCAGGTGAC TCAAAAGACC
151 CAGCGCCGTT GGTTTCTGGA CAAACTGGTG GATGAAATTG GCGTTGGTTA
201 CGTACGTGAT CGCGGTAGCG TTTCCGATTA CATTCTGAGC GAAATCAAGC
251 CGCTGCACAA CTTCCTGACT CAACTGCAAC CGTTTCTGAA ACTGAAACAG
301 AAACAGGCAA ACCTGGTTCT GAAAATTATC GAACAGCTGC CGTCTGCAAA
351 AGAATCCCCG GACAAATTCC TGGAAGTTTG TACCTGGGTG GATCAGATTG
401 CAGCTCTGAA CGATTCTAAG ACGCGTAAAA CCACTTCTGA AACCGTTCGT
451 GCTGTGCTGG ACAGCCTGAG CGAGAAGAAG AAATCCTCCC CG
```

Fig. 2B (SEQ ID NO: 4)

```
  1 ATGGCCAACA CTAAGTACAA TAAAGAATTT CTCCTGTATC TGGCAGGTTT
 51 CGTCGACGGC GATGGCTCCA TTATCGCACA GATCAAGCCG AATCAGAGCT
101 ACAAGTTTAA ACACCAACTG TCTCTCACTT TCCAGGTTAC CCAGAAAACT
151 CAACGTCGCT GGTTCCTGGA TAAGCTGGTA GATGAGATCG GTGTGGGCTA
201 TGTACGCGAC CGTGGCTCTG TGAGCGACTA TATCCTGTCT GAGATTAAAC
251 CACTGCATAA TTTTCTGACC CAGCTGCAGC CGTTCCTCAA GCTGAAGCAA
301 AAACAGGCCA ATCTCGTGCT GAAGATCATT GAGCAACTGC CATCCGCCAA
351 AGAGTCTCCG GATAAATTTC TGGAGGTCTG CACTTGGGTT GACCAAATCG
401 CTGCACTCAA CGACTCCAAA ACCCGCAAGA CGACCAGCGA GACTGTACGC
451 GCAGTTCTGG ATTCTCTCTC GAAAAAAAG AAGTCTAGCC CG
```

Fig. 2C (SEQ ID NO: 5)

```
  1 ATGGCCAATA CCAAATATAA CAAAGAGTTC CTGCTGTACC TGGCCGGCTT
 51 TGTGGACGGT GACGGTAGCA TCATCGCTCA GATTAAACCA AACCAGTCTT
101 ATAAGTTTAA ACATCAGCTA AGCTTGACCT TTCAGGTGAC TCAAAAGACC
151 CAGCGCCGTT GGTTTCTGGA CAAACTAGTG GATGAAATTG GCGTTGGTTA
201 CGTACGTGAT CGCGGATCCG TTTCCAACTA CATCTTAAGC GAAATCAAGC
251 CGCTGCACAA CTTCCTGACT CAACTGCAGC CGTTTCTGAA ACTGAAACAG
301 AAACAGGCAA ACCTGGTTCT GAAAATTATC GAACAGCTGC CGTCTGCAAA
351 AGAATCCCCG GACAAATTCC TGGAACTTTG TACCTGGGTG GATCAGATTG
401 CAGCTCTGAA CGATTCTAAG ACGCGTAAAA CCACTTCTGA AACCGTTCGT
451 GCTGTGCTGG ACAGCCTGAG CGAGAAGAAG AAATCCTCCC CG
```

Fig. 2D

UlibIfor (SEQ ID NO: 6)
ACGACGGCCA GTGAATTCAC CATGGCCAAT ACCAAATATA AC

UlibIrev (SEQ ID NO: 7)
1   CACCTGAAAG GTCAAGCTTA GMBBATGTTT AAACTTMBBA GACTGMBBTG
51  GMBBAATMBB AGCGATGATG CTACC UlibIIfor (SEQ ID NO: 8)
GTTTAAACAT CAGCTAAGCT TGACCTTTVV KGTGACTCAA AAGACCCAG UlibIIrev (SEQ ID NO: 9)
GATGTAGTTG GAAACGGATC CMBBATCMBB TACGTAACCA ACGCC V = A or G or C
M = A or C
B = G or C or T
K = G or T

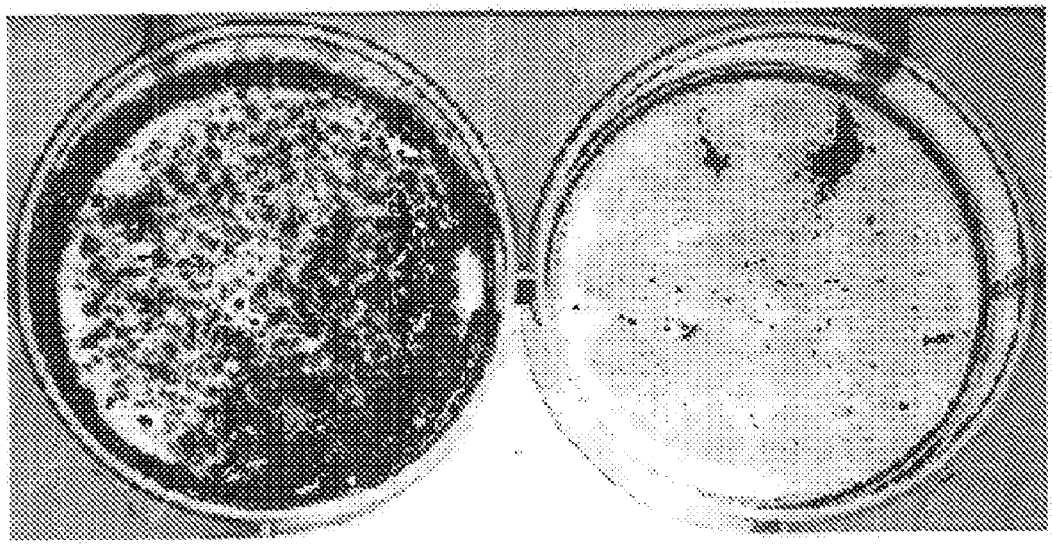
Fig. 5A negative control
Fig. 5B ISce-I

| C1234 | TCAAACGTCGTGAGACAGTTTGG |
| C1221 | TCAAACGTCGTACGACGTTTTGA |
| C4334 | CCAAACTGTCTCGAGACAGTTTGG |
| H1234 | GGAGAAGCCTTAAGACATTTTGA |
| H1221 | GGAGAAGCCTTAAGGCTTCTTCC |
| H4334 | TCAAAATGTCTTAAGACATTTTGA |

Fig. 9

USE OF MEGANUCLEASES FOR INDUCING HOMOLOGOUS RECOMBINATION EX VIVO AND IN TOTO IN VERTEBRATE SOMATIC TISSUES AND APPLICATION THEREOF

CROSS-REFERENCE TO RELATED APPLICATIONS

The present application is a continuation of U.S. Ser. No. 10/543,557, which entered the U.S. National Stage on Jul. 27, 2005, as a National Stage (371) application of PC-T/IB04/00848 (compliance with 35 U.S.C. §371(c) on Mar. 14, 2006), filed on Jan. 28, 2004, and claims priority to U.S. 60/491,535, filed on Aug. 1, 2003, and U.S. 60/442,911, filed on Jan. 28, 2003.

SEQUENCE LISTING

The instant application contains a Sequence Listing which has been submitted via EFS-Web and is hereby incorporated by reference in its entirety. Said ASCII copy, created on Aug. 13, 2010, is named 355503US.txt and is 13,703 bytes in size.

FIELD OF THE INVENTION

The present invention relates to the use of meganucleases for inducing homologous recombination ex vivo and in toto in vertebrate somatic tissues and to its application for genome engineering and gene therapy.

BACKGROUND OF THE INVENTION

Homologous gene targeting has been widely used in the past to obtain site-specific and precise genome surgery (Thomas and Capecchi, 1986, Nature, 324, 34-8; Thomas et al., 1986, Cell, 44, 419-28; Thomas and Capecchi, 1986, Cold Spring Harb Symp Quant Biol, 51 Pt 2, 1101-13; Doetschman et al., 1988, PNAS, 85, 8583-7). Homologous gene targeting relies on the homologous recombination machinery, one of the endogenous maintenance systems of the cell. Since this system has been well conserved throughout evolution, gene targeting could be used in organisms as different as bacteria, yeast, filamentous fungi, mammals, insects, and plants.

One direct application is the modulation of gene expression by modifying the regulatory sequences surrounding the gene (EP 419621; U.S. Pat. Nos. 6,528,313; 6,528,314; 5,272,071; 5,641,670). Correction of mutated genes by homologous recombination is another application (Fischer et al., 2002, Isr Med Assoc J, 4, 51-4). A deleterious mutation can often be complemented by the introduction of a wild type gene anywhere else in the genome. However, there are three major drawbacks in such an approach (random transgenesis). First, the mutated gene is still present. Certain mutation will result in a gain of function, that will not be complemented by the wild type gene, or that can at least interfere with the wild type gene. Second, gene expression often depends on very long tracts of surrounding sequences. In higher eukaryotes, these sequences can span over several hundreds of kbs, and are necessary for the precise tuning of gene expression during the cell cycle, development, or in response to physiological signals. Even though transgenic sequences involve most of the time a few kbs, there is no way they can restore a fully wild type phenotype. This problem can however be alleviated by transformation with very large sequences (BAC), but it requires additional skills. Third, random transgenesis results in insertions anywhere in the genome, with a non-nul probability of a deleterious effect: insertion in a gene will disrupt the gene or its proper regulation. Such deleterious effect have been fully illustrated recently in gene therapy trials for SCID patients (Fischer et al., precited), which resulted in cases of leukemia-like syndromes, probably as a consequence of deleterious insertions of the virus-borne transgenes.

In contrast with random transgenesis, homologous recombination allows the precise modification of a chromosomal locus: it can result in gene deletion, gene insertion, or gene replacement, depending on the targeting vector. In addition, subtle changes can be introduced in a specific locus, including the modification of coding and regulatory sequences (EP 419621; U.S. Pat. Nos. 6,528,313; 6,528,314; 5,272,071; 5,641,670; 6,063,630).

These specific advantages should make homologous gene targeting a universal tool for genome engineering, and the only safe methodology for gene therapy. However, the use of homologous recombination is limited by its poor efficiency in most cells. Although homologous gene targeting is extremely efficient in the yeast *Saccharomyces cerevisiae* (Paques and Haber, 1999, Microbiol Mol Biol Rev, 63, 349-404), the moss *Physcomitrella patens* (Schaefer and Zryd, 1997, Plant J, 11, 1195-206), certain mutant *Escherichia coli* strains (Murphy, 1998, J. Bacteriol, 180, 2063-71; Zhang et al., 1998, Nat Genet, 20, 123-8), and in avian cell lines such as DT40 (Buerstedde and Takeda, 1991, Cell, 67, 179-88), its efficiency remains extremely low in most cells and organisms. For example in cultured mammalian cells, such recombination events usually occur in only one in ten thousands cells which have taken up the relevant correcting or targeting DNA.

As a consequence, many approaches have been used to improve the efficiency of homologous gene targeting. Chimeraplasty (Yoon et al., 1996, PNAS, 93, 2071-6), Small Fragment Homologous Recombination (Goncz et al., 2002, Gene Ther, 9, 691-4) and Triplex Forming Oligonucleotides (Gorman and Glazer, 2001, Curr Mol Med, 1, 391-9) are as many examples. However, the most robust and efficient way to improve homologous gene targeting remains to deliver a DNA double-strand break (DSB) in the locus of interest (U.S. Pat. Nos. 5,474,896; 5,792,632; 5,866,361; 5,948,678; 5,948,678, 5,962,327; 6,395,959; 6,238,924; 5,830,729). This method improves the targeting efficiency by several orders of magnitude in mammalian cells (Donoho et al., 1998, Mol Cell Biol, 18, 4070-8; Rouet et al., 1994, Mol Cell Biol, 14, 8096-106; Choulika et al., 1995, Mol Cell Biol, 15, 1968-73; Cohen-Tannoudji et al., 1998, Mol Cell Biol, 18, 1444-8; Porteus and Baltimore, 2003, Science, 300, 763; Porteus et al., 2003, Mol Cell Biol, 23, 3558-65; Miller et al., 2003, Mol Cell Biol, 23, 3550-7) and allows gene targeting in plants (Puchta et al., 1993, Nucleic Acids Res, 21, 5034-40) and *Drosophila* (Bibikova et al., 2003, Science, 300, 764).

Therefore, the introduction of the double-strand break is accompanied by the introduction of a targeting segment of DNA homologous to the region surrounding the cleavage site, which results in the efficient introduction of the targeting sequences into the locus (either to repair a genetic lesion or to alter the chromosomal DNA in some specific way). Alternatively, the induction of a double-strand break at a site of interest is employed to obtain correction of a genetic lesion via a gene conversion event in which the homologous chromosomal DNA sequences from an other copy of the gene donates sequences to the sequences where the double-strand break was induced. This latter strategy leads to the correction of genetic diseases either in which one copy of a defective gene causes the disease phenotype (such as occurs in the case of dominant mutations) or in which mutations occur in both alleles of the gene, but at different locations (as is the case of compound heterozygous mutations), (WO 96/14408; WO 00/46386; U.S. Pat. No. 5,830,729; Choulika et al., precited; Donoho et al., precited; Rouet et al., precited).

However, the delivery of site-specific DSBs proved to be another challenge. It requires the use of site-specific endonucleases recognizing large sequences. Such very rare-cutting endonucleases recognizing sequences larger than 12 base pairs are called meganucleases. Ideally, one would like to use endonucleases cutting only once in the genome of interest, the cleavage being limited to the locus of interest.

In the wild, such endonucleases are essentially represented by homing endonucleases (Chevalier and Stoddard, 2001, N.A.R., 29, 3757-74). Homing endonucleases are found in fungi, algae, eubacteria and archae, and are often encoded in mobile genetic elements. Their cleavage activities initiate the spreading of these mobile elements by homologous recombination. The biology of HO (Haber, 1998, Annu Rev Genet, 32, 561-99; Haber, 1995, Bioessays, 17, 609-20), I-SceI (Jacquier and Dujon, 1985, Cell, 41, 383-94; Fairhead and Dujon, 1993, Mol Gen Genet, 240, 170-8; Colleaux et al., 1988, PNAS, 85, 6022-6; Perrin et al., 1993, Embo J, 12, 2939-47; Plessis et al., 1992, Genetics, 130, 451-60) and I-TevI endonucleases (Bell-Pedersen et al., 1989, Gene, 82, 119-26; Bell-Pedersen et al., 1990, Nucleic Acids Res, 18, 3763-70; Mueller et al., 1996, Genes Dev, 10, 2158-66) are among the many paradigms for such DSB-induced recombination events.

HO and I-SceI have been used to induce homologous gene targeting in yeast (Haber, 1995, precited; Fairhead and Dujon, 1993, precited; Plessis et al., 1992, precited; U.S. Pat. Nos. 5,792,632 and 6,238,924), in cultured mammalian cells (Donoho et al.; Rouet et al.; Choulika et al.; Cohen-Tannoudji et al., precited; U.S. Pat. Nos. 5,792,632; 5,830,729 and 6,238,924) and plants (Puchta et al., 1996, PNAS, 93, 5055-60; U.S. Pat. Nos. 5,792,632 and 6,238,924). Meganucleases have also been used to trigger various intra- and interchromosomal rearrangements based on DSB-induced homologous recombinations in bacteria (Posfai et al., 1999, N.A.R., 27, 4409-15), yeast (Paques and Haber, 1999, Microbiol Mol Biol Rev, 63, 349-404), plants (Siebert and Puchta, 2002, Plant Cell, 14, 1121-31; Chiurazzi et al., 1996, Plant Cell, 8, 2057-66; Puchta, 1999, Genetics, 152, 1173-81), insects (Rong et al., 2002, Genes Dev, 16, 1568-81) and cultured mammalian cells (Lin and Waldman, 2001, Genetics, 158, 1665-74; Liang et al., 1998, PNAS, 95, 5172-7).

Group II introns proteins can also be used as meganucleases. The biology of these proteins is much more complex than the biology of homing endonucleases encoded by group I introns and inteins (Chevalier and Stoddard, precited). The protein is involved in intron splicing, and forms a ribonucleic particle with the spliced RNA molecule. This complex displays different activities including reverse splicing (of the RNA intron in a DNA strand from the target gene), nicking (of the second DNA strand in the novel gene) and reverse transcriptase (which copies the inserted RNA into a DNA strand). The final insertion of the intron into the target gene depends on all these activities. These proteins seem to induce homologous recombination, with a DSB intermediate, when the reverse transcriptase activity is mutated (Karberg et al., 2001, Nat. Biotechnol, 19, 1162-7).

Unfortunately, this method of genome engineering by using natural meganucleases for inducing homologous recombination by a double-strand break is limited by the introduction of a recognition and cleavage site of said natural meganuclease at the position where the recombinational event is desired.

Up today, in a first approach for generating new meganucleases (artificial or man-made meganucleases), some chimeric restriction enzymes have been prepared through hybrids between a DNA-binding domain (namely a zinc finger domain) and a catalytic domain (the non-specific DNA-cleavage domain from the natural restriction enzyme Fok I), (Smith et al, 2000, N.A.R, 28, 3361-9; Smith et al., 1999, Nucleic Acids Res., 27, 274-281; Kim et al., 1996, PNAS, 93, 1156-60; Kim & Chandrasegaran, 1994, PNAS, 91, 883-7; WO 95/09233; WO 94/18313; U.S. Pat. No. 5,436,150). The resulting so-called Zinc-finger nucleases have been used to induce tandem repeat recombination in *Xenopus* oocytes (Bibikova et al., 2001, Mol Cell Biol, 21, 289-97), and homologous gene targeting in cultured mammalian cell lines (Porteus and Baltimore, precited) and *Drosophila* (Bibikova et al., precited).

Another approach consisted of embedding DNA binding and catalytic activities within a single structural unit, such as a type II restriction endonuclease. However, efforts to increase the length of recognition sequence or alter the specificity of these enzymes have resulted in the loss of catalytic activity or overall diminution of specificity due to the tight interdependence of enzyme structure, substrate recognition and catalysis (Lanio et al., 2000, Protein Eng., 13, 275-281).

Based on homing endonuclease, Chevalier et al. (2002, Molecular Cell, 10, 895-905) have also generated an artificial highly specific endonuclease by fusing domains of homing endonucleases I-Dmo I and I-Cre I. The resulting enzyme binds a long chimeric DNA target site and cleaves it precisely at a rate equivalent to its natural parents. However, this experiment leads to one endonuclease with a new specificity but it is not applicable to find an endonuclease that recognizes and cleaves any desired polynucleotide sequence.

Fusions between nucleic acids and chemical compounds are another class of artificial meganucleases, wherein DNA binding and specificity rely on an oligonucleotide and cleavage on a chemical compound tethered to the oligonucleotide. The chemical compounds can have an endogenous cleavage activity, or cleave when complexed with topoisomerases (Arimondo et al., 2001, Angew Chem Int Ed Engl, 40, 3045-3048; Arimondo and Helene, 2001, Curr Med Chem Anti-Canc Agents, 1, 219-35).

Thus, meganuclease-induced recombination appears to be an extremely powerful tool for introducing targeted modifications in genomes. In addition, the development of new meganucleases able to cleave DNA at the position where the recombinational event is desired, for example derived from Zinc-finger nucleases, or from natural homing endonucleases, would allow targeting at any given locus at will and with a reasonable efficiency.

Nevertheless, it clearly emerges from the above analysis of the prior art that the use of this technology in animals has so far been mostly limited to its applications in vitro or ex vivo in cultured cells, except in the case of *Drosophila* (Bibikova et al. 2003, precited), where it could be used to induce recombination in a living animal, in the germline and somatic tissues.

It would be extremely advantageous to be able to use this technology to induce recombination in a whole organism, in the somatic tissues:

This could be used for tissue-specific genome engineering in animal models or foreign sequences excision in genetically-modified organisms (once the trait depending on these foreign sequences is not useful anymore). DSBs between two tandem repeats induce very high levels of homologous recombination resulting in deletion of one repeat together with all the intervening sequences (Paques and Haber, 1999, Microbiol Mol Biol Rev, 63, 349-404), and this can easily be used for the removal of any transgene with an appropriate design.

One other major application would be the use of meganuclease-induced recombination in gene therapy. In a number of cases, an ex vivo approach could be used: precursor stem cells would be taken from the patients, healed ex vivo, and grafted back in the deficient tissue. So far, ex vivo techniques have been mostly used with blood cells in SCID and other syndromes (although random insertion was used instead of homologous recombination (Fischer et al., precited). The manipulation of stem cells makes it an attractive approach for other tissues. However, the use of meganuclease-induced recombination in toto would bypass the ex vivo steps and enlarge the range of tissues that can be treated.

There are however two major reasons why this approach is not straightforward:

First, this would require the delivery of a meganuclease in the appropriate tissue.

Second, cells in a living organism do not necessarily behave as cultured cells or germinal cells. Cultured cells and early (and sometimes late) germ cells are dividing cells, going through G1, S, G2, and M phases. In contrast, most cells in an adult animal are differentiated cells, stuck in a G0 phase. Many results indicate and/or suggest that homologous recombination does not have the same efficiency in all phases of the cell cycle (Takata et al., 1998, Embo J, 17, 5497-508; Kadyk and Hartwell, 1992, Genetics, 132, 387-402; Gasior et al., 2001, PNAS, 98, 8411-8; Essers et al., 1997, Cell, 89, 195-204). In general, the different tissues might have distinct proficiencies for homologous gene conversions. Therefore, it is not clear whether gene targeting and meganuclease-induced genome engineering by homologous recombination could be used in whole organisms, or even for ex vivo approaches, which relies on specific cell types for which recombination proficiencies are largely unknown.

Surprisingly, by using appropriate targeting constructs and meganuclease expression vectors, the Inventors have shown that meganucleases are indeed able to induce targeted homologous recombination ex vivo and in toto, in vertebrate somatic tissues.

Accordingly, meganucleases can be used for repairing a specific sequence, modifying a specific sequence, for attenuating or activating an endogenous gene of interest, for inactivating or deleting an endogenous gene of interest or part thereof, for introducing a mutation into a site of interest or for introducing an exogenous gene or part thereof, in vertebrate somatic tissues.

Therefore, these results establish a basis for efficient site-specific genomic manipulation in mammalian somatic tissues for experimental purposes and raise the possibility of therapeutically correcting mutations by gene targeting.

DETAILED DISCUSSION OF THE INVENTION

Thus, the purpose of the present invention is to use meganucleases for inducing homologous recombination ex vivo and in toto in vertebrate somatic tissues.

Applications are in different fields: research, including animal models generation (tissue specific genome surgery: knock-in or knock-out); agricultural biotechnology (addition or removal of a trait, marker excision, protein production) and therapeutics (gene therapy: gene repair ex vivo and in toto and antiviral therapy: excision of virus ex vivo and in toto).

Accordingly, the present invention relates to the use of at least one meganuclease for the preparation of a medicament for preventing, improving or curing a genetic disease in a vertebrate in need thereof; said medicament being administered by any means to said vertebrate.

The invention, also concerns the use of at least one meganuclease for the preparation of a medicament for preventing, improving or curing a disease caused by an infectious agent that presents a DNA intermediate, in a vertebrate in need thereof; said medicament being administered by any means to said vertebrate. Preferably, said infectious agent is a virus.

Another object of the present invention is the use of at least one meganuclease for genome engineering of non-human vertebrate somatic tissues, for non-therapeutic purpose, by introducing said meganuclease into the body of said non-human vertebrate.

DEFINITIONS

In the present application, by "meganuclease" is intended a double-stranded endonuclease having a large polynucleotide recognition site, at least 12 bp, preferably from 12 by to 60 bp. Said meganuclease is also called rare-cutting or very rare-cutting endonuclease. Said meganuclease is either monomeric or dimeric. It includes any natural meganuclease such as a homing endonuclease, but also any artificial or man-made meganuclease endowed with such high specificity, either derived from homing endonucleases of group I introns and inteins, or other proteins such as Zinc-Finger proteins or group II intron proteins, or compounds such as nucleic acid fused with chemical compounds.

In particular, artificial meganucleases include the so-called "custom-made meganuclease" which is a meganuclease derived from any initial meganuclease, either natural or not, presenting a recognition and cleavage site different from the site of the initial one; zinc-finger nucleases may also be considered as custom-made meganucleases. By "different" is intended that the custom-made meganuclease cleaves the novel site with an efficacy at least 10 fold more than the natural meganuclease, preferably at least 50 fold, more preferably at least 100 fold. "Natural" refers to the fact that an object can be found in nature. For example, a meganuclease that is present in an organism, that can be isolated from a source in nature and which has not been intentionally modified by man in the laboratory is natural.

By "in toto" is intended that the homologous recombination event induced by the meganuclease takes place in vivo in the body of a vertebrate; said meganuclease is introduced into the body of said vertebrate by any convenient mean.

By "ex vivo" is intended that the homologous recombination event induced by the meganuclease takes place in somatic cells removed from the body of a vertebrate; said meganuclease is introduced (ex vivo) into the cells of said vertebrate by any convenient mean and the modified cells are then returned into the body of said vertebrate.

By "somatic tissue" is intended any tissue within the body of an organism including any type of cells from the precursor cells (stem cells) to the fully differentiated cells, with the exception of the germ line cells.

"Identity" refers to sequence identity between two nucleic acid molecules or polypeptides. Identity can be determined by comparing a position in each sequence which may be aligned for purposes of comparison. When a position in the compared sequence is occupied by the same base, then the molecules are identical at that position. A degree of similarity or identity between nucleic acid or amino acid sequences is a function of the number of identical or matching nucleotides at positions shared by the nucleic acid sequences. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default settings.

By "homologous" is intended a sequence with enough identity to another one to lead to a homologous recombination between sequences, more particularly having at least 95% identity, preferably 97%, and more preferably 99%.

The phrases "site of interest", "target site" and "specific site", as used herein, refer to a distinct DNA location, preferably a chromosomal location, at which a double stranded break (cleavage) is to be induced by the meganuclease.

As used herein, the term "individual" includes mammals, as well as other vertebrates (e.g., birds, fish and reptiles). The terms "mammal" and "mammalian", as used herein, refer to any vertebrate animal, including monotremes, marsupials and placental, that suckle their young and either give birth to living young (eutharian or placental mammals) or are egg-laying (metatharian or nonplacental mammals). Examples of mammalian species include humans and other primates (e.g., monkeys, chimpanzees), rodents (e.g., rats, mice, guinea pigs) and ruminants (e.g., cows, pigs, horses).

By "genetic disease" is intended any disease, partially or completely, directly or indirectly, due to an abnormality in one or several genes. Said abnormality can be a mutation, an insertion or a deletion. Said mutation can be a punctual mutation. Said abnormality can affect the coding sequence of the gene or its regulatory sequence. Said abnormality can affect the structure of the genomic sequence or the structure or stability of the encoded mRNA. Said genetic disease can be recessive or dominant.

The term "vector" refers to a nucleic acid molecule capable of transporting another nucleic acid to which it has been linked.

Meganucleases

In another embodiment of the above uses according to the invention, said meganuclease is selected from the group consisting of a homing endonuclease, a zinc-finger nuclease or a meganuclease variant.

homing endonuclease are as described in Chevalier and Stoddard, precited.

Custom-Made Meganucleases zinc-finger nuclease

Meganuclease based on Zinc-Finger domains have the structure described by Smith et al., precited. The meganuclease is a heterodimer of two fusion protein. Each fusion protein includes a DNA-binding domain derived from Zif268 (or other zinc-finger proteins), tethered to a nuclease domain (derived from the FokI endonuclease or other endonucleases) through a linker. The DNA target site includes two external regions of 9 bp, bound by the DNA binding domains, and a central spacer region of 0-15 bp. In each monomer, the DNA binding Zinc-Finger domain has been selected to bind one of the 9 by external regions, as described by Isalan and Choo (2001, Methods Mol Biol, 148, 417-29), Isalan et al. (2001, Nat. Biotechnol, 19, 656-60) and Isalan and Choo (2001, Methods Enzymol, 340, 593-609). Selection can be made by phage display, as described by the authors, but other methods such as screening in yeast or with a bacterial two-hybrid system can also be used, as described by Young et al. (2000, PNAS, 97, 7382-7) and Bae et al. (2003, Nat Biotechnol, 21, 275-80). Also, to enhance specificity, DNA binding domains encompassing 6 Zinc Finger motifs can be used, as described by Klug and collaborators (Moore et al., 2001, PNAS, 98, 1432-6; Papworth et al., 2003, PNAS, 100, 1621-6; Reynolds et al., 2003, PNAS, 100, 1615-20; Moore et al., 2001, PNAS, 98, 1437-41). However, if the endonucleolytic activity relies on a FokI domain, two such monomers have to be used, each one bound to a FokI catalytic site: each FokI catalytic domain cleaving only one strand, it takes two such domains to obtain a double-strand cleavage.

meganuclease variants

Custom-made meganuclease is defined as a meganuclease able to cleave a targeted DNA sequence. This definition includes any meganuclease variant produced by a method comprising the steps of preparing a library of meganuclease variants and isolating, by selection and/or screening, the variants able to cleave the targeted DNA sequence. Said custom-made meganuclease which is derived from any initial meganuclease by introduction of diversity, presents a recognition and cleavage site different from the site of the initial one.

The diversity could be introduced in the meganuclease by any method available for the man skilled in the art. Preferably, the diversity is introduced by targeted mutagenesis (i.e. cassette mutagenesis, oligonucleotide directed codon mutagenesis, targeted random mutagenesis), by random mutagenesis (i.e. mutator strains, *Neurospora crassa* system (U.S. Pat. No. 6,232,112; WO01/70946, error-prone PCR), by DNA shuffling, by directed mutation or a combination of these technologies (See Current Protocols in Molecular Biology, Chapter 8 "Mutagenesis in cloned DNA", Eds Ausubel et al., John Wiley and Sons). The meganuclease variants are preferably prepared by the targeted mutagenesis of the initial meganuclease. The diversity is introduced at positions of the residues contacting the DNA target or interacting (directly or indirectly) with the DNA target. The diversity is preferably introduced in regions interacting with the DNA target, and more preferably introduced at the positions of the interacting amino acids. In libraries generated by targeted mutagenesis, the 20 amino acids can be introduced at the chosen variable positions. Preferably, the amino acids present at the variable positions are the amino acids well-known to be generally involved in protein-DNA interaction. More particularly, these amino acids are generally the hydrophilic amino acids. More preferably, the amino acids present at the variable positions comprise D, E, H, K, N, Q, R, S, T, Y. Optionally, the amino acids present at the variable positions are selected from the group consisting of D, E, H, K, N, Q, R, S, T, Y. Synthetic or modified amino acids may also be used.

One preferred way to generate a directed library is the use of degenerated codons at the positions where diversity has to be introduced. Several types of degenerated codons could be used. A degenerated codon N N K ([ATCG] [ATCG] [TG]) leads to 32 different codons encoding the 20 amino acids and one stop. A degenerated codon N V K ([ATCG] [ACG] [TG]) leads to 24 different codons encoding the 15 amino acids and one stop. A degenerated codon V V K ([ACG] [ACG] [TG]) leads to 18 different codons encoding the 12 amino acids (A, D, E, G, H, K, N, P, Q, R, S, T) and no stop. A degenerated codon R V K ([AG] [ACG] [TG]) leads to 12 different codons encoding the 9 amino acids (A, D, E, G, K, N, R, S, T). Preferably, a degenerated codon V V K ([ACG] [ACG] [TG]) leading to 18 different codons encoding the 12 amino acids (A, D, E, G, H, K, N, P, Q, R, S, T) is used for generating the library. Indeed, the V V K degenerated codon does not contain any stop codon and comprises all the hydrophilic amino acids.

If a directed library is generated, knowledge on amino acids interacting with the DNA target is useful. This knowledge could be provided, for example, by X-ray crystallography, Alanine scanning, or cross-linking experiments. The amino acids interacting with the DNA target can also be deduced by sequence alignment with a homologous protein.

The custom-made meganuclease is derived from any initial meganuclease. Optionally, the initial meganuclease is selected so as its natural recognition and cleavage site is the closest to the targeted DNA site. Preferably, the initial meganuclease is a homing endonuclease, as specified, in the here above definitions. Homing endonucleases fall into 4 separated families on the basis of well conserved amino acids motifs, namely the LAGLIDADG family (SEQ ID NO: 24), the GIY-YIG family, the His-Cys box family, and the HNH family (Chevalier et al., 2001, N.A.R, 29, 3757-3774).

The detailed three-dimensional structures of several homing endonucleases are known, namely I-Dmo I, PI-Sce I, PI-Pfu I, I-Cre I, I-Ppo I, and a hybrid homing endonuclease I-Dmo I/I-Cre I called E-Dre I (Chevalier et al., 2001, Nat Struct Biol, 8, 312-316; Duan et al., 1997, Cell, 89, 555-564; Heath et al., 1997, Nat Struct Biol, 4, 468-476; Hu et al., 2000, J Biol Chem, 275, 2705-2712; Ichiyanagi et al., 2000, J Mol Biol, 300, 889-901; Jurica et al., 1998, Mol Cell, 2, 469-476; Poland et al., 2000, J Biol Chem, 275, 16408-16413; Silva et al., 1999, J Mol Biol, 286, 1123-1136; Chevalier et al., 2002, Molecular Cell, 10, 895-905).

The LAGLIDADG family (SEQ ID NO: 24) is the largest family of proteins clustered by their most general conserved sequence motif: one or two copies of a twelve-residue sequence: the di-dodecapeptide, also called LAGLIDADG motif (SEQ ID NO: 24). Homing endonucleases with one dodecapeptide (D) are around 20 kDa in molecular mass and act as homodimer. Those with two copies (DD) range from 25 kDa (230 AA) to 50 kDa (HO, 545 AA) with 70 to 150 residues between each motif and act as monomer. Cleavage is inside the recognition site, leaving 4 nt staggered cut with 3'OH overhangs. I-Ceu I, and I-Cre I illustrate the homodimeric homing endonucleases with one Dodecapeptide motif (mono-dodecapeptide). I-Dmo I, I-Sce I, PI-Pfu I and PI-Sce I illustrate monomeric homing endonucleases with two Dodecapeptide motifs.

The initial LAGLIDADG (SEQ ID NO: 24) homing endonuclease can be selected from the group consisting of: I-Sce I, I-Chu I, I-Dmo I, I-Cre I, I-Csm I, PI-Sce I, PI-Tli I, PI-Mtu I, I-Ceu I, I-Sce II, I-Sce III, HO, PI-Civ I, PI-Ctr I, PI-Aae I, PI-Bsu I, PI-Dha I, PI-Dra I, PI-May I, PI-Mch I, PI-Mfu I, PI-Mfl I, PI-Mga I, PI-Mgo I, PI-Min I, PI-Mka I, PI-Mle I, PI-Mma I, PI-Msh I, PI-Msm I, PI-Mth I, PI-Mtu I, PI-Mxe I, PI-Npu I, PI-Pfu I, PI-Rma I, PI-Spb I, PI-Ssp I, PI-Fac I, PI-Mja I, PI-Pho I, PI-Tag I, PI-Thy I, PI-Tko I, and PI-Tsp I; preferably, I-Sce I, I-Chu I, I-Dmo I, I-Cre I, I-Csm I, PI-Sce I, PI-Pfu I, PI-Tli I, PI-Mtu I, and I-Ceu I; more preferably, I-Dmo I, I-Cre I, PI-Sce I, and PI-Pfu I; still more preferably I-Cre I.

The four structures of LAGLIDADG (SEQ ID NO: 24) homing endonucleases, namely those of I-Dmo I, PI-Sce I, PI-Pfu I, and I-Cre I, reveal the functional significance of the LAGLIDADG motif (SEQ ID NO: 24), and the nature of the DNA-binding interface. The core α β β αβ β α fold of the homodimer homing endonuclease is repeated twice in the monomer homing endonuclease and confers upon the monomer a pseudo-dimeric structure. The first α-helix of each domain or subunit contains the defining LAGLIDADG motif (SEQ ID NO: 24). The two LAGLIDADG (SEQ ID NO: 24) helices of each protein form a tightly packed dimer or domain interface. The DNA binding interface is formed by the four β-strands of each domain or subunit that fold into an antiparallel β-sheet. A minimal DNA binding moiety could be defined in the LAGLIDADG (SEQ ID NO: 24) homing endonucleases as a β-hairpin (2 β-strands connected by a loop or turn), two such β-hairpins being connected into the 4-stranded β-sheet.

Each domain or subunit interacts with a half recognition site. The <<external>> quarter recognition site can be defined by its interaction with only one of the 2 β-hairpins of each domain or subunit.

Therefore, meganuclease variants derived from LAGLIDADG (SEQ ID NO: 24) homing endonuclease can be fragmented in several directed libraries. This fragmented approach for the evolution of an initial meganuclease allows the introduction of a greater diversity (more amino acids at a position and/or more diversificated positions). In each library, the diversity is introduced only in the region involved in the interaction with a half or a quarter recognition site, the targeted DNA being modified only for the part interacting with the region comprising the introduced diversity. More particularly, if a new half site is searched for, then the diversity is preferably introduced in the 4-stranded β-sheet of one domain or subunit, more preferably at the positions of the DNA interacting amino acids in this structure. If a new quarter site is searched for, then the diversity is introduced in the corresponding β-hairpin, more preferably at the positions of the DNA interacting amino acids of this structure.

Preferably, a set of libraries covers the entire targeted DNA site. Hence, if the libraries comprise diversity only in the region interacting with a half-site, at least two libraries, preferably two, are necessary. However, if the initial meganuclease is a dimer, one library is enough with a half-site approach. If the libraries comprise diversity only in the region interacting with a quarter site, at least four libraries, preferably four, are necessary. If the initial meganuclease is a dimer, two libraries can be enough with a quarter site approach.

After the selection or screening of the primary libraries, the selected elements from the primary libraries are fused or combined in a subsequent library for a new cycle of selection. For example, two libraries can be fused by shuffling. A new cycle of selection could be then done on the whole targeted DNA site. Optionally, the new cycle of selection can be done on a half targeted DNA site if the first libraries are based on a quarter site. Subsequently, the results of the selection and/or screening of the half site are combined to give a final library which can be screened for the whole targeted DNA site.

Alternatively, the best elements from each libraries are joined together in order to obtain a meganuclease able to bind and cleave the targeted DNA site.

In another approach, a library with diversity located only in the region involved in the interaction with a half or a quarter recognition site is prepared. Then, after selection or screening of this library, the selected elements from the library are modified such as to introduce diversity in another region involved in the interaction with recognition site, leading to a subsequent library. Libraries are generated until the complete targeted DNA site is bound and cleaved by the selected meganuclease.

More specifically, for the dimeric homing endonuclease (such as I-Cre I and I-Ceu I), a library can be generated by introducing diversity only in the region interacting with a half-site, a half site corresponding to one monomer of the initial homing endonuclease. This library can be used for selection and/or screening on each half sites of the target DNA sequence. When positive elements from the library have been selected for each half sites, a variant for the first half site and a variant for the other half site are brought together for binding and cleaving the whole target DNA sequence. Alternatively, the positive variants can be introduced in a single chain meganuclease structure. As described in Example 1, a single chain meganuclease is an enzyme in which the two monomers of the initial dimeric homing endonuclease are covalently bound by a linker.

If an approach by a quarter site is chosen from an initial dimer homing endonuclease, at least two libraries are generated by introducing diversity only in the region involved in the interaction with each quarter recognition sites. After the selection or screening of the primary libraries, the selected variants from the primary libraries are fused in a subsequent library for a new cycle of selection on the half site. Alternatively, the best elements from each libraries are joined together to obtain a monomer able to bind the half site. Otherwise, a library with diversity only in the region involved in the interaction with a quarter recognition site is prepared. Then, after selection or screening of this library, the selected elements from the library are modified such as to introduce diversity in the region involved in the interaction with the other quarter site, leading to a subsequent library. The selection and/or screening of this second library lead to the variants monomer able to bind the half site. When positive elements from the library have been selected for each half sites, a variant for the first half site and a variant for the other half site are brought together for binding and cleaving the target DNA sequence. Alternatively, the positive variants can be introduced in a single chain meganuclease structure.

Preferably, the custom-made meganuclease which recognizes and cleaves a desired polynucleotide target is derived from the directed evolution of the homing endonuclease I-Cre I. As the homing endonuclease is a homodimer, the approach in this case is based either on the half recognition site or on the quarter site.

The directed evolution is based on a library of I-Cre I variants. These I-Cre I variants present a diversity of amino acids at several positions predicted to interact with the polynucleotide target.

The X-ray structure of I-Cre endonuclease with its DNA target predicted that the following positions are involved: Q26, K28, N30, S32, Y33, Q38, Q44, R68, R70 and T140. Seligman et al (supra) showed that the positions S32 and T140 appear to be relatively unimportant for DNA recognition.

A set of I-Cre I variants is prepared by introducing amino acid diversity in positions selected from the group consisting of: Q26, K28, N30, S32, Y33, Q38, Q44, R68, R70 and T140. In a preferred embodiment, a set of I-Cre I variants is prepared by introducing diversity in positions: a) Q26, K28, N30, Y33, Q38, Q44, R68, R70, T140; b) Q26, K28, N30, Y33, Q38, Q44, R68, R70; c) Q26, K28, N30, Y33, Q44, R68, R70; or d) Q26, K28, Y33, Q38, Q44, R68, R70. Preferably, a set of I-Cre I variants is prepared by introducing diversity in positions Q26, K28, N30, Y33, Q38, Q44, R68, and R70.

Optionally, the residue D75 of I-Cre I could be mutated in an uncharged amino acid such as N. Indeed, this amino acid has an interaction with 2 residues which are preferably modified in the library. As this charge is present in the core of the structure, it could be preferable to abolish this charge.

If the evolution approach of the homing endonuclease I-Cre I is based on the quarter recognition site, replacing the DNA binding residues presented by a β-hairpin (within the 4-stranded b-sheet) is a practical solution. As those residues are part of an element with limited length (i.e. less than 25 residue), they can be mutated together at once, for example by cassette replacement. Visual inspection of structure 1g9y, SEQ ID NO: 23, (I-CreI with its target double-stranded DNA) indicates that the first β-hairpin is a unique or major contributor to the recognition of the last six bases of the target (i.e. either bases −12 to −7 or bases +7 to +12). Thus replacing the sequence from residue S22 to residue Q44, more preferably from residue I24 to residue T42, should be sufficient to specify new interaction specificity for the last six bases of the target site. More preferably, the residues interacting directly with DNA should be modified: I24, Q26, K28, N30, S32, Y33, Q38, S40 and T42. Alternatively (or in addition), the turn at the middle of the β-hairpin, which interacts with the very end of the 24 bp-long DNA target, may be replaced by a short and flexible loop that would be tolerant to DNA bases substitution. For example, residues 30 to 36 could be replaced by 2, 3, 4, 5 or 6 glycine residues (SEQ ID NO: 25). This strategy is worth testing with all meganucleases presenting a comparable 3D structure. The second hairpin could be replaced similarly as a single unit (from residue Y66 to I77). However, while this hairpin interacts predominantly with the internal quarter site (bases −6 to −1 or +1 to +6), other residues (i.e. S22, Q44 and T46) separated from the hairpin may play a role in directing the specificity of interaction. Thus, a library could be created by replacing residues Y66, R68, R70, V73, D75 and I77. In parallel, S22, Q44 and T46 may either be left untouched, replaced by small polar amino acids (G, S or T; more preferably S or T), or randomized to contribute to the library. Mutants selected from separate library (the first wherein randomized residues are I24, Q26, K28, N30, S32, Y33, Q38, S40 and T42 and the second wherein randomized residues are Y66, R68, R70, V73, D75 and I77) can be combined together by standard DNA shuffling methods based on recombination at homologous DNA regions (i.e. the DNA coding for the region between residue 43 and residue 65 is strictly conserved). However, if the second library includes mutations of residues S22, Q44 and T46, recombination becomes impractical, and more classical DNA/protein engineering is required.

If the evolution approach of the homing endonuclease I-Cre I is based on the quarter recognition site, a library of I-Cre I variants is prepared by introducing diversity in positions selected from the group consisting of: a) I24, Q26, K28, N30, S32, Y33, Q38, S40 and T42; or b) Y66, R68, R70, V73, D75, and I77. In the alternative b), the diversity could be also introduced in positions selected from the group consisting of: S22, Q44, and T46.

Alternatively, a custom-made meganuclease which recognizes and cleaves a desired polynucleotide target could be prepared by the directed evolution of single chain I-Cre I endonuclease. A set of single-chain I-Cre I variants is prepared by introducing amino acid diversity in positions selected from the group consisting of: Q26, K28, N30, S32, Y33, Q38, Q44, R68, R70, Q123, K125, N127, S129, Y130, Q135, Q141, R165, R167.

Two properties of the meganuclease can be used for the steps of selection and/or screening, namely the capacity to bind the targeted DNA sequence and the ability to cleave it.

The meganuclease variants can be selected and screened, or only screened. The selection and/or screening can be done directly for the ability of the meganuclease to cleave the targeted DNA sequence. Alternatively, the selection and/or screening can be done for the binding capacity on the targeted DNA sequence, and then for ability of the meganuclease to cleave it. Preferably, the method to prepare a custom-made meganuclease comprises or consists of the following steps:

a) a selection step for the binding ability, a screening step for the binding ability, a selection for the cleavage activity, and a screening step for the cleavage activity;

b) a selection step for the binding ability, a screening step for the binding ability, and a screening step for the cleavage activity;

c) a selection step for the binding ability, a selection for the cleavage activity, and a screening step for the cleavage activity;

d) a screening step for the binding ability and a screening step for the cleavage activity;

e) a selection step for and a screening step for the cleavage activity; or, f) a screening step for the cleavage activity.

More preferably, the method to prepare a custom-made meganuclease comprises or consists of the following steps: a selection step for the binding ability, a selection for the cleavage activity, and a screening step for the cleavage activity. A screening assay for the binding ability after a selection step based on the binding capacity can be done in order to estimate the enrichment of the library for meganuclease variants presenting a binding capacity.

The selection and screening assays are performed on the DNA region in which a double stranded cleavage has to be introduced or a fragment thereof.

Preferably, the targeted sequences comprise at least 15 nucleotides, preferably 18 to 40, more preferably 18 to 30 nucleotides. In case of dimeric meganuclease, the targeted DNA polynucleotide can be reduced to at least 8 nucleotides for binding only. Preferably, the targeted DNA polynucleotide length is less than 10 kb, preferably less than 3 kb, more preferably less than 1 kb. For the DNA binding assay, the targeted DNA polynucleotide length is preferably less than 500 bp, more preferably less than 200 bp.

Any targeted sequence can be used to generate a custom-made meganuclease able to cleave it according. Optionally, the targeted sequence is chosen such as to present the most identity with the original recognition and cleavage site of the initial meganuclease. Therefore, the DNA region in which a double stranded break has to be introduced is analyzed to choose at least 1, 2, 3 or 5 sequences of at least 15 nucleotides length, preferably 18 to 40, more preferably 18 to 30 nucleotides, having at least 25% identity, preferably 50% identity and more preferably 75% identity with the original recognition and cleavage site of the initial meganuclease.

The targeted DNA sequence is adapted to the type of meganuclease variants library. If the library is based on a half site approach, the targeted DNA sequence used for the selection/screening comprises one half original site and one half site of the desired DNA sequence. If the library is based on a quarter site approach, the targeted DNA sequence used for the selection/screening comprises three quarters of the original site and one quarter site of the desired DNA sequence.

The meganuclease variants resulting from the selection and/or screening steps could optionally be an input for another cycle of diversity introduction.

The positive meganuclease variants selected by the selection and/or screening steps are validated by in vitro and/or ex vivo cleavage assay.

The selection and screening of meganuclease variants based on the binding capacity has to be made in conditions that are not compatible with the cleavage activity. For example, most of homing endonucleases need manganese or magnesium for their cleavage activity. Therefore, the binding assays on this type of homing endonuclease variants are done without manganese or magnesium, preferably replaced by calcium.

The binding selection assay is based on the enrichment of the meganuclease variants able to bind the targeted DNA polynucleotide. Therefore, the meganuclease variants encoded by the library are incubated with an immobilized targeted DNA polynucleotide so that meganuclease variants that bind to the immobilized targeted DNA polynucleotide can be differentially partitioned from those that do not present any binding capacity. The meganuclease variants which are bound to the immobilized targeted DNA polynucleotide are then recovered and amplified for a subsequent round of affinity enrichment and amplification. After several rounds of affinity enrichment and amplification, the library members that are thus selected can be isolated. Optionally, the nucleotide sequences encoding the selected meganuclease variants are determined, thereby identifying of the meganuclease variants able to bind the targeted DNA sequence.

The selection of meganuclease variants requires a system linking genotype and phenotype such as phage display (WO91/17271, WO91/18980, and WO91/19818 and WO93/08278; the disclosures of which are incorporated herein by reference), ribosome display (Hanes & Plückthun, PNAS, 1997, vol. 94, 4937-4942; He & Taussig, Nucl. Acids Res. (1997) vol. 25, p 5132-5143) and mRNA-protein fusion (WO00/47775; U.S. Pat. No. 5,843,701; Tabuchi et al FEBS Letters 508 (2001) 309-312; the disclosures of which are incorporated herein by reference).

Phage display involves the presentation of a meganuclease variant on the surface of a filamentous bacteriophage, typically as a fusion with a bacteriophage coat protein. The library of meganuclease variants is introduced into a phage chromosome or phagemid so as to obtain a protein fusion with a bacteriophage coat protein, preferably with the pIII protein. If the initial meganuclease is a homodimer, the monomer variants of the meganuclease are introduced so as to be displayed and the constant monomer can be introduced so as to be produced in the periplasm. The bacteriophage library can be incubated with an immobilized targeted DNA sequence so that elements able to bind the DNA are selected.

mRNA-protein fusion system opens the possibility to select among $10^{13}$ different meganuclease variants. This system consists in the creation of a link between the mRNA and the encoded protein via a puromycin at the 3' end of the mRNA which leads to a covalent mRNA-protein fusion at the end of the translation. Hence, a double-stranded DNA library comprising the coding sequence for the meganuclease variants is used regenerate mRNA templates for translation that contain 3' puromycin. The mRNA-puromycin conjugates are translated in vitro to generate the mRNA-meganuclease fusions. After cDNA synthesis, the fusions are tested for the ability to bind the immobilized targeted DNA polynucleotide. A PCR is then used to generate double-stranded DNA enriched in meganuclease variants presenting the binding capacity. If the initial meganuclease is a homodimer, the constant monomer can be introduced either as DNA or mRNA encoding this monomer or as a monomer protein. In this case, an approach with the single chain meganuclease will be preferably used.

Ribosome display involves a double-stranded DNA library comprising the coding sequence for the meganuclease variants that is used to generate mRNA templates for translation. After a brief incubation, translation is halted by addition of $Mg^{2+}$ and incubation at low temperature or addition of translation inhibitor. The ribosome complexes are then tested for the ability to bind immobilized targeted DNA polynucleotide. The selected mRNA is used to construct cDNA and a PCR generates double-stranded DNA enriched in meganuclease variants presenting the binding capacity. If the initial meganuclease is a homodimer, the constant monomer is introduced either as DNA or mRNA encoding this monomer or as a monomer protein. In this case, an approach with the single chain meganuclease will be preferably used.

The targeted DNA sequence can be immobilized on a solid support. Said solid support could be a column, paramagnetic beads or a well of a microplate. For example, the polynucleotides comprising the targeted DNA sequence present a ligand (such as a biotin) at one end, said ligand allowing the immobilization on a solid support bearing the target of the ligand (for example, streptavidin if biotin is used).

The selection of the meganuclease variants may usually be monitored by a screening assay based on the binding or cleavage capacity of these meganucleases. However, the selected meganuclease variants can be also directly introduced in a selection step based on the cleavage capacity.

In order to perform the screening assay, the selected meganuclease variants need to be cloned. If the selection was done with the phage display system, the clone encoding each meganuclease variants can be easily isolated. If the selection was done by mRNA-protein fusion or ribosome display, the selected meganuclease variants have to be subcloned in expression vector.

The screening assays are preferably performed in microplates (96, 384 or 1536 wells) in which the targeted DNA polynucleotides are immobilized. After expression of the meganuclease variants, these variants are incubated with the immobilized targeted DNA polynucleotides. The meganuclease variants expression can be performed either in vivo or in vitro, preferably by in vitro expression system. Preferably, the meganuclease variants are purified prior to the incubation with the targeted polynucleotide. The retained meganuclease variants are then detected. The detection could be done by several means well known by the man skilled in the art. For example, if phages are used, the detection can be done with antibodies against phages (ELISA). Otherwise, the expression could be done in presence of S35 amino acids in order to obtain radioactive meganucleases. Thus, the binding is estimated by a radioactivity measurement. The invention also considers the others means of detection of DNA binding by meganuclease available to the man skilled in the art.

Optionally, the nucleotide sequences encoding the positively screened meganuclease variants are determined, thereby identifying of the meganuclease variants able to bind the targeted DNA sequence.

The positively screened meganuclease variants have to be tested for their cleavage capacity. Therefore, said meganuclease variants are incorporated in a cleavage selection and/or screening experiment, preferably an in vivo cleavage screening assay. Optionally, said meganuclease variants can be tested by an in vitro cleavage assay.

The screening assay can also be used only for estimate the enrichment in meganuclease variants presenting the binding capacity. This estimation helps to decide if a new round of selection based on the binding capacity is necessary or if the selected library can be submitted to a cleavage selection and/or screening, preferably an in vivo cleavage selection and/or screening.

The selection and screening of meganuclease variants based on the cleavage capacity has to be made in conditions compatible with the cleavage activity. The meganuclease variants used in the selection and/or screening based on cleavage capacity may be either the initial library of meganuclease variants or the meganuclease variants selected and/or screened for the binding activity.

If necessary, the selected and/or screened meganuclease variants are subcloned in an appropriate expression vector for the in vitro and in vivo cleavage assay. Such subcloning step can be performed in batch or individually. More particularly, if the initial meganuclease is a dimer, the subcloning step allows the introduction of the selected library(ies) in a single chain meganuclease structure. If two libraries have been selected and/or screened for two half recognition and cleavage sites, the subcloning step allows to bring together the two selected libraries in a single chain meganuclease structure.

The general principle of an in vivo selection of the meganuclease variants based on their cleavage capacity is that the double-strand break leads to the activation of a positive selection marker or the inactivation of a negative selection marker.

If the selection is based on the inactivation of a negative selection marker, the method involves the use of cell containing an expression vector comprising the coding sequence for a negative selection marker and the targeted DNA sequence for the desired meganuclease and an expression vector comprising the library of meganuclease variants. Preferably said expression vector is a plasmid. Preferably said targeted DNA sequence is located either near the negative selection gene or in the negative selection gene, preferably between the promoter driving the expression of the negative selection and the ORF. The expression of the negative selection marker has to be conditional in order to keep the cell alive until the meganuclease variants have the opportunity to cleave. Such a conditional expression can be easily done with a conditional promoter. However, there are other conditional systems that could be used. The meganuclease variants are introduced in an expression cassette. The meganuclease encoding sequence can be operably linked to an inducible promoter or to a constitutive promoter. Of course, the promoter is compatible with the cell used in the assay. If the meganuclease variant has the capacity to cleave the targeted DNA, then the negative selection marker is inactivated, either by deleting the whole negative marker gene or a part thereof (coding sequence or promoter) or by degrading the vector. A culture in a negative selection condition allows the selection of the cell containing the meganuclease variants able to cleave the targeted DNA sequence.

The vector comprising the negative selection marker is preferably transfected before the introduction of the vector encoding the meganuclease variants. Optionally, the vector comprising the negative selection marker can be conserved in the cell in an episomal form. Alternatively, the vector comprising the negative selection marker and the vector encoding the meganuclease variants can be cotransfected into the cell. The cell can be prokaryotic or eukaryotic. Preferably, the prokaryotic cell is E. coli. Preferably, the eukaryotic cell is a yeast cell. The negative selection marker is a protein directly or indirectly toxic for the cell. For example, the negative selection marker can be selected from the group consisting of toxins, translation inhibitors, barnase, and antibiotic for bacteria, URA3 with 5FOA (5-fluoro-orotic acid) medium and LYS2 with a α-AA medium (alpha-adipic acid) for yeast, and thymidine kinase for superior eukaryotic cells. For an example of negative marker selection, see Gruen et al., 2002, Nucleic Acids Research, 30, e29; the disclosure of which is incorporated herein by reference.

If the selection is based on the activation of a positive selection marker, the method involves the use of cell containing an expression vector comprising an inactive positive selection marker and the targeted DNA sequence for the desired meganuclease and an expression vector comprising the library of meganuclease variants. Optionally, the inactive positive selection marker, the targeted DNA sequence and the library of meganuclease variants can be on the same vector (See WO 02/44409). Preferably said expression vector is a plasmid. The meganuclease variants are introduced in an expression cassette. The meganuclease encoding sequence can be operably linked to an inducible promoter or to a constitutive promoter. Of course, the promoter is compatible with the cell used in the assay. For example, the positive selection marker can be an antibiotic resistance (e.g. tetracycline, rifampicin and ampicillin resistance) or an auxotrophy marker for bacteria, TRP1, URA3, or an auxotrophy marker for yeast, and neomycine et puromycine for superior eukaryotic cell. Optionally, the positive selection marker can be an auxotrophy marker compatible with both bacteria and yeast (e.g. URA3, LYS2, TRP1 and LEU2). The inactive positive selection marker gene and the targeted DNA sequence have to be arranged so that the double-strand break leads to a rearrangement of the marker in an active positive marker. Two kinds of repair processes can lead to an active positive selection marker, namely single-strand annealing (SSA) or gene conversion (GC).

The in vivo Single-strand annealing recombination test (SSA) is known by the man skilled in the art and disclosed for example in Rudin et al. (Genetics 1989, 122, 519-534; Fishman-Lobell & Haber (Science 1992, 258, 480-4); Lin et al (Mol. Cell. Biol., 1984, 4, 1020-1034) and Rouet et al (Proc. Natl. Acad. Sci. USA, 1994, 91, 6064-6068); the disclosure of which are incorporated herein by reference.

To test the meganuclease variants, an in vivo assay based on SSA in a cell, preferably a bacterial or yeast cell has been developed. For instance, the method uses a yeast cell. This organism has the advantage that it recombines naturally its DNA via homologous recombination with a high frequency.

This in vivo test is based on the reparation by SSA of a positive selection marker induced by double-strand break generated by an active meganuclease variant. The target consists of a modified positive selection gene with an internal duplication separated by a intervening sequence comprising the targeted DNA sequence. The internal duplication should contain at least 50 bp, preferably at least 200 bp. The efficiency of the SSA test will be increased by the size of the internal duplication. The intervening sequences are at least the targeted DNA sequence. The intervening sequence can optionally comprise a selection marker, this marker allowing checking that the cell has not repaired the positive selection marker by a spontaneous recombination event. The positive selection marker gene is preferably operably linked to a constitutive promoter relating to the cell used in the assay. According to said assay method, the cell will be selected only if a SSA event occurs following the double-strand break introduced by an active meganuclease variant.

Optionally, each vector can comprise a selectable marker to ensure the presence of the plasmid in the cell. The presence of this selectable marker is preferable for the assay performed in yeast cell. For example, for yeast, a first construct comprising the target gene can comprise a Leu2 selectable marker allowing transformed yeast to grow on a synthetic medium that does not contain any Leucine and a second construct can comprise the Trp1 selectable marker allowing transformed yeast to grow on a synthetic medium that does not contain any tryptophane.

The vector comprising the positive selection marker is preferably transfected before the introduction of the vector encoding the meganuclease variants. Optionally, the vector comprising the positive selection marker can be conserved in the cell in an episomal form. Alternatively, the vector comprising the positive selection marker and the vector encoding the meganuclease variants can be cotransfected into the cell.

The in vivo selection of the meganuclease variants can also be performed with a gene conversion assay. For example, the selection vector comprises a first modified positive selection gene with a deletion or a mutation and an insertion of the targeted DNA sequence for the meganuclease at the place of the deletion. The positive selection gene can also be inactivated by the interruption of the gene by an insert comprising the targeted DNA sequence. The selection construct further comprises the segment of the positive selection marker gene which has been deleted flanked at each side by the positive selection marker gene sequences bordering the deletion. The bordering sequences comprise at least 100 bp of homology with the positive selection marker gene at each side, preferably at least 300 pb. The double-stand break generated by an active meganuclease variant in the targeted DNA sequence triggers on a gene conversion event resulting in a functional positive selection marker gene. This kind of assay is documented in the following articles: Rudin et al (Genetics 1989, 122, 519-534), Fishman-Lobell & Haber (Science 1992, 258, 480-4), Paques & Haber (Mol. Cell. Biol., 1997, 17, 6765-6771), the disclosures of which are incorporated herein by reference.

Otherwise, the in vivo selection of the meganuclease variants can be performed through a recombination assay on chromosomic target. The recombination can be based on SSA or gene conversion mechanisms.

A first example based on SSA is the following. A modified positive selection gene with an internal duplication separated by an intervening sequence comprising the targeted DNA sequence for the desired meganuclease variant is introduced into the chromosome of the cell. The internal duplication should contain at least 50 bp, preferably at least 200 bp. The efficiency of the SSA test will be increased by the size of the internal duplication. The intervening sequence is at least the targeted DNA sequence. By transfecting the cell with an expression construct allowing the production of a meganuclease variant in the cell, the repair by homologous recombination of the double-strand break generated by an active meganuclease variant will lead to a functional positive selection marker gene.

Another example based on gene conversion is the following. A mutated non-functional positive selection marker gene comprising the targeted DNA sequence for the desired meganuclease variant is introduced into the chromosome of the cell. Said targeted DNA sequence has to be in the vicinity of the mutation, preferably at less than 1 kb from the mutation, more preferably at less than 500 bp, 200 bp, or 100 pb surrounding the mutation. By transfecting the cell with a fragment of the functional positive selection marker gene corresponding to the mutation area and an expression construct allowing the production of a meganuclease variant in the cell, the repair by homologous recombination of the double-strand break generated by an active meganuclease variant will lead to a functional positive selection marker gene. Alternatively, the fragment of the functional positive selection marker allowing the repair can be integrated on the chromosome. This kind of assay is documented in the following articles: Rouet et al (Mol. Cell. Biol., 1994, 14, 8096-8106); Choulika et al (Mol. Cell. Biol., 1995, 15, 1968-1973); Donoho et al (Mol. Cell. Biol., 1998, 18, 4070-4078); the disclosures of which are incorporated herein by reference.

The selected clones comprise a meganuclease variant presenting the capacity to cleave the targeted DNA sequence. It is preferable to validate the selection by a screening assay. This screening assay can be performed in vivo or in vitro, preferably in vivo.

Optionally, the nucleotide sequences encoding the positively screened meganuclease variants are determined, thereby identifying the meganuclease variants able to cleave the targeted DNA sequence.

In order to perform the screening assay, the selected meganuclease variants need to be cloned and the cleavage assay need to be performed individually for each clone.

The in vivo cleavage assay for the screening is similar to those used for the selection step. It can be based on the inactivation of either a negative selection marker or a reporter gene, or on the activation of either a positive selection marker or a reporter gene.

By reporter gene is intended any nucleic acid encoding a product easily assayed, for example β-galactosidase, luciferase, alkaline phosphatase, green fluorescent protein, tyrosinase, DsRed proteins. The reporter gene is preferably operably linked to a constitutive promoter relating to the cell used in the assay (for example CMV promoter).

Cells used for this screening assay can be prokaryotic, preferably *E. coli*, or eukaryotic, preferably a yeast cell or a mammalian cell. More particularly, it could be interesting to use mammalian cells for a validation of a positive meganuclease variant by an ex vivo cleavage assay.

The recognition and cleavage of the targeted DNA sequence or a part thereof by the meganuclease variants can be assayed by any method known by the man skilled in the art.

One way to test the activity of the meganuclease variants is to use an in vitro cleavage assay on a polynucleotide substrate comprising the targeted DNA sequence or a part thereof. Said polynucleotide substrate could be a synthetic target site corresponding to:

the whole targeted DNA site;
a half targeted DNA site and a half original site; or,
a quarter targeted DNA site and three quarters original site.

Said polynucleotide substrate can be linear or circular and comprises preferably only one cleavage site. The assayed meganuclease variant is incubated with the polynucleotide substrate in appropriate conditions. The resulting polynucleotides are analyzed by any known method, for example by electrophoresis on agarose or by chromatography. If the polynucleotide substrate is a linearized plasmid, the meganuclease activity is detected by the apparition of two bands (products) and the disappearance of the initial full-length substrate band. Preferably, said assayed meganuclease variants are digested by proteinase K, for example, before the analysis of the resulting polynucleotides. For instance, the polynucleotide substrate is prepared by the introduction of a polynucleotide comprising the sequence of the target site in a plasmid by TA or restriction enzyme cloning, optionally followed by the linearization of the plasmid. Preferably, such linearization is not done in the surrounding of the targeted DNA sequence. See Wang et al, 1997, Nucleic Acid Research, 25, 3767-3776; See Examples, Materials & Methods "in vitro activity assays" section) and the characterization papers of the initial homing endonucleases.

Alternatively, such in vitro cleavage assay can be performed with polynucleotide substrates linked to fluorophores, such substrates comprising the targeted DNA sequence. These polynucleotide substrates are immobilized on a solid support. Said solid support is preferably a microplate (96, 384 or 1536 wells). For example, the polynucleotides comprising the targeted DNA sequence present a ligand (such as a biotin) at one end, said ligand allowing the immobilization on a solid support bearing the target of the ligand (for example, streptavidin if biotin is used). The end opposite to the immobilized end is linked to a fluorophore. Cleavage leads to loss of fluorescence by release of the fluorochrome from the solid support.

Otherwise, some in vitro cleavage assays can be based on the fluorescence quenching. A fluorophore (for example, FAM or TAMRA) and a quencher (for example, DABCYL) are located on the polynucleotide substrate such as the quencher inhibits the fluorescence emission. The quenching is abolished when the cleavage by the meganuclease variants occurs on the polynucleotide substrates. Several examples of this quenching assays are detailed in Eisenschmidt et al (2002, Journal of Biotechnology, 96, 185-191) and WO 02/42497, the disclosure of these documents are incorporated herein by reference.

Targeting DNA

In a first embodiment of the above uses according to the invention a targeting fragment of DNA (or targeting DNA) comprising a sequence which modifies the site of interest flanked by sequences sharing homologies to a targeted locus is also introduced, when necessary (see hereafter the Chapter Meganuclease delivery) into the body of said vertebrate (human or non-human). Preferably, homologous sequences of at least 50 bp, preferably more than 100 by and more preferably more than 200 by are used. The sequence which modifies the site of interest can be the correct sequence of a gene for repairing a genetic lesion (gene therapy). Alternatively, it can be any other sequence used to alter the chromosomal DNA in some specific way including a sequence used to modify of a specific sequence, to attenuate or activate an endogenous gene of interest, to inactivate or delete an endogenous gene of interest or part thereof, to introduce a mutation into a site of interest or to introduce an exogenous gene or part thereof. Such chromosomal DNA alterations are used for genome engineering (animal models, protein production) or for anti-viral therapy.

Meganuclease Delivery

The meganuclease can be used either as a polypeptide or as a polynucleotide construct encoding said polypeptide under the control of appropriate transcription regulatory elements including a promoter, for example a tissue specific and/or inducible promoter. Examples of inducible promoters are: eukaryotic metallothionine promoter which is induced by increased levels of heavy metals, prokaryotic lacZ promoter which is induced in response to isopropyl-β-D-thiogalactopyranoside (IPTG) and eukaryotic heat shock promoter which is induced by increased temperature. Examples of tissue specific promoters are skeletal muscle creatine kinase, prostate-specific antigen (PSA), α-antitrypsin protease, human surfactant (SP) A and B proteins, β-casein and acidic whey protein genes. It is introduced into somatic cells of an individual, by any convenient mean well-known to those in the art, alone or in association with either at least an appropriate vehicle or carrier and/or with the targeting DNA.

According to an advantageous embodiment of the uses according to the invention, the meganuclease (polypeptide) is associated with:

liposomes, polyethyleneimine (PEI); in such a case said association is administered and therefore introduced into somatic cells target.

membrane translocating peptides (Bonetta, 2002, *The Sientist*, 16, 38; Ford et al, *Gene Ther*, 2001, 8, 1-4; Wadia & Dowdy, 2002, *Curr Opin Biotechnol*, 13, 52-56); in such a case, there is a fusion with said peptides.

Meganucleases can also be introduced into somatic tissue (s) from an individual according to methods generally known in the art which are appropriate for the particular meganuclease and cell type.

According to another advantageous embodiment of the uses according to the invention, the meganuclease (polynucleotide encoding said meganuclease) and/or the targeting DNA is inserted in a vector. Vectors comprising targeting DNA and/or nucleic acid encoding a meganuclease can be introduced into a cell by a variety of methods (e.g., injection, direct uptake, projectile bombardment, liposomes). Meganucleases can be stably or transiently expressed into cells using expression vectors. Techniques of expression in eukaryotic cells are well known to those in the art. (See Current Protocols in Human Genetics: Chapter 12 "Vectors For Gene Therapy" & Chapter 13 "Delivery Systems for Gene Therapy"). Optionally, it may be preferable to incorporate a nuclear localization signal into the recombinant protein to be sure that it is expressed within the nucleus.

Advantageously, the sequence encoding the meganuclease and the targeting DNA are inserted in the same vector.

A vector which can be used in the present invention includes, but is not limited to, a viral vector, a plasmid, a RNA vector or a linear or circular DNA or RNA molecule which may consists of a chromosomal, non chromosomal, semi-synthetic or synthetic DNA. Preferred vectors are those capable of autonomous replication (episomal vector) and/or expression of nucleic acids to which they are linked (expression vectors). Large numbers of suitable vectors are known to those of skill in the art and commercially available.

Viral vectors include retrovirus, adenovirus, parvovirus (e.g., adenoassociated viruses), coronavirus, negative strand RNA viruses such as orthomyxovirus (e.g., influenza virus), rhabdovirus (e.g., rabies and vesicular stomatitis virus), paramyxovirus (e.g. measles and Sendai), positive strand RNA viruses such as picornavirus and alphavirus, and double stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, Dtype viruses, HTLV-BLV group, lentivirus, spumavirus (Coffin, J. M., Retroviridae: The viruses and their replication, In Fundamental Virology, Third Edition, B. N. Fields, et al., Eds., Lippincott-Raven Publishers, Philadelphia, 1996). Other examples include murine leukemia viruses, murine sarcoma viruses, mouse mammary tumor virus, bovine leukemia virus, feline leukemia virus, feline sarcoma virus, avian leukemia virus, human T-cell leukemia virus, baboon endogenous virus, Gibbon ape leukemia virus, Mason Pfizer monkey virus, simian immunodeficiency virus, simian sarcoma virus, Rous sarcoma virus and lentiviruses. Other examples of vectors are described, for example, in McVey et al., U.S. Pat. No. 5,801,030, the teachings of which are incorporated herein by reference.

Vectors can also comprise selectable markers (for example, neomycin phosphotransferase, histidinol dehydrogenase, dihydrofolate reductase, hygromycin phosphotransferase, herpes simplex virus thymidine kinase, adenosine deaminase, glutamine synthetase, and hypoxanthine-guanine phosphoribosyl transferase for eukaryotic cell culture; TRP1 for S. cerevisiae; tetracycline, rifampicin or ampicillin resistance in E. coli; etc. . . . ).

Once in a cell, the meganuclease and if present, the vector comprising targeting DNA and/or nucleic acid encoding a meganuclease are imported or translocated by the cell from the cytoplasm to the site of action in the nucleus.

Meganucleases and vectors which comprise targeting DNA homologous to the region surrounding the cleavage site and/or nucleic acid encoding a custom-made meganuclease can be introduced into an individual using routes of administration generally known in the art. Administration may be topical or internal, or by any other suitable avenue for introducing a therapeutic agent to a patient. Topical administration may be by application to the skin, or to the eyes, ears, or nose. Internal administration may proceed intradermally, subcutaneously, intramuscularly, intraperitoneally, intraarterially or intravenously, or by any other suitable route. It also may in some cases be advantageous to administer a composition of the invention by oral ingestion, by respiration, rectally, or vaginally.

The meganucleases and vectors can be administered in a pharmaceutically acceptable carrier, such as saline, sterile water, Ringer's solution, and isotonic sodium chloride solution. Typically, for therapeutic applications, the meganucleases will be combined with a pharmaceutically acceptable vehicle appropriate to a planned route of administration. A variety of pharmaceutically acceptable vehicles are well known, from which those that are effective for delivering meganucleases to a site of infection may be selected. The HANDBOOK OF PHARMACEUTICAL EXCIPIENTS published by the American Pharmaceutical Association is one useful guide to appropriate vehicles for use in the invention. A composition is said to be a "pharmaceutically acceptable vehicle" if its administration can be tolerated by the recipient. Sterile phosphate-buffered saline is one example of a pharmaceutically acceptable vehicle that is appropriate for intravenous administration. The mode of administration is preferably at the location of the targeted cells.

The dosage of meganuclease or vector according to the present invention administered to an individual, including frequency of administration, will vary depending upon a variety of factors, including mode and route of administration: size, age, sex, health, body weight and diet of the recipient; nature and extent of symptoms of the disease or disorder being treated; kind of concurrent treatment, frequency of treatment, and the effect desired. For a brief review of pharmaceutical dosage forms and their use, see PHARMACEUTICAL DOSAGE FORMS AND THEIR USE (1985) (Hans Huber Publishers, Berne, Switzerland).

For purposes of therapy, the meganucleases and a pharmaceutically acceptable excipient are administered in a therapeutically effective amount. Such a combination is said to be administered in a "therapeutically effective amount" if the amount administered is physiologically significant. An agent is physiologically significant if its presence results in a detectable change in the physiology of the recipient. In the present context, an agent is physiologically significant if its presence results: in a decrease in the severity of one or more symptoms of the targeted disease, in a genome correction of the lesion or abnormality, or in inhibition of viral infection.

In one embodiment of the uses according to the present invention, the meganuclease is substantially non-immunogenic, i.e., engender little or no adverse immunological response. A variety of methods for ameliorating or eliminating deleterious immunological reactions of this sort can be used in accordance with the invention. In a preferred embodiment, the meganuclease is substantially free of N-formyl methionine. Another way to avoid unwanted immunological reactions is to conjugate meganucleases to polyethylene glycol ("PEG") or polypropylene glycol ("PPG") (preferably of 500 to 20,000 daltons average molecular weight (MW)). Conjugation with PEG or PPG, as described by Davis et al., (U.S. Pat. No. 4,179,337) for example, can provide non-immunogenic, physiologically active, water soluble endonuclease conjugates with anti-viral activity. Similar methods also using a polyethylene-polypropylene glycol copolymer are described in Saifer et al. (U.S. Pat. No. 5,006,333).

Gene Therapy

The use of meganucleases for gene therapy according to the present invention varies depending on the type of genetic disease (monogenic recessive disease, trinucleotide repeats diseases or diseases caused by dominant and compound heterozygous mutations).

Thus, in one embodiment of the present invention, the meganuclease is used in association with a targeting DNA as defined above, comprising a sequence to repair the site of interest, for preventing, improving or curing a monogenetic recessive disease.

In this case, the use of the meganuclease comprises at least the step of (a) inducing in somatic tissue(s) of the individual a double stranded cleavage at a site of interest comprising at least one recognition and cleavage site of said meganuclease, and (b) introducing into the individual a targeting DNA, wherein said targeting DNA comprises (1) DNA sharing homologies to the region surrounding the cleavage site and (2) DNA which repairs the site of interest upon recombination between the targeting DNA and the chromosomal DNA. The targeting DNA is introduced into the individual under conditions appropriate for introduction of the targeting DNA into the site of interest.

Monogenetic recessive diseases include with no limitations diseases affecting the following genes in the corresponding somatic tissues:

liver: apolipoprotein deficiencies (apoA-I or apoB genes); familial hypercholesterolemia (FH; LDL receptor gene); Wilson's disease (WND gene); Sickle cell anemia (hemoglobin beta gene (HBB)); alpha-1 antitrypsin deficiency (alpha-1 antitrypsin gene); Hereditary hemochromatosis (HFE gene); Hemophilia A or B (Factor IX or X genes); Aminoacidopathies (tyrosinemia (fumarylacetoacetate hydrolase gene (FAH)), phenylketonurea (phenylalanine hydroxylase gene (PAH)), . . . ).

Lung: Cystic fibrosis (CFTR:Cystic Fibrosis Transmembrane Regulator)

Muscle: Limb-girdle Muscular Dystrophies ($\alpha$, $\beta$, $\gamma$ or $\delta$-sarcoglycan genes)

Kidney: Polycystic Kidney Disease (PKHDI)

Retina: Retinitis pigmentosa (Rhodopsin gene

Central Nervous system (CNS): Tay-Sachs disease; Lese-Nyhan syndrome (HPRT gene).

In another embodiment of the present invention, the meganuclease is used alone or in association with at least one appropriate vehicle and/or carrier for preventing, improving or curing a trinucleotide repeats disease.

In this case, the trinucleotide repeats ((CGG)n, (CAG)n, or (GAA)n) flanking the meganuclease recognition and cleavage site are deleted by intrachromosomal homologous recombination. More precisely, the use of the meganuclease comprises: inducing in somatic tissue(s) of the individual a double stranded break at a site of interest comprising at least one recognition and cleavage site of said meganuclease under conditions appropriate for chromosomal DNA homologous to the region surrounding the site of cleavage to be deleted into the site of interest and repair of the site of interest (intrachromosomal homologous recombination).

Trinucleotide repeats diseases include with no limitations, diseases affecting the genes as follows:

Fragile X syndrome: CGG repeat, FMR1 gene

Fragile XE syndrome: CCG repeat, FMR2 gene

Friedreich ataxia: GAA repeat, X25 gene

Myotonic dystrophy: CAG repeat, DMPK gene

Huntington disease: CAG repeat, HD gene

Spinocerebellar ataxia: CAG repeat, SCA1,2,3,6,7, and 8 genes

Haw river syndrome: GAA repeat, DRPLA gene.

In yet another embodiment of the present invention, the meganuclease is used alone or in association with a targeting DNA as defined above and/or with at least one appropriate vehicle and/or carrier for preventing, improving or curing genetic diseases caused by dominant or compound heterozygous mutations.

Therefore, there are two cases:

1. Meganuclease used alone: the double-strand break at the site of the mutation is employed to obtain correction of a genetic lesion via a gene conversion event in which the homologous chromosomal DNA sequences from another copy of the gene donates sequences to the sequences where the double-stranded break was induced (interchromosomal homologous recombination). More precisely, the use of the meganuclease comprises: inducing in somatic tissue(s) of the individual a double stranded break at a site of interest comprising at least one recognition and cleavage site of said meganuclease under conditions appropriate for chromosomal DNA homologous to the region surrounding the site of cleavage to be introduced into the site of interest and repair of the site of interest.

2. Meganuclease used in association with a targeting DNA: the use of the meganuclease comprises at least the step of (a) inducing in somatic tissue(s) of the individual a double stranded cleavage at a site of interest comprising at least one recognition and cleavage site of said meganuclease, and (b) introducing into the individual a targeting DNA, wherein said targeting DNA comprises (1) DNA sharing homologies to the region surrounding the cleavage site and (2) DNA which repairs the site of interest upon recombination between the targeting DNA and the chromosomal DNA. The targeting DNA is introduced into the individual under conditions appropriate for introduction of the targeting DNA into the site of interest. The sequence encoding the meganuclease and the sequence encoding the targeting DNA may be carried by the same vector.

According to the present invention, in both cases, said double-stranded cleavage is induced, either in toto by administration of said meganuclease to an individual, or ex vivo by introduction of said meganuclease into somatic cells removed from an individual and returned into the individual after modification.

Genetic diseases caused by dominant or compound heterozygous mutations include with no limitations: Huntington disease, familial hypercholesterolaemia, familial hyperlipidaemia, oro-facio-digital syndrome type 1, dominant otosclerosis, the Bannayan syndrome, hailey-hailey disease, achondroplasia.

Antiviral Therapy

According to the present invention meganucleases are used as therapeutics in the treatment of viral diseases caused by viruses or retroviruses that present a DNA intermediate. Indeed, many viruses which infect eukaryotic cells possess, during at least one part of their life cycle, genomes that consist of double stranded DNA which can be cleaved readily by a meganuclease. This strategy involves identification of DNA sequences within the viral genome that are viral-specific, i.e., they are not present within the human genome. Once identified, meganucleases that specifically bind and cleave such sequences with high affinity and specificity can be designed using the method for preparing custom-made meganucleases as described in the present invention. Then the designed meganucleases are used for the treatment of viral infection.

Meganucleases or expression vector encoding said meganucleases are introduced into the individual by any convenient mean. When the custom-made meganucleases are introduced or expressed into the infected cells, the virus is inactivated and/or deleted. The meganuclease treatment has no functional impact on healthy cells. Similarly, such antiviral therapy based on the use of at least one meganuclease could be used to treat organs of an animal dedicated to xenotransplantation.

Any virus that contains a double stranded DNA stage in its life cycle can be targeted for deletion or inactivation by creating a meganuclease that recognizes DNA sequences specific of the viral genome. These viruses could be in replicative or latent form. They could stay either episomal or integrated in the host's genome.

The double stranded DNA genome viruses are well appropriate to be treated by using meganucleases as defined in the present invention. Among them are found the adenoviruses, the herpesviruses, the hepadnaviruses, the papovaviruses, and the poxviruses. Among the herpesviruses are found herpes simplex virus (HSV), varicella virus (VZV), Epstein-Barr virus (EBV), cytomegalo virus (CMV), herpes virus 6, 7 and 8. Among the hepadnaviruses are found the human hepatitis B virus (HBV). Among the papovariruses are found papillomavirus (HPV) (i.e. HPV16 or HPV18) and polyoma virus. Among the adenoviruses are found adenovirus 11 and 21 which are involved in acute hemorrhagic cystitis.

The retroviruses are also well appropriate to be treated by using meganucleases according to the present invention. Although they are RNA viruses, they are integrated in the host genome as double-stranded DNA form. Among the retroviruses are found the human immunodeficiency virus (HIV) and the human T lymphoma virus (HTLV) (i.e. HTLV1).

According to an advantageous embodiment of the use according to the present invention, said virus is selected from HIV, HBV, HTLV, HPV and HSV.

Several above-mentioned viruses are well-known to be involved in carcinogenesis: EBV in Burkitt's lymphoma, other lymphoproliferative disease and nasopharyngeal carcinoma; herpes virus 8 in Kaposi sarcoma; HBV in hepatocellular carcinoma; HPV in genital cancer; HTLV-1 in T-cell leukemia.

For episomal viruses, a double-strand break introduced in its genome leads to the linearisation of the genome and its degradation. Examples of episomal viruses are HSV-1, EBV, and HPV.

For integrated viruses, a double strand break introduced in or near the integrated viral sequence leads to partial or complete deletion of the integrated viral sequence. Examples of integrated viruses are HPV, HTLV, HBV, and HIV. Several mechanisms could be involved in the deletion. A double-strand break in a chromosome induces a gene conversion with the homologous chromosome, therefore leading to viral sequence deletion. If directed repeat sequences are present near the double strand break, the break could also be repaired by SSA (single strand annealing) leading to partial or complete viral deletion. If two double-strand breaks are introduced, then the chromosome could also be repaired by end joining leading to partial or complete deletion of the virus, depending on the positions of the double-strand breaks. See Example 5 in U.S. Pat. No. 5,948,678, the disclosure of which is incorporated herein by reference.

To ensure that the targeted viral DNA sequences are not present in the host's genome, such DNA target sequences should be at least 15 nucleotides in length and preferably at least 18 nucleotides in length. As the homing endonuclease present a recognition sequence spanning to 12-40 bp, this condition is fulfilled with the custom-made meganucleases as defined in the present invention. More particularly, I-Cre I homing endonuclease has a 22 by recognition sequence.

Any DNA sequence of viral genomes can be targeted for cleavage by meganucleases as defined in the present invention. Preferred target sites include those sequences that are conserved between strains of virus and/or which genes are essential for virus propagation or infectivity. These positions are preferable for at least two reasons. First, essential parts of viruses are less mutated than others. Secondly, it is preferably to target an essential region of the virus to maximize the inactivation of the virus.

A good target for the custom-made meganuclease could be the viral origin of replication (ori) and/or the viral gene encoding an on binding protein. Examples of on binding proteins include the HSV-1 UL9 gene product, the VZV gene 51 product, the human herpesvirus 6B CH6R gene product, the EBV EBNA-1 gene product and the HPV E1 and E2 gene products. Other interesting targets for HPV are the genes E6 and E7 as products of which are involved in the initiation and maintenance of the proliferative and malignant phenotype. A preferred target is the highly conserved 62 nucleotides sequence in the pre-core/core region of HPV (E6, E7). Examples of interesting targets for EBV are the genes EBNA and LMP. It could be interesting to target the gene Tax of HTLV-1 which appears to mediate the oncogenic effects of the virus. For HBV, an interesting target could be the X gene as the X protein interacts with elements of the DNA repair system and may increase the mutation rate of p53. For HIV, a preferred target is within TAT, REV, or TAR genes. The viral targets are not limited to the above-mentioned examples. Optionally, the target DNA could be located in the viral repeated sequences such as ITR (Inverted Terminal Repeat) and LTR (Long Terminal Repeat).

Preferably, at least two different targeted sites are used. Indeed, as the main protection of the viruses is their ability to mutate. Therefore, two targeted sites avoid the virus to escape the treatment by using the custom-made meganucleases, according to the present invention. Moreover, the successive use of different custom-made meganucleases may avoid the adverse immunologic response. Said different custom-made meganuclease can present different initial meganucleases, therefore different immunogenicities.

The effectiveness of a meganuclease to inhibit viral propagation and infection is preferably assessed by in vitro and in vivo assays of infection. Such assays can be carried out first in cell culture to establish the potential of different meganucleases to cleave a viral DNA in a way that deleteriously affects viral propagation. Preliminary studies of this type are followed by studies in appropriate animal models. Finally, clinical studies will be carried out.

Different viruses require different assay systems, since hosts and culture conditions suitable to different viruses vary greatly. However, such appropriate conditions have been described for culturing many viruses and these conditions can be used to test the effect of exposing virus and/or host to meganucleases to determine the ability of the endonuclease to inhibit viral infection. For one discussion of culture conditions for specific viruses see Chapter 17 in Fields and Knipe, Eds., FIELDS VIROLOGY, 2nd Ed., Raven Press, N.Y. (1990).

A host and/or virus can be exposed at various times during a course of infection, under varying conditions, in several amounts, and in a variety of vehicles, to mention just a few relevant parameters that can be varied, to assess the potential of meganuclease to achieve a potentially therapeutic effect.

In addition, in order to tests ex vivo in cultured cells, potential therapeutical meganuclease can be tested in animal models to assess prophylactic, ameliorative, therapeutic and/or curative potential, either alone or in conjunction with other therapeutic agents. In some cases, it will not be possible to culture a virus and it will be necessary to perform all biological assays in animal models. It will be readily appreciated that different animal models will be appropriate to different viruses. Any animal model, however, can be used to assess the therapeutic potential of a meganuclease.

A potentially effective dose of the assayed meganucleases may be administered to a suitable population of animals, and the effect of the meganucleases on the course of a viral infection may be assessed by comparison with an appropriate control. Such methods for assessing pharmacological effect are well known in the art and can readily be adapted to determining the therapeutic profile of the meganucleases.

Genome Engineering

Genome engineering is the set of methods used to induce a change in the genetic program of a living cell and/or organism. The meganucleases obtained by the method of the present invention allows rational site directed modifications of cell genomes. The purpose of these techniques is to rewrite chromosomes precisely where they should be modified leaving the rest of the genome intact. Fields of applications of the genome engineering are multiple: animal models generation (knock-in or knock-out), protein production (engineering of production strains, protein production in plant and animals for protein production in milks), agricultural biotechnology (addition or removal of a trait, marker excision), modification and study of metabolic pathway.

In a first embodiment of the use according to the present invention, it comprises at least the following steps: 1) introducing a double-strand break at the genomic locus comprising at least one recognition and cleavage site of said meganuclease; 2) providing a targeting DNA construct comprising the sequence to be introduced flanked by sequences sharing homologies to the targeted locus. Indeed, shared DNA homologies are located in regions flanking upstream and downstream the site of the break in the targeting DNA construct and the DNA that might be introduced should be located between the two arms. Said meganuclease can be provided directly to the cell or through an expression vector comprising the polynucleotide sequence encoding said meganuclease and suitable for its expression in the used cell. This strategy is used to introduce a DNA sequence at the target site, for example to generate knock-in animal models or cell lines that can be used for drug testing or the production of proteins.

In another embodiment of the use according to the present invention it comprises at least the following steps: 1) introducing a double-strand break at the genomic locus comprising at least one recognition and cleavage site of said meganuclease; 2) maintaining under conditions appropriate for homologous recombination with the chromosomal DNA homologous to the region surrounding the cleavage site. This strategy is used to delete a DNA sequence at the target site, for example to generate knock-out animal models for functional genomic studies or for the generation of appropriate animal models for drug testing. Additionally, knock-outs can be used for the improvement or optimization of cell lines including the modification of metabolic pathways or the generation of cell lines for drug testing.

BRIEF DESCRIPTION OF THE DRAWINGS

The present invention will be further illustrated by the additional description and drawings which follows, which refers to examples illustrating the use of meganucleases for inducing homologous recombination in somatic tissues according to the invention. It should be understood however that these examples are given only by way of illustration of the invention and do not constitute in anyway a limitation thereof FIG. 1 discloses the amino acid sequence of a single chain I-Cre I meganuclease and one polynucleotide encoding said single chain meganuclease. In the protein sequence, the two first N-terminal residues are methionine and alanine (MA), and the three C-terminal residues alanine, alanine and aspartic acid (AAD). These sequences allow having DNA coding sequences comprising the NcoI (CCATGG) and EagI (CGGCCG) restriction sites, which are used for cloning into various vectors.

FIG. 2 discloses polynucleotide sequences. FIG. 2A discloses a polynucleotide called "Natural" encoding the I-Cre I homing endonuclease. FIG. 2B discloses a polynucleotide sequence called "Non homologous" encoding the I-Cre I homing endonuclease. FIG. 2C discloses a polynucleotide sequence called "Template" encoding the I-Cre I homing endonuclease comprising the mutation D75NJ. Each I-Cre I homing endonuclease has two additional amino acids (MA) at the N terminal end and three additional amino acids (AAD) at the C-terminal ends. FIG. 2D discloses the polynucleotide sequences of the primers, called UlibIfor, UlibIrev, UlibIIfor, and UlibIIrev, used for the generation of the libraries UlibI and UlibII.

FIG. 5: COS cells monolayers were transfected with vector expressing I Sce-I (B) or with control plasmid (A). Fourty eight (48) hours after transfection cells were infected with rHSV-1 (30 PFU). Two days later monolayer was fixed and stained (X-Gal). Infected cells appeared in blue.

FIG. 6.

FIG. 7.

DNA concentrations. I-Sce-I refers to vector expressing I-Sce I; I-Sce I(−) refers to a vector in which ORF of 1-Sce I was inserted in reverse orientation; negative control refers to control plasmid.

Figure 8:
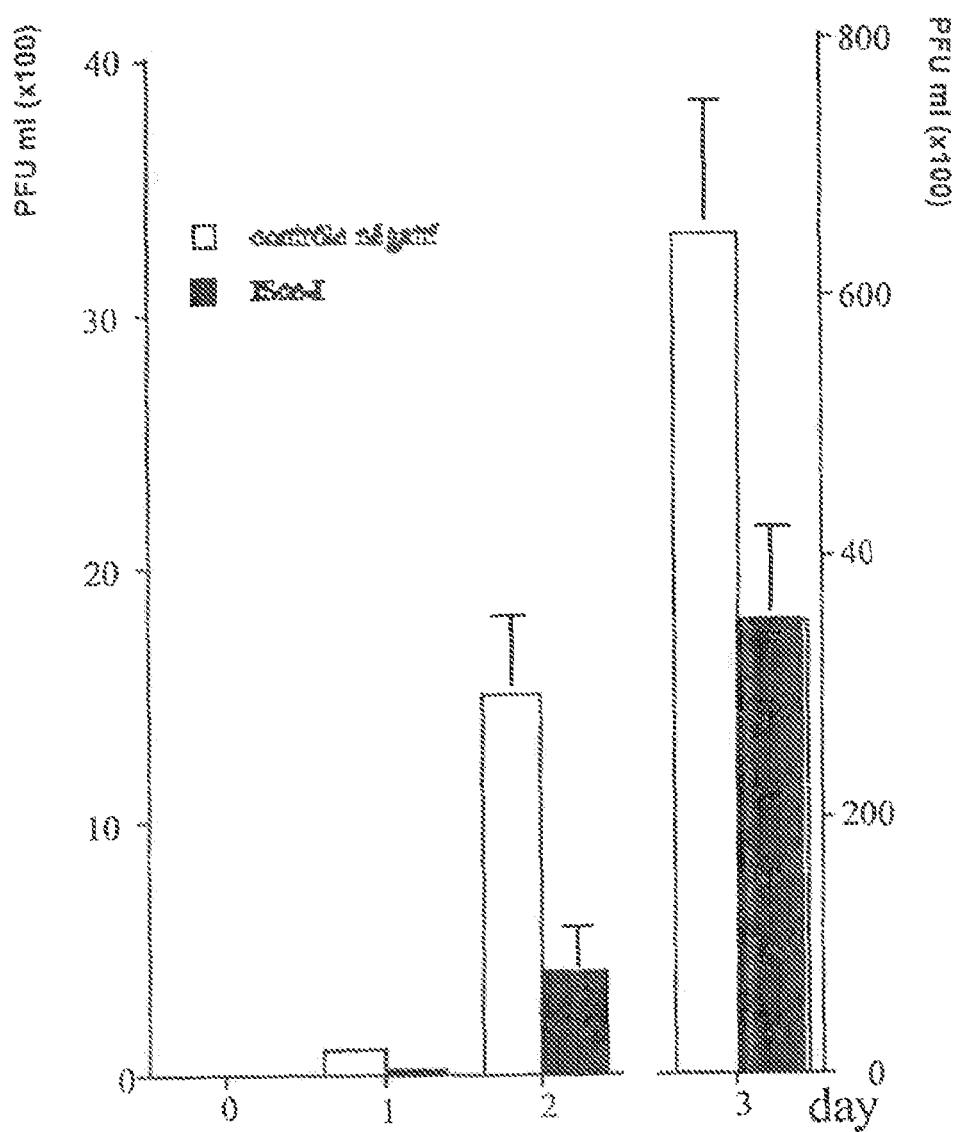

FIG. 8 illustrates the titration of the virus released in the medium after infection of the transfected cells. Every day, medium was collected and fresh medium was added. Viruses were measured by standard plaque assay. I-Sce I refers to vector expressing I-SceI; I-Sce I(−) refers to a vector in which ORF of I-Sce I was inserted in reverse orientation; negative control refers to control plasmid.

FIG. 9 represents the I-CreI DNA target and five related targets. (C1234=SEQ ID NO: 10; C1221=SEQ ID NO: 11; C4334=SEQ ID NO: 12; H1234=SEQ ID NO: 13; H1221=SEQ ID NO: 14; H4334=SEQ ID NO: 15). Conserved positions are in grey boxes.

Figure 10:
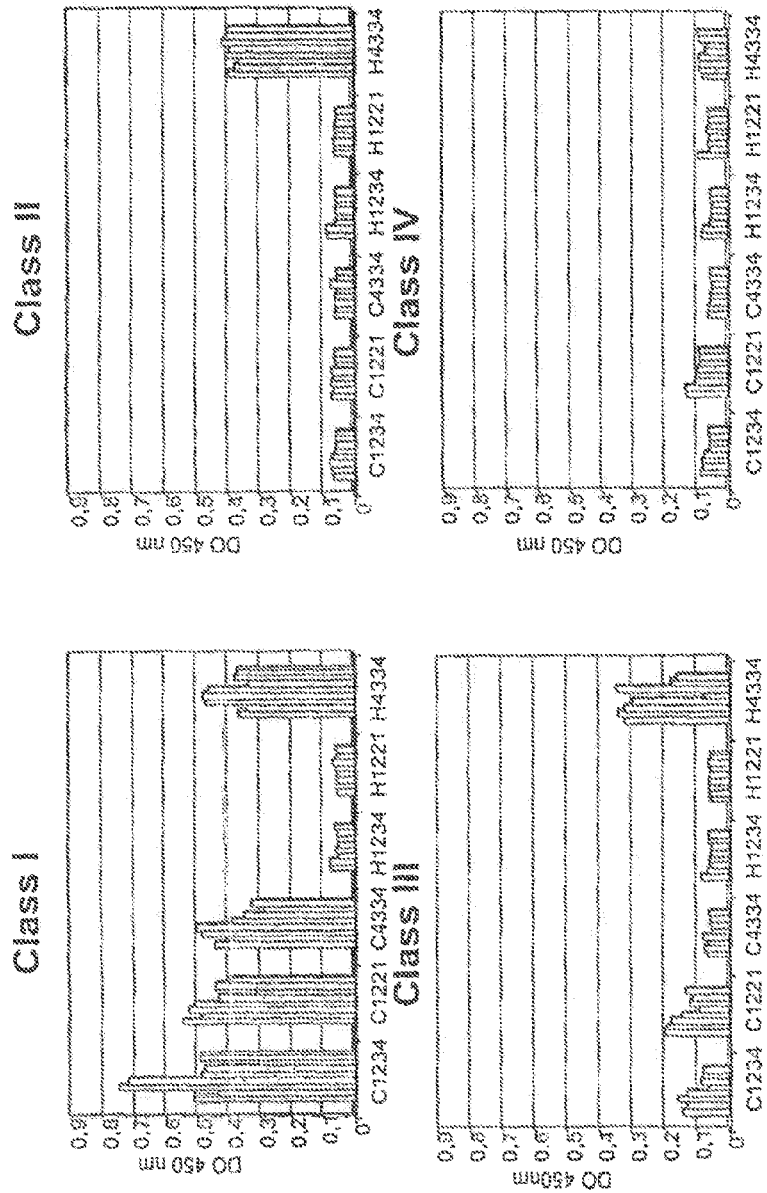

FIG. 10 illustrates four binding patterns obtained after screening of the Lib2 library with six targets. Positives were identified in a first screen and confirmed in a second one during which they were assayed eight times (corresponding to the eight solid bars) on each of the targets (C1234, C1221, C4334, H1234, H1221 and H4334). Histograms are shown for one clone from each class. Targets are described in FIG. 9.

Figure 11:
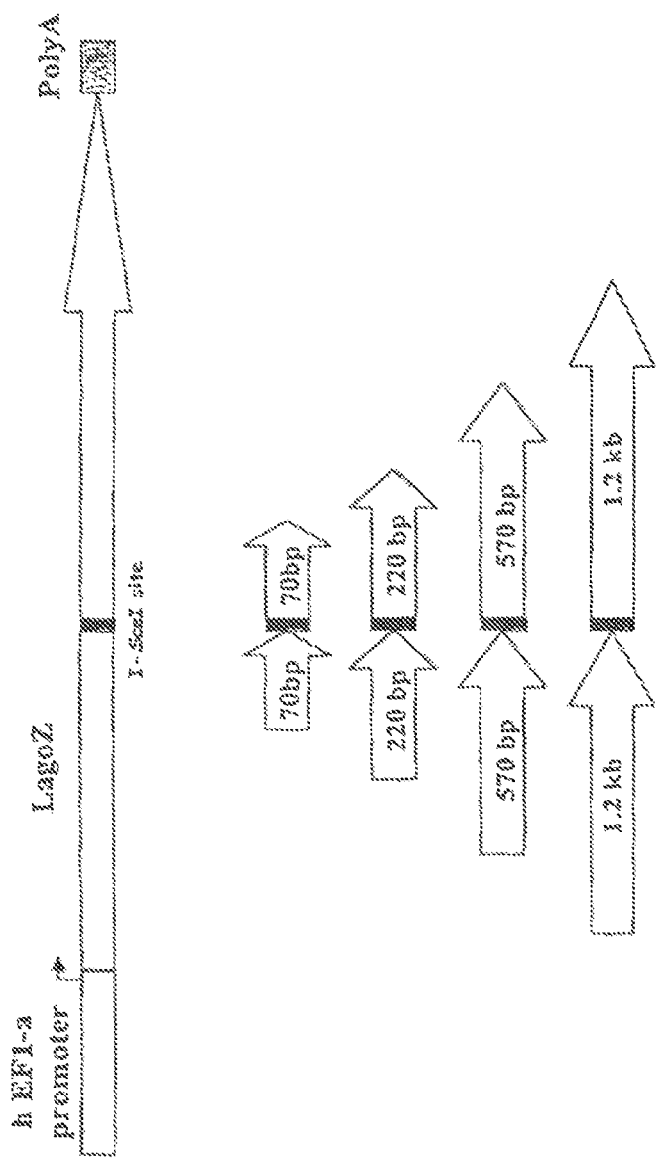

FIG. 11 illustrates the schematic representation of the target vectors. The CpG depleted LacZ gene (LagoZ) is driven by the human elongation factor 1 alpha promoter. The LagoZ gene is inactivated by the insertion of I-SceI cleavage site. Flanking repeats are represented by open arrows. The length of the homologous sequences are indicated in bold.

Figure 12:
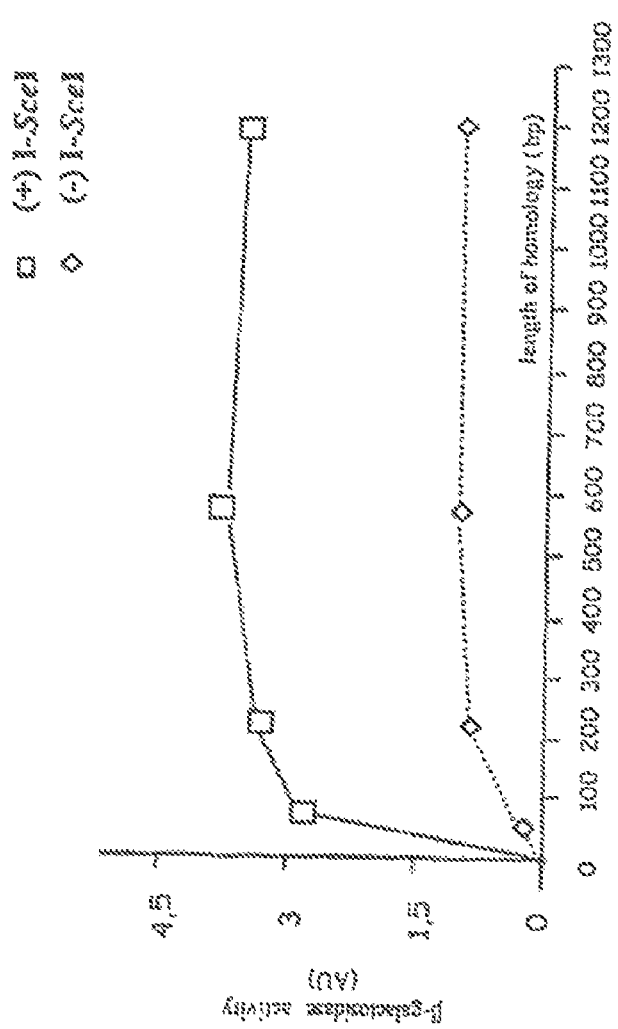

FIG. 12 illustrates the effect of the length of homology on single strand annealing (SSA) efficiency. Cells monolayers were transfected with equimolar amounts of target plasmid bearing different lengths of homologous repeat sequences and vector expressing ISce-I or with control plasmid. Seventy-two hours after transfection cells were collected and β-galactosidase activity was quantified in cell lysates. (+)I-SceI, cotransfection with vector expressing I-SceI; (−)I-SceI, cotransfection with expression vector where the ORF of I-SceI was inserted in the reverse orientation.

Figures 13A, 13B:
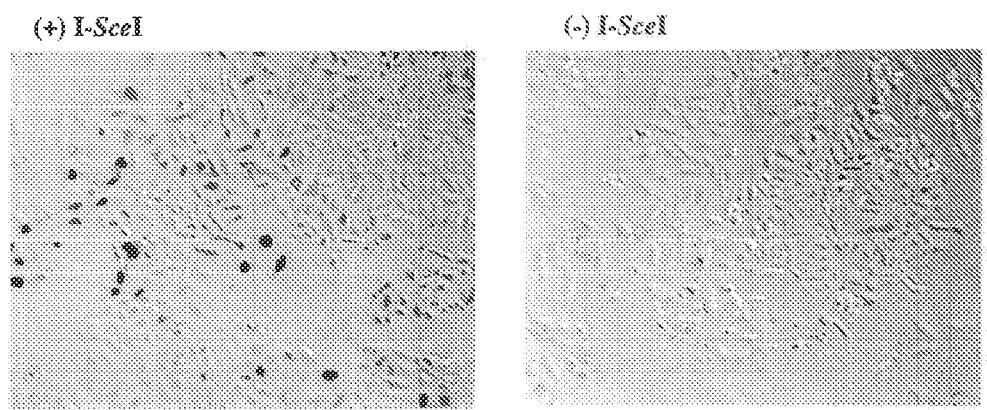

FIG. 13: Cell monolayers were cotransfected with a vector expressing (+)I-SceI or with a control plasmid (−)I-SceI Seventy-two hours after transfection cells were fixed and stained (X-Gal). FIG. 13A: cells where gene repair took place appeared in dark. FIG. 13B: frequency of I-SceI induced recombination on 70 and 220 by duplication target vectors. The frequency is calculated by the ratio of blue cells/transfected cells.

Figure 14A:
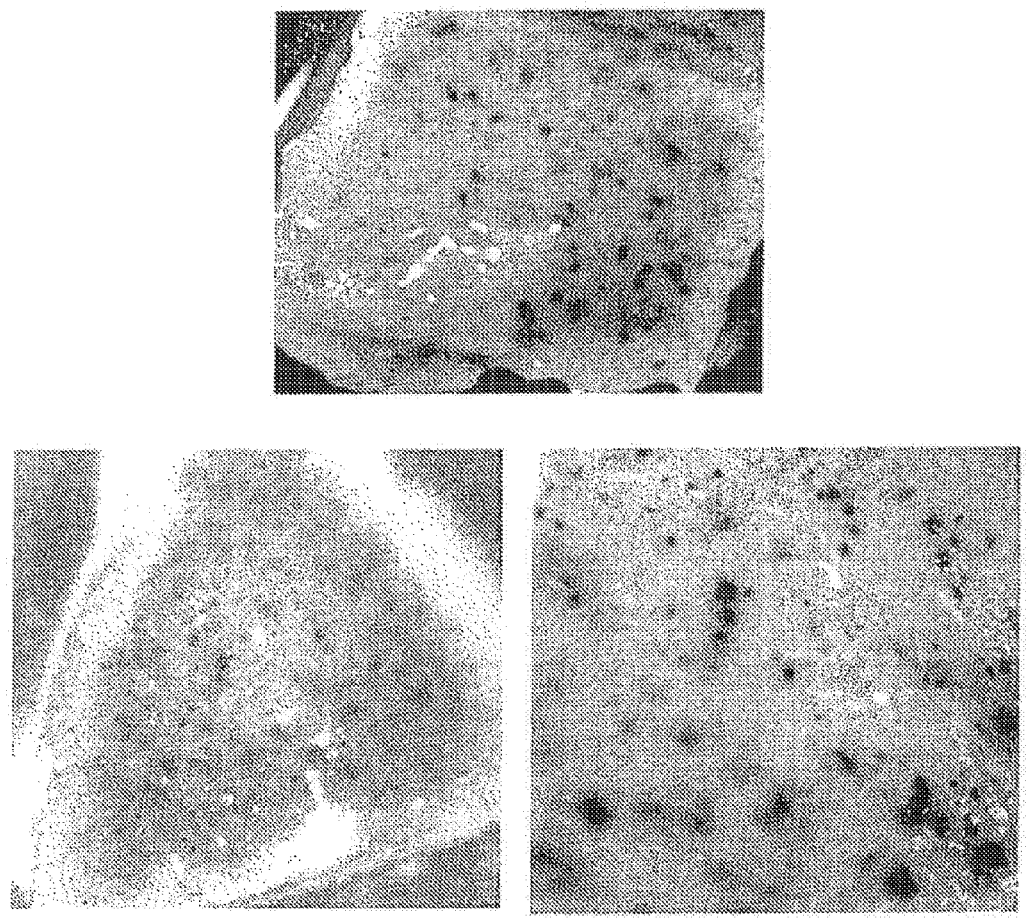
Figure 14B:

FIG. 14A: X-Gal staining of liver from mice injected with a mixture of the target LagoZ gene (30 μg) and an I-SceI expression vector (10 μg). FIG. 14B: X-Gal staining of liver from mice injected with a mixture of the target LagoZ gene (30 μg) and an expression vector where the ORF of I-SceI was inserted in the reverse orientation (10 μg).

FIG. 15: X-Gal staining of the liver of hemizygote transgenic mice of two independent strains infected with the <<Ad.I-SceI>> adenovirus by IV. A. Five days post-infection, β-galactosidase activity is detected in multiple cells of the entire liver of $10^{10}$ infectious units infected <<58A>> hemizygote. In contrast, no β-galactosidase activity could be detected by X-Gal staining of the livers of <<Ad.control>>-infected hemizygote or un-infected <<58A>> littermates (data not shown). B. and C. Fourteen days post-infection, β-galactosidase activity is detected in multiple cells of the entire liver of $10^9$ infectious units infected mouse (B) and $10^{10}$ infectious units infected mouse (C). Stronger signal is detected in C compared to B, probably because of the bigger number of cells that were infected with the <<Ad.I-SceI>>. In contrast, no β-galactosidase activity could be detected by X-Gal staining of the livers of un-infected <<361>> littermates (data not shown).

Figure 16:
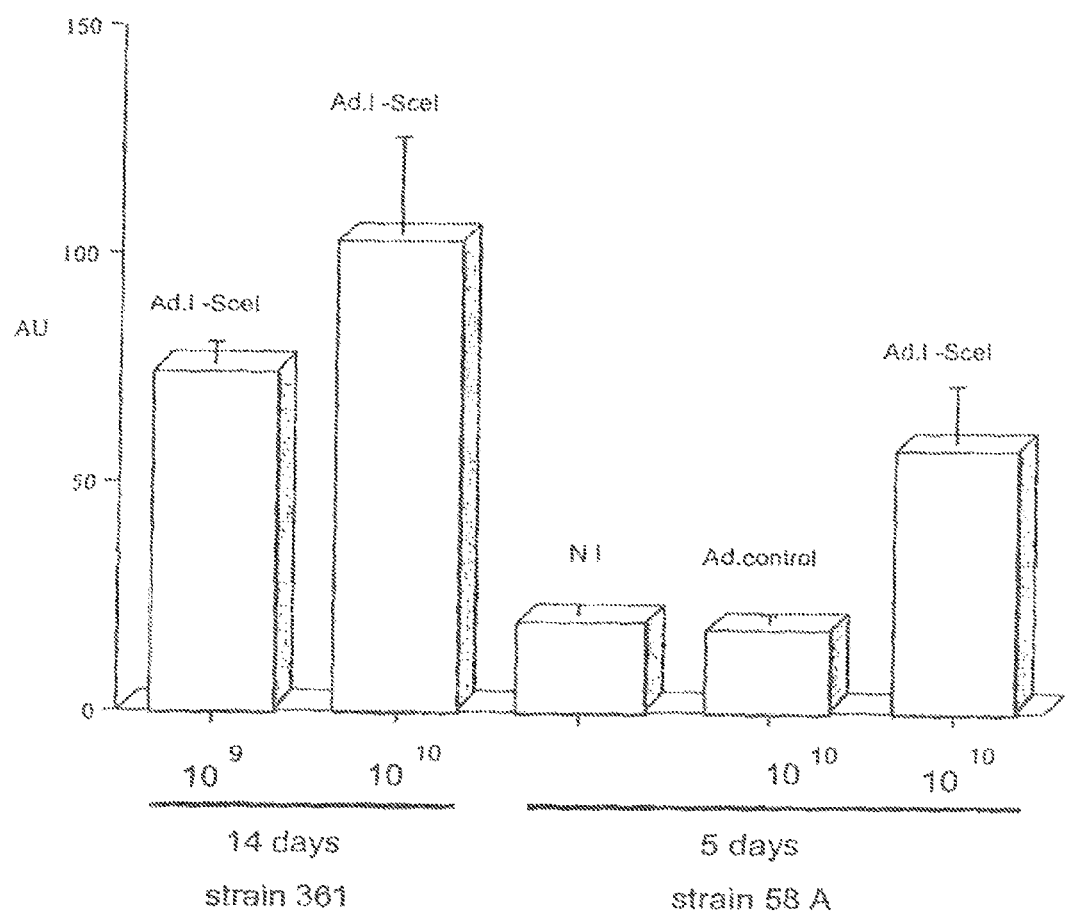

FIG. 16: Fluorescent β-galactosidase assay on liver extract. Two independent strains of transgenic mice (58 A and 361) were injected with $10^9$ or $10^{10}$ PFU of adenovirus expressing I-SceI (Ad.I-SceI) or control virus (Ad.control). Mice were sacrificed 5 or 14 days post injection, liver was dissected and protein were extracted. 30 μl of liver protein extract were incubated at 37° C. in presence of Fluorescein digalactoside (FDG). Bars represent the standard deviation of the assay (two measure experiments with samples of the same extracts). NI, non injected mice; Ad.I-SceI, mice injected with adenovirus expressing I-SceI; Ad.control, mice injected with control adenovirus.

Figure 17:
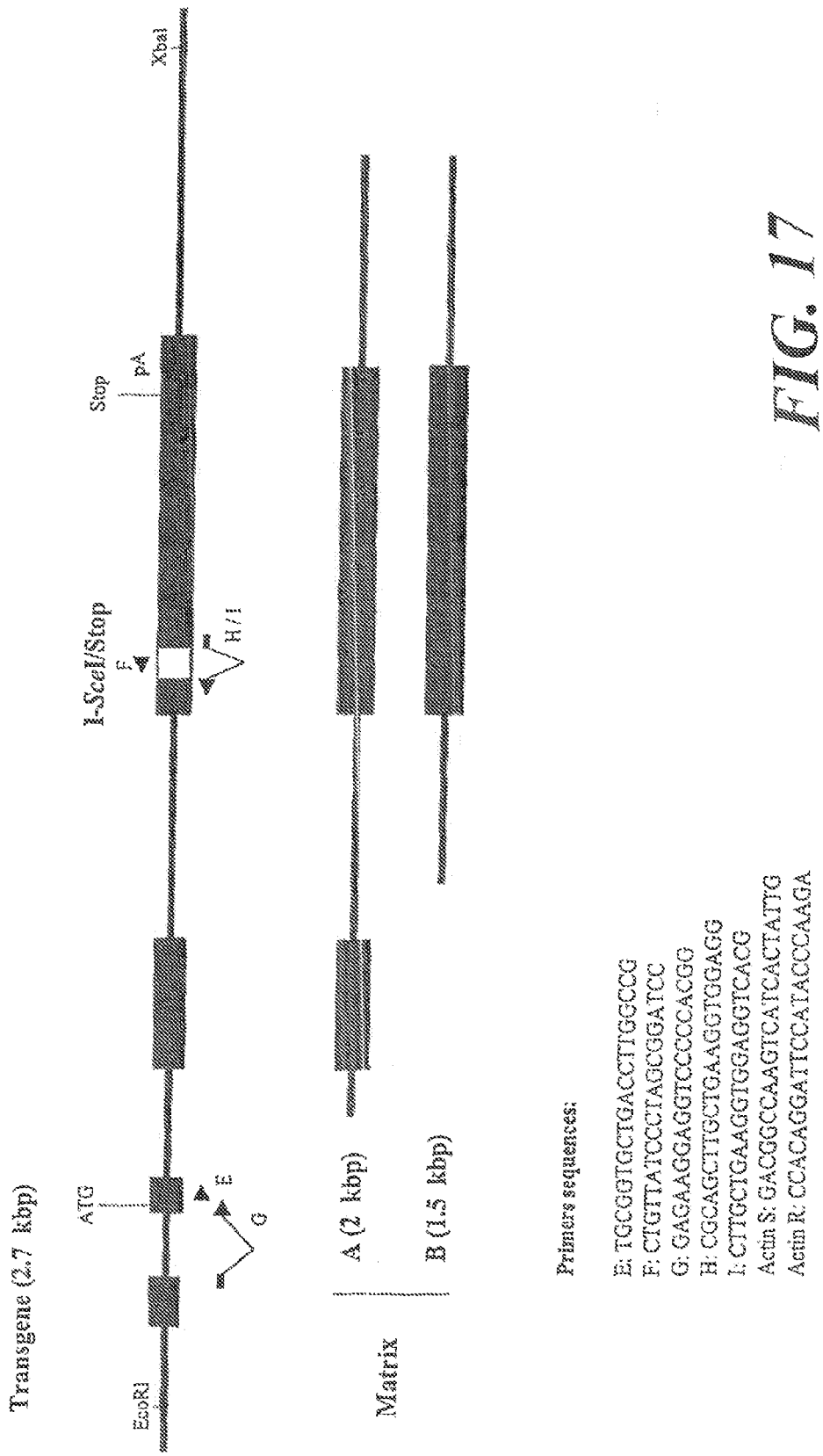

FIG. 17 represents the transgene, the DNA repair matrix and the sequences of the primers used in example 7. (E=SEQ ID NO: 16; F=SEQ ID NO: 17; G=SEQ ID NO: 18; H=SEQ ID NO: 19; I=SEQ ID NO: 20; Actin S=SEQ ID NO: 21; Actin R=SEQ ID NO: 22)

Figure 18:
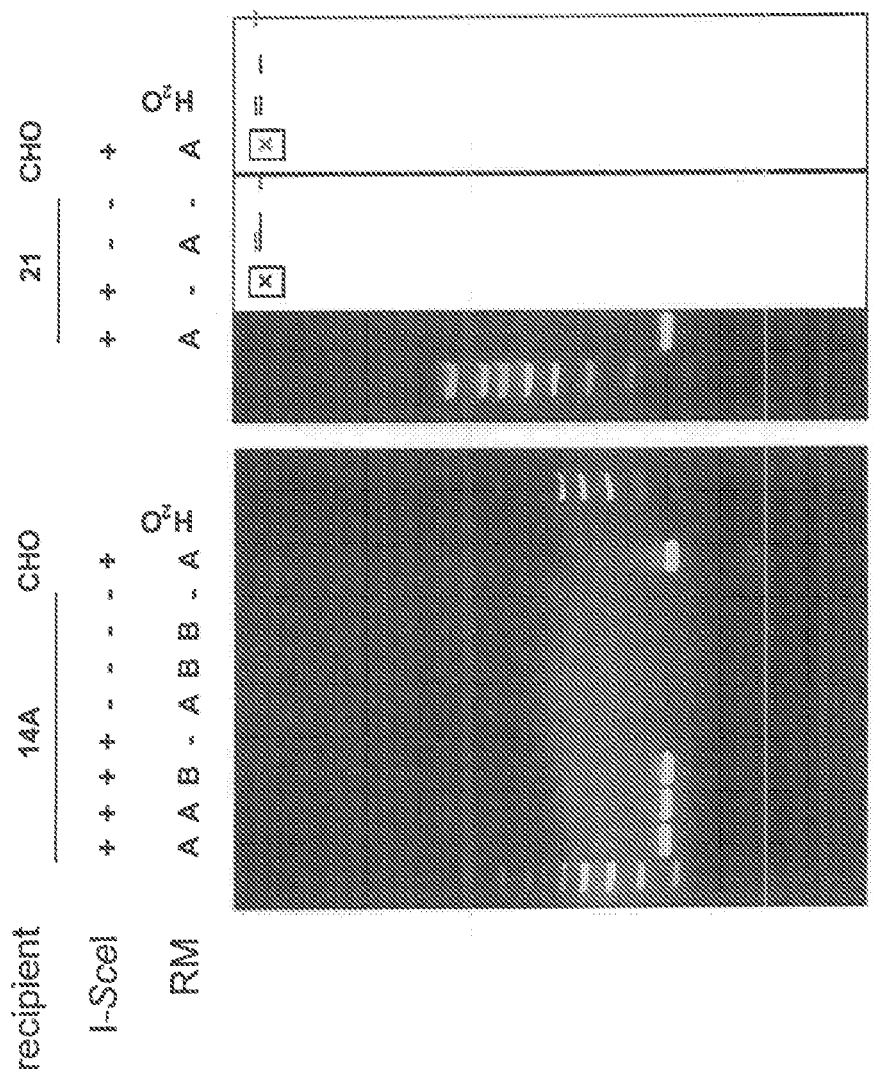

FIG. 18 illustrates the RT-PCR analysis of I-SceI-hApo A-I transgene repair by I-SceI induced gene conversion in mice. Hydrodynamic tail vein injection of naked DNA (I-SceI expression vector and DNA repair matrix) in 3 to 4 weeks old transgenic mice (line 14A and 21). A: 2 kbp DNA repair matrix (RM) and B: 1.5 kbp RM. I-SceI induced gene conversion on I-SceI-hApo A-I transgene in CHO cells was used as PCR positive control.

EXAMPLES

Example 1

Single Chain Meganuclease Derived from Dimeric Homing Endonucleases

Some LAGLIDADG (SEQ ID NO: 24) homing endonucleases are active as homodimer. Each monomer mainly dimerizes through their dodecapeptide motifs. A single-chain meganuclease can be engineered by covalently binding two monomers modified such as to introduce a covalent link between the two sub-units of this enzyme. Preferably, the covalent link is introduced by creating a peptide bond between the two monomers. However, other convenient covalent links are also contemplated. The single-chain meganuclease preferably comprises two subunits from the same homing endonuclease such as single-chain I-Cre I and single-chain I-Ceu I. A single-chain meganuclease has multiple advantages. For example, a single-chain meganuclease is easier to manipulate. The single-chain meganuclease is thermodynamically favored, for example for the recognition of the target sequence, compared to a dimer formation. The single-chain meganuclease allows the control of the oligomerisation.

A single chain version of I-CreI (scI-CreI) was modeled and engineered. scI-CreI cleaves its cognate DNA substrate in vitro and induces homologous recombination both in yeast and mammalian cells.

Design of the Single Chain I-CreI Meganuclease

I-CreI from *Chlamydomonas reinhardtii* is a small LAGLIDADG (SEQ ID NO: 24) homing endonuclease that dimerizes into a structure similar to that of larger monomer LAGLIDADG (SEQ ID NO: 24) homing endonuclease. To engineer a single chain version of I-CreI (scI-CreI), two I-CreI copies were fused. This required placing a linker region between the two domains, and a significant part of the I-CreI protein had to be removed at the end of the domain preceding the linker.

The three-dimensional structure of I-DmoI is comparable to that of I-CreI, with the exception that I-DmoI comprises a linker region that leads from one apparent domain to the other. The boundary of that linker finely matches related main chain atoms of the I-CreI dimer. In the first domain, residues 93 to 95 from the third α-helices of I-CreI and I-DmoI (prior to the linker) are structurally equivalent. At the beginning of the second LAGLIDADG (SEQ ID NO: 24) α-helix (second domain), I-DmoI residues 104 to 106 correspond to I-CreI residues 7 to 9. In addition, Leu95 and Glu105 from I-DmoI have conserved identities in I-CreI, and I-DmoI residue Arg104 aligns with another basic residue in I-CreI (Lys7). Thus, the single chain I-CreI (scI-CreI), was designed by inserting the I-DmoI linker region from residue 94 to 104 (sequence MLERIRLFNMR (SEQ ID NO: 26)) between a first I-CreI domain (terminated at Pro93) and a second I-CreI domain (starting at Glu8).

Detailed structural analysis of how the new linker connects the scI-CreI protein domains (in a modeled structure) revealed no potential incompatibility. For example, the side chains of nonpolar amino acids taken from I-DmoI, Met94, Ile98 and Phe109 point inside fitting cavities of I-CreI. A single mutation was made (P93A), however, to promote regularity of the backbone in the α-helix prior to the linker region. (See FIG. 1 for amino acids and polynucleotide sequences).

Materials and Methods

Protein Expression and Purification

His-tagged proteins were over-expressed in *E. coli* BL21 (DE3) cells using pET-24d (+) vectors (Novagen). Induction with IPTG (1 mM), was performed at 25° C. Cells were sonicated in a solution of 25 mM HEPES (pH 8) containing protease inhibitors (Complete EDTA-free tablets, Roche) and 5% (v/v) glycerol. Cell lysates were centrifuged twice (15 000 g for 30 min). His-tagged proteins were then affinity-purified, using 5 ml Hi-Trap chelating columns (Amersham) loaded with cobalt. Several fractions were collected during elution with a linear gradient of immidazole (up to 0.25M immidazole, followed by plateau at 0.5M immidazole and 0.5M NaCl). Protein-rich fractions (determined by SDS-PAGE) were concentrated with a 10 kDa cut-off centriprep Amicon system. The resulting sample was eventually purified by exclusion chromatography on a Superdex75 PG Hi-Load 26-60 column (Amersham). Fractions collected were submitted to SDS-PAGE. Selected protein fractions concentrated and dialyzed against a solution of 25 mM HEPES (pH 7.5) and 20% (v/v) glycerol.

In Vitro Cleavage Assays pGEM plasmids with single meganuclease DNA target cut sites were first linearized with XmnI. Cleavage assays were performed at 37° C. or 65° C. in 12.5 mM HEPES (pH 8), 2.5% (v/v) glycerol and 10 mM MgCl2. Reactions were stopped by addition of 0.1 volume of 0.1 M Tris-HCl (pH 7.5), 0.25 M EDTA, 5% (w/v) SDS, and 0.5 mg/ml proteinase K and incubation at 37° C. for 20 minutes. Reaction products were examined following separation by electrophoresis in 1% agarose gels.

Yeast Colorimetric Assay.

The yeast transformation method has been adapted from previous protocols. For staining, a classic qualitative X-Gal Agarose Overlay Assay was used. Each plate was covered with 2.5 ml of 1% agarose in 0.1 M Sodium Phosphate buffer, pH 7.0, 0.2% SDS, 12% Dimethyl Formamide (DMF), 14 mM β-mercaptoethanol, 0.4% X-Gal, at 60°. Plates were incubated at 37° C.

Mammalian Cells Assays

COS cells were transfected with Superfect transfection reagent accordingly to the supplier (Qiagen) protocol. 72 hours after transfection, cells were rinsed twice with PBS1X and incubated in lysis buffer (Tris-HCl 10 mM pH7.5, NaCl 150 mM, Triton X100 0.1%, BSA 0.1 mg/ml, protease inhibitors). Lysate was centrifuged and the supernatant used for protein concentration determination and β-galactosidase liquid assay. Typically, 30 µl of extract were combined with 3 µl Mg 100× buffer (MgCl$_2$ 100 mM, β-mercaptoethanol 35%), 33 µl ONPG 8 mg/ml and 234 µl sodium phosphate 0.1M pH7.5. After incubation at 37° C., the reaction was stopped with 500 µl of 1M Na$_2$CO$_3$ and OD was measured at 415 nm. The relative β-galactosidase activity is determined as a function of this OD, normalized by the reaction time, and the total protein quantity.

Results: Single Chain I-CreI Cleaves its DNA Substrate In Vitro and in Living Cells A synthetic gene corresponding to the new enzyme was engineered and the scI-CreI protein over-expressed in *E. coli*. The ability of purified scI-CreI to cleave DNA substrates in vitro was tested, using linearized plasmids bearing a copy of the I-CreI homing site. Similarly to parent I-CreI, the novel enzyme cleaves an I-CreI target site at 37° C.

In order to test the functionality of scI-CreI in vivo, an assay to monitor meganuclease-induced homologous recombination in yeast and mammalian cells was designed. In yeast, *Xenopus* oocytes and mammalian cells, DNA cleavage between two direct repeats is known to induce a very high level of homologous recombination between the repeats. The recombination pathway, often referred to as Single-Strand Annealing (SSA), removes one repeat unit and all intervening sequences. Thus, a SSA reporter vector, with two truncated, non-functional copies of the bacterial LacZ gene and an I-CreI cut site within the intervening sequence was constructed in a yeast replicative plasmid. Cleavage of the cut site should result in a unique, functional LacZ copy that can be easily detected by X-gal staining.

The reporter vector was used to transform yeast cells. A small fraction of cells appeared to express functional LacZ, probably due to recombination events during transformation. Co-transformation with plasmids expressing either I-CreI or scI-CreI, in contrast, resulted in blue staining for all plated cells. Even in non-induced conditions (glucose), the residual level of protein was enough to induce SSA, suggesting that scI-CreI, as much as I-CreI, is highly efficient in yeast cells. Furthermore, SSA induction was truly dependent on cleavage of the target cut site by I-CreI proteins, as vectors devoid of that site display no increase in β-galactosidase activity compared to background levels.

The SSA assay was modified for tests in mammalian cells. The promoter and termination sequences of the reporter and meganuclease expression plasmid were changed, and plasmid recombination was evaluated in a transient transfection assay. Similar levels of induced recombination (2 to 3-fold increase) were observed with either scI-CreI or I-CreI. As in the yeast experiment, recombination depends on an I-CreI cut site between the repeats, for no increase of the β-galactosidase was observed in the absence of this site.

Another recombination assay, based on recombination between inverted repeats, was also used to monitor meganuclease-induced recombination in COS cells. As direct repeats can recombine by SSA, homologous recombination between indirect repeats requires a gene conversion event. Similar stimulation of gene conversion (3 to 4-fold) was observed with either scI-CreI or I-CreI. As expected for a true homologous recombination event, no enhancement was observed in the absence of an homologous donor template.

Example 2

Custom-Made Meganuclease Derived from I-Cre I Homing Endonuclease for HIV-2 Target Construction of a Phage-Displayed Library of I-Cre I Variants In order to engineer new meganuclease with altered specificities, a combinatorial library was constructed by mutagenesis of the I-Cre I homing endonuclease replacing DNA binding residues. Selection and screening applications then enabled to find those variants that were able to bind a particular, chosen DNA target. For phage display, as I-Cre I is a homodimer, a phagemid vector was required that encoded two separate I-Cre I proteins. Only one of the two I-Cre I copies, which was fused to the phage coat protein p3, was mutated. The resulting protein library, in phage display format, comprised thus I-Cre I wild-type/mutant heterodimers. Eight residues (Q26, K28, N30, Y33, Q38, Q44, R68 and R70) capable together of specific interactions with most of the bases in a single hal-site within the DNA target were selected. Our combinatorial library was obtained by replacing the eight corresponding codons with a unique degenerated VVK codon. Eventually, mutants in the protein library corresponded to independent combinations of any of the 12 amino acids encoded by the VVK codon (ADEGHKN-PQRST) at eight residue positions. In consequence, the maximal (theoretical) diversity of the protein library was $12^8$ or $4.29 \times 10^8$.

Construction of the Library

First, residue D75, which is shielded from solvent by R68 and R70, was mutated to N (Asn) in order to remove the likely energetic strain caused by replacements of those two basic residues in the library. Homodimers of mutant D75N (purified from *E. coli* cells wherein it was over-expressed using a pET expression vector) were shown to cleave the I-CreI homing site. A phagemid vector was then engineered that encodes wild-type I-CreI (FIGS. 2A and 2B: <<Natural>> or <<Non homologous>>) and the D75N mutant (FIG. 2C: <<Template>>) fused to the phage coat protein p3 and phage-displayed wild-type/D75N heterodimers were shown to bind that target DNA.

Second, two intermediate libraries of moderate size have been built: Lib1 (residues 26, 28, 30, 33 and 38 mutated; theoretical diversity $12^5$ or $2.48 \times 10^5$) and Lib2 (residues 44, 68 and 70 mutated; theoretical diversity $12^3$ or $1.7 \times 10^3$). DNA fragments carrying combinations of the desired mutations were obtained by PCR (several reactions in 50 µl), using degenerated primers (FIG. 2D: UlibIfor, UlibIrev, UlibIIfor, UlibIIrev) and as DNA template, the D75N gene. Lib1 and Lib2 were constructed by ligation of the corresponding PCR products, digested with specific restriction enzymes, into the D75N mutant gene, within the phagemid vector and within the pET expression vector, respectively. Digestions of vectors and inserts DNA were conducted in two steps (single enzyme digestions) between which the DNA sample was extracted (phenol:chloroform:isoamylalcohol) and EtOH-precipitated. 10 µg of digested vector DNA were used for ligations, with a 5:1 excess of insert DNA. *E. coli* TG1 cells were transformed with the resulting vectors by electroporation. To produce a number of cell clones above the theoretical diversity of either library, up to 35 electroporations of the Lib1 ligation samples and 4 electroporations of the Lib2 ligation samples were necessary. $4 \times 10^6$ (16 times the maximal diversity) and $6 \times 10^4$ (35 times the diversity) clones were thus obtained for Lib1 and Lib2, respectively (these numbers were corrected by the number of clones obtained using ligations done without inserts).

Figure 3:
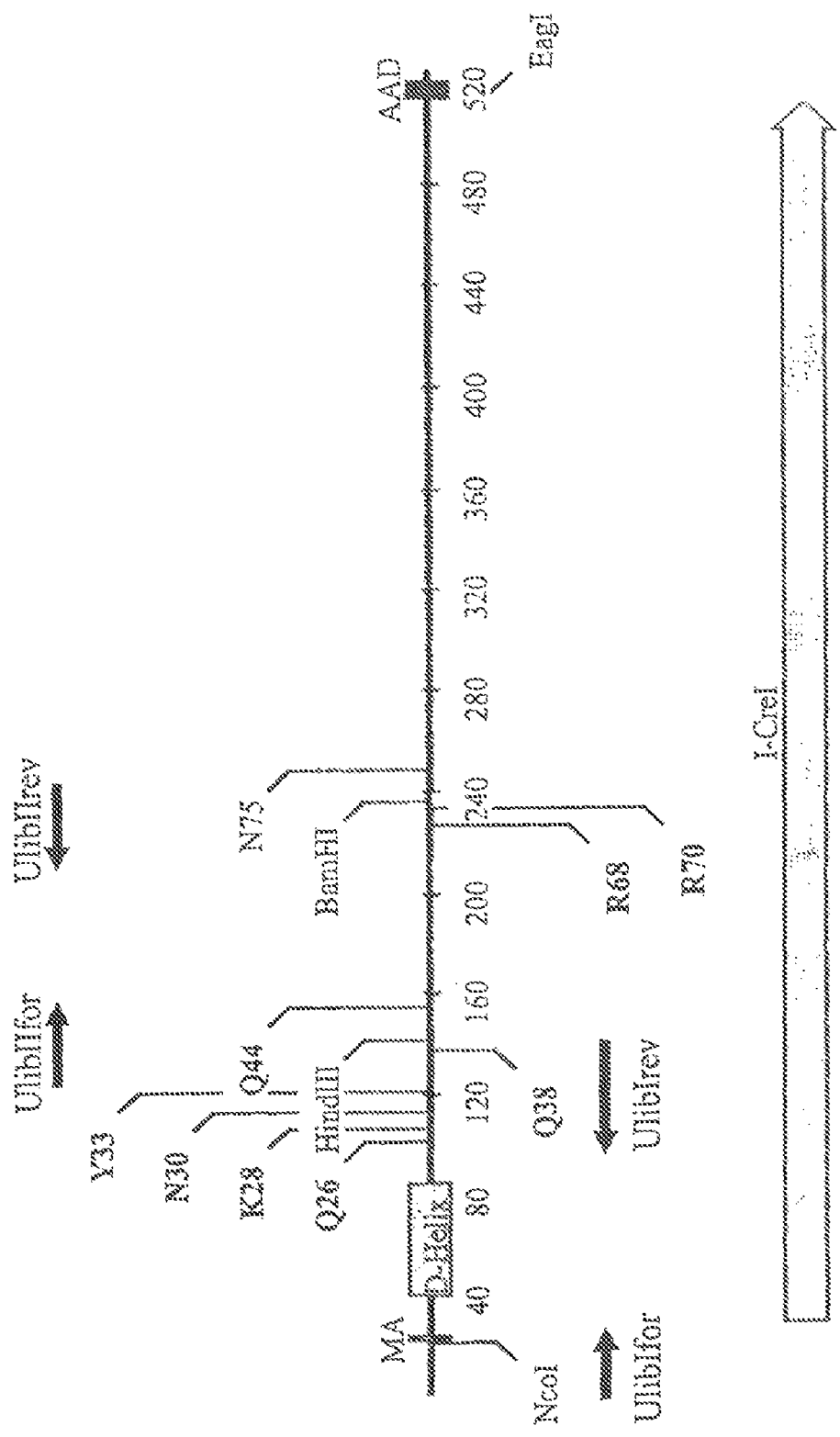
FIG. 3 is a schematic representation of the polynucleotide sequence called "Template" encoding the I-Cre I homing endonuclease comprising the mutation D75N. The dark arrows indicate the position of the primers UlibIfor, UlibIrev, UlibIIfor, and UlibIIrev used to generate the two libraries UlibI and UlibIII. D-Helix refers to the LAGLIDADG helix SEQ ID NO: 24). N75 refers to the mutation D75N.
Figure 4:
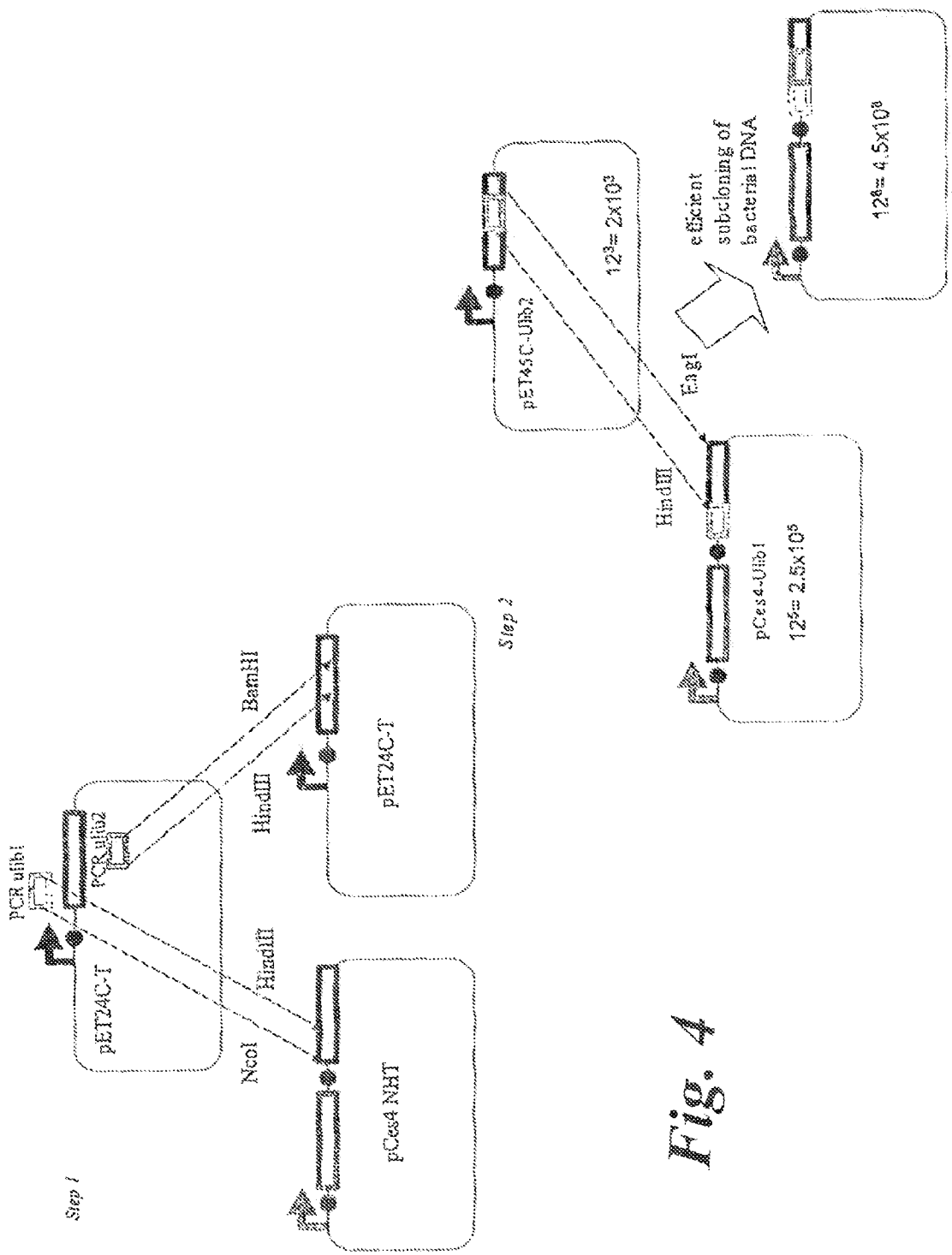
FIG. 4 is a schematic representation of the strategy for the library construction. Step 1: pET24C-T is a plasmid comprising a polynucleotide <<Template>>. Two PCR amplifications, PCR ulib1 and ulib2, are done with either UlibIfor and UlibIIrev, or UlibIIfor and UlibIIrev. The PCR ulib1 products are cloned in a phagemid pCes4 NHT. The PCR ulib2 products are cloned in a plasmid pET24C-T. Step 2: Subcloning a fragment of Ulib2 vector (pET45C-Ulib2) into the Ulib1 phagemid (pCes4-Ulib1).

Finally, Lib1 and Lib2 bacterial clones were scraped from plates and the corresponding plasmid vectors were extracted and purified. The complete library was then obtained by subcloning a fragment of the Lib2 vector into the Lib1 phagemid vector (see FIG. 4 for a schematic diagram of the library construction). Several rounds of DNA 2-step digestions, dephosphorylation, purification, quantification, ligation and electroporation were performed. After 4 rounds of 150 electroporation shots (which corresponds to 12 ligations of 1.4 µg vector with 0.4 µg insert), $5.5 \times 10^7$ bacterial clones were obtained (after correction for background). Bacteria were scraped and stored as a glycerol stock. In addition, an aliquot of this glycerol stock was used to inoculate a 200 ml culture and the library vector was extracted and purified from this culture for storage or potential subcloning.

Material and Methods

Protein Expression and Purification

His-tagged proteins were over-expressed in *E. coli* BL21 (DE3) cells using pET 24d (+) vectors (Novagen). Induction with IPTG (1 mM), was performed at 15° C. over 5 night. Cells were cracked for 1 h at 4° C. in a B-Per solution (Bacterial Protein Extraction Reagent, Pierce, 5 ml for 200 ml culture cell), containing protease inhibitors (Complete EDTA-free tablets, Roche) and DNase I (80 units)/nuclease (respectively 80 and 60 units, Roche). Alternatively, cells were sonicated in a solution of 25 mM HEPES (pH 8) containing protease inhibitors (Complete EDTA-free tablets, Roche) and 5% (v/v) glycerol.

Cell lysates were centrifuged twice (15 000 g for 30 min). His-tagged proteins were then affinity-purified, using 1 ml Hi-Trap chelating columns (Amersham) loaded with cobalt. Several fractions were collected during elution with a linear gradient of immidazole (up to 0.25 M immidazole, followed by plateau at 0.5 M immidazole and 0.5 M NaCl). Protein-rich fractions (determined by SDS-PAGE) were concentrated with a 10 kDa cut-off centriprep Amicon system. The resulting sample was eventually purified by exclusion chromatography on a Superdex75 PG Hi-Load 26-60 column (Amersham).

Fractions collected were submitted to SDS-PAGE. Selected protein fractions concentrated and dialyzed against a solution of 25 mM HEPES (pH 7.5) and 20% (v/v) glycerol.

In Vitro Cleavage Assay pGEM plasmids with single meganuclease DNA target cut sites were first linearized with XmnI. Cleavage assays were performed at 37° C. in 12.5 mM HEPES (pH 8), 2.5% (v/v) glycerol and 10 mM $MgCl_2$. Reactions were stopped by addition of 0.1 volume of 0.1 M Tris-HCl (pH 7.5), 0.25 M EDTA, 5% (w/v) SDS, and 0.5 mg/ml proteinase K and incubation at 37° C. for 20 minutes. Reaction products were examined following separation by electrophoresis in 1% agarose gels.

Phagemid Construction

Phage Display of I-Cre I/D75N heterodimer was obtained by using a phagemid harboring two different ORFs as a bicistron, under the control of promoter pLac. The first one yields a soluble protein fused to a N-terminal signal sequence directing the product into the periplasmic space of *E. coli* Gene 1-Cre I WT was cloned into this ORF using restriction enzymes ApaLI and AscI. The D75N domain was cloned into the second ORF using Nco I and Eag I restriction enzyme, leading to a fusion with the phage coat protein p3 via a hexahis tag (SEQ ID NO: 27), a C-Myc tag and an amber stop codon. This final phagemid was called pCes1CreT. In a suppressive strain like TG1 or XL1 blue, and after infection by a helper phage (e.g. M13K07), D75N-p3 fusions are incorporated in the phage coat and the soluble I-CreI monomers produced in the same compartment will either dimerize or interact with the displayed D75N domain, thereby producing particles displaying I-CreI WT/D75N heterodimer.

Phage Production

A 5 mL culture of 2×TY containing 100 µg/ml of ampicillin and 2% glucose was inoculated with a 1/100 dilution of an overnight culture of bacteria containing phagemid pCesICreT and agitated at 37° C. At an $OD_{600}$ of 0.5, phage helper M13K07 (Pharmacia) was added at a ratio phage:bacteria of 20:1. After 30 min at 37° C. without agitation, the culture was centrifuged for 10 min at 4000 rpm and the pellet was resuspended in 25 ml of 2×TY containing 100 µg/mL Ampicillin and 25 µg/mL Kanamycin, and agitated overnight at 30° C. Culture were centrifuged and supernatant were used as such in phage ELISA.

PhageELISA

Microtiter plates were coated for 1 h at 37° C. with 100 µl/well of biotinylated BSA at 2 µg/mL in PBS. After several washes in PBS containing 0.1% Tween20 (PBST), wells were incubated with 100 µl/well of streptavidin at 10 µg/mL in PBS and incubated for 1 h at RT. Plates were further washed and incubated with biotinylated PCR fragments harboring the target site, at 250 pM in PBS. After 1 h incubation at RT and washing, plates were saturated with 200 µl/well of PBS containing 3% powder milk and 25 mM $CaCl_2$ (PMC). PMC was discarded and plates were filled with 80 µl of PMC and 20 µl/well of culture supernatant containing the phage particles. After 1 h of incubation at RT, plates were extensively washed with PBST and incubated with 100 µl/well of anti 25 M13-HRP conjugated antibody (Pharmacia) diluted 1/5000 in PMC. Plates were incubated for 1 h at RT, washed and incubated with TMB solution (Sigma). The reaction was blocked with 50 µl/well of 1M $H_2SO_4$. Plates were read at 450 nm. A signal higher than 3× the background (irrelevant target) can be considered as positive.

PCR-Based Mutagenesis

Plasmid pET24-T45 containing the gene I-CreI D75N was diluted at 1 ng/µl to be used as template for PCR. Degenerated oligonucleotides encoding the desired randomizations were used to amplify PCR fragments Lib1 and Lib2 in 4×50 µl PCR reactions per inserts. PCR products were pooled, EtOH precipitated and resuspended in 50 µl 10 mM Tris.

DNA Digestions

All enzymes and the corresponding buffers were from NEBiolabs. Digestions of up to 10 µg DNA were realised using up to 100 U of a first restriction enzyme, at 37° C., in 150 or 500 µl final reaction volume. After 2 h to 6 h, digested DNA was phenol extracted and EtOH precipitated. Digestion substrates and products were separated using agarose gel electrophoresis, the desired product being extracted from the gel and purified (Nucleospin Extract, Macherey-Nagel). For PCR inserts, digestions were directly purified on Nucleospin columns. The second digestion was then performed in identical conditions. At the end of this second digestion reaction, 0.1 volume of 10×CAP buffer and 0.5 µl of CAP were added to the digested vectors, and the samples were further incubated for 30 min at 37° C. (The alkaline phosphatase was inactivated by incubating the sample 10 min at 70° C., after addition of EDTA). Eventually, the digested and de-phosphorylated DNA was phenol extracted, EtOH precipitated and resuspended in 30 µl of 10 mM Tris pH8. Final DNA concentrations were estimated by comparison of band intensities in agarose gels after electrophoresis.

Ligations

Large-scale ligations were done at 16° C. (for 16 h) using 1400 ng of digested vector and a 5:1 molar excess of digested in 200 µl reaction volumes and with 4000 U of T4 DNA ligase (NEBiolabs). After ligation, reaction samples were incubated for 20 min at 65° C. to inactivate the ligase. The vector DNA was eventually EtOH precipitated and resuspended at 25 ng/µl in 10 mM Tris pH8.

Electroporations

40 µl of homemade electrocompetent cells TG1 were mixed with 25 ng of ligated DNA (1 µl) in a 2 mm cuvette. After 1 min on ice, cells were pulsed (2.5 Kv, 25 µF, 200 Ohm) and immediately resuspended in 1 ml of 2×TY+2% glucose. Cells were placed at 37° C. for 1 h with agitation, and then plated on large 2×TY plates containing ampicillin (phagemid vector) or kanamycin (pET vector) and 2% glucose and incubated overnight at 30° C. Aliquots were also diluted in 2×TY and plates on small 2×TY Ampicillin glucose plates to obtain isolated colonies allowing the calculation of library diversities and characterization of several clones by restriction analysis.

Selection and Screening of Meganuclease Building to a HIV2-Derived DNA Target from a Library of I-Cre I Variant Using Phage Display The goal of this project was to obtain a meganuclease capable of cutting a sequence found in the genome of HIV2 (GGAAGAAGCCTTAAGACATTTTGA (SEQ ID NO: 13)). The homing endonuclease I-Cre I was used as a scaffold to build a library of $10^8$ variants by randomizing 8 residues located at the DNA-binding interface of one I-Cre I monomer (see previous section). This library was enriched for binders by several rounds of selection/amplification using biotinylated DNA fragments harboring the HIV2 derived target (HIV6335). The selected targets were subsequently screened for binding using a phage ELISA.

Materials and Methods

Phagemid Format

A phagemid based on pCesI (pCLS346) was chosen. This plasmid harbored two different ORFs as a bicistron, under the control of promoter pLac. The first one yielded a soluble protein fused to a N-terminal signal sequence directing the product into the periplasmic space of *E. coli*. In our case, this first product was a wild-type monomer of I-CreI. The second ORF encoded an I-CreI monomer that was fused to the phage coat protein p3 via a hexahis tag (SEQ ID NO: 27), a C-Myc tag and an amber stop codon. In a suppressive strain like TG1 or XL1blue, and after infection by a helper phage (e.g. M13K07), bacteria harboring this phagemid produces phage particles and around 1-10% of them displays the recombinant protein on their surface.

The monomer fused to p3 and randomized on the DNA-binding interface was incorporated in the phage coat and the soluble I-CreI monomers produced in the same compartment either dimerize or interact with the displayed monomer, thereby producing particles displaying I-CreI homodimers (or heterodimers if the monomer fused to p3 was mutated).

Target Production

Two complementary primers encoding the desired sequences but harboring an extra adenosine in 3' were annealed and ligated into pGEM-t Easy (Promega). After sequencing, a correct clone was chosen as template to PCR amplify a biotinylated 200 pb fragment using the kit KOD (Novagen) and primers SP6 (TTTAGGTGACACTATA-GAATAC (SEQ ID NO: 28)) and biotT7 (biot-TAATAC-GACTCACTATAGG (SEQ ID NO: 29)). The PCR product concentration was estimated on gel and the fragment was used as such in ELISA or selection procedures.

Rescue of the Phagemid Library

A representative aliquot of the library (at least 10× more bacteria than the library size) was used to inoculate 50 ml of 2×TY containing 100 μg/ml ampicillin and 2% glucose (2TYAG) and the culture was agitated at 37° C. At an $OD_{600}$ of 0.5, 5 ml of this culture was infected with helper phage K07 at a ratio phage:bacteria of 20:1 and incubated without agitation for 30 min at 37° C. After centrifugation at 4000 rpm for 10 min at room temperature (RT), the pellet was resuspended in 25 ml of 2×TY containing 100 μg/ml ampicillin and 25 μg/ml kanamycin (2TYAK) and agitated overnight at 30° C. The culture was centrifuged at 4000 rpm for 20 min at 4° C. and phage particles were precipitated by the addition of 0.2 volume of 20% PEG6000/2.5M NaCl for 1 h on ice.

After centrifugation at 4000 rpm for 20 min at 4° C., the phage pellet was resuspended in 1 ml of PBS and centrifuged at 10 00 rpm for 5 min. 0.2 volume of 20% PEG6000/2.5M NaCl was added to the supernatant and the mix was centrifuged at 10 000 rpm to pellet the phage particles. Particles were finally resuspended in 250 μl PBS.

Selection Procedure

Phage particles were diluted in 1 ml of PBS containing 3% dry milk and 25 mM CaCl (PMC) and incubated for 1 h at RT. 100 pl Streptavidin beads (Dynal, 200 μl for the first round) were washed 3× in PMC and blocked for 1 h in the same buffer. The biotinylated targets were added to the phage at the indicated concentration and the mix was agitated at RT for 1 h. Beads were added to the mix and incubated at RT for 15 min. Beads were collected on the vial wall using a magnet and washed 10× in PMC containing 0.1% tween. After a final wash in PBS, beads were resuspended in 0.5 ml of 100 mM Triethanolamine pH 12 and incubated for exactly 10 min. The supernatant were collected and immediately neutralized by 0.5 ml of 1 M Tris pH8. An aliquot of this eluate was serially diluted for titration and with 4 ml 2×TY. 5 ml of exponentially growing TG1 cells were added and the mix was incubated for 30 min at 37° C. without agitation. Cells were plated on large 2TYAG plates and incubated overnight at 30° C. Colonies were resuspended in 2TYAG, adjusted to an $OD_{600}$ of 100 and kept at −80° C. after addition of 15% glycerol.

Screening by Phage ELISA

Isolated colonies from selection outputs were toothpicked into 100 μl of 2TYAG in 96 well plates, and agitated overnight at 37° C. Next day, a fresh plate containing 100 μl 2TYAG was isolated using a transfer device. 50 μl of sterile 60% glycerol was added to the overnight plate and this masterplate was stored at −80° C. The fresh plate was agitated at 37° C. for 2.5 h, rescued by the addition of 2TYAG containing 2×10⁹ pfu of helper phage M13K07, incubated for 30 min at 30° C., spun at 1700 rpm for 15 min. Cells pellets were resuspended in 150 μl 2TYAK and agitated overnight at 30° C. After centrifugation, 20 μl of supernatant was used as described in the previous section.

Results

Selections

Phage particles displaying I-Cre I variants were produced by infecting bacteria harboring the phagemid library with helper phage M13K07. Phage particles were purified by PEG precipitation and incubated with a biotinylated PCR fragment harboring HIV6335 target. After 1 h of incubation at room temperature, streptavidin-coated magnetic beads were added to the solution to retrieve the biotinylated DMA and bound phages. The beads were extensively washed and the bound phages were eluted by pH shock. Bacteria were infected with the eluted phages and plated on large 2×TYplates containing ampicillin and 2% glucose. Serial dilutions of an aliquot of the eluted phages were used to infect bacteria to calculate the number of phage particle and obtain isolated colonies.

The day after, bacteria were scrapped from the large plates and stored as glycerol stocks. An aliquot (representative of the diversity) was used to produce a new batch of phage particles for a second round of selection.

The stringency of the selections was increased after each round. The first selection was done using 10 nM of biotinylated target. The second was done with 400 pM and the washing steps were extended. The third round was done using 250 pM and washed more extensively.

As shown on Table 1, the first and second rounds of selection against the HIV2 target lead to an output titer characteristic of background values ($10^5$ to $10^6$ pfu/ml). However, a significant enrichment was measured on round 3.

TABLE 1

Selection titers. C2H6335: selection done on HIV2 target using the library described in the other example.

| Selection Round | Input (pfu/ml) | Output (pfu/ml) | Enrichment |
|---|---|---|---|
| 1 | $6.4 \times 10^{11}$ | $1.4 \times 10^5$ | NA |
| 2 | $4.0 \times 10^{12}$ | $3.0 \times 10^6$ | 3 |
| 3 | $2.8 \times 10^{12}$ | $6.9 \times 10^7$ | 33 |

NA: non applicable.
Enrichment is defined as (output n + 1/input n + 1)/(output n/input n).
Screening by phage ELISA 80 clones randomly picked from each output (as well as unselected clones) were used to produce phage particles displaying I-CreI variants in a monoclonal fashion. Supernatants containing the phage particles were incubated on biotinylated PCR fragment immobilized on plastic via streptavidin. Bound phages were stained with an HRP-labeled anti p8 (major coat protein) monoclonal antibody (Pharmacia). As shown on Table 2, no binders were detected among the unselected clones or from the outputs of the first round of selection. However 60% of clones picked after round 2 against are positive against H6335 but negative on an irrelevant target (P1234, target of homing endonuclease PI-SceI). This result is in good agreement with the output titer. Indeed this selection only resulted in a mild enrichment, suggesting that a large number of clones still originate from background. As expected, a third round of selection lead to 99% of strong binders, which explains the large number of output phages after this third selection.

TABLE 2

Percentage of positive clones in a ELISA assay directed against the I-CreI target (C1234) or the HIV2 derived target (H6335). 77 clones were assayed for each output.

| Selection round | % positive against C1234 | % positive against P1234 |
|---|---|---|
| 0 | 0 | 0 |
| 1 | 0 | 0 |
| 2 | 60 | 0 |
| 3 | 99 | 0 |

Round 0: unselected library

Using phage display, new meganucleases were selected from a large library of I-Cre I variants. Selections on biotynilated DNA targets lead to an increase of output titers characteristic of an enrichment for molecules capable of binding the DNA targets. This enrichment was confirmed by phage ELISA. These results demonstrate the efficiency of the selection and screening methods.

A Selection/Screen Experiment in Yeast to Identify Novel Meganucleases.

Material and Methods

Bacterial and Yeast Strains

Every subcloning and plasmid preparations are performed in XLI-blue: *E. coli* provided by Stratagene following standard procedures. Experiments in *S. cerevisiae* are done in the following strains:

FYC2-6A: alpha, trp1Δ63, leu2Δ1, his3Δ200

FYBL2-7B: a, ura3Δ851, trp1Δ63, leu2Δ1, lys2Δ202

YASP3 (derived from FYC2-6A): alpha, ura3::SSA-ura3-HIV2-KanR, ade2::SSA-ade2-HIV2-TRP1, trp1Δ63, leu2Δ, his3Δ200

Plasmids:

pCLS0279: ADH1 promoter, TRP1 selectable marker and ARS-CEN origin of replication, β-galactosidase SSA target, HIV2 6335 cleavage site.

pCLS0569: kanamycin resistance cassette, HIV2 6335, internal fragment of the URA3gene.

pCLS0570: kanamycin resistance cassette, HIV2 6335, internal fragment of the LYS2 gene.

pCLS0576: TRP1 selectable marker, HIV2 6335, internal fragment of the ADE2 gene.

pCLS0047: Galactose inducible promoter, LEU2 selectable marker and 2 micron origin of replication.

Results

We decided to perform an in vivo assay in yeast that allows to screen mutagenized I-CreI protein variants with detectable activity towards a specified target.

A library of mutated I-CreI meganucleases has been first selected by a phage display procedure, resulting in a sublibrary enriched for variants of interest, able to bind the HIV2 6335 target. The inserts from this enriched sub-library are subcloned into pCLS0047 under the control of a galactose-inducible promoter, for further selection in yeast. However, we can produce the library directly in the suitable yeast expression vector, and void the phage display step.

We prepared a specific yeast strain (YASP3) containing two reporter systems integrated in chromosomes. These two reporter systems are based on recombination by Single Strand Annealing (SSA). SSA is induced by specific cleavage of the HIV2 6335 site.

Namely, we introduced a URA3 SSA target and an ADE2 SSA target. The URA3 SSA target was a modified ura3 gene with 2 direct repeats of 600 base pairs separated by 4.3 kb (containing a kanamycin resistance cassette and the HIV2 6335 cleavage site). The strain was unable to grow on a minimal medium lacking uracile but was resistant to G418. When this target was cleaved and recombined properly, the yeast was able to grow on media without uracil and was sensitive to G418.

The ADE2 SSA target was a modified ade2 gene with 2 direct repeats of 1.1 kb separated by 3.6 kb (containing a tryptophan selectable marker and the HIV2 6335 cleavage site). Because of this mutated ade2 gene, the yeast strain was unable to grow on a minimal medium lacking adenine, but harbored a red color on a medium with a low adenine content. Because of the tryptophan selectable marker, it was able to grow on minimal media without tryptophan. When this target was cleaved and recombined properly, the yeast was white, able to grow on media without adenine and unable to grow on a minimal medium lacking tryptophan.

Basically, the recipient yeast strain was red (on low adenine medium), G418 resistant, tryptophan prototroph and auxotroph for uracile and adenine. If a specific meganuclease is expressed in this strain and cleaves its target sites, the resulting yeast clone is white, G418 sensitive, prototroph for tryptophan and auxotroph for uracile and adenine.

The YASP3 strain was validated by determining the level of spontaneous recombination of each target alone and of both targets taken together. The URA3 SSA 10 target recombined spontaneously as an uracile prototrophe, G418 sensitive at an approximate $6 \cdot 10^{-4}$ rate. The ADE2 SSA target recombined spontaneously as an adenine prototrophe at an approximate $2.7 \cdot 10^{-3}$ rate. Recombination of both markers occurred spontaneously (resulting in uracile/adenin rototrophes) at an approximate $10^{-6}$ rate.

A pilot experiment with 1.5×10 in transformants showed no background level of uracileladenine prototrophes means that the number of false positive clones should be less than 10 after a transformation experiment with a library that would yield about a million of independent clones.

The library is used to transform YASP3. A classical chemical/heat chock protocol that routinely gives $10^6$ independent transformants per pg of DNA was used (Gietz, R. D. and Woods, R. A., 2002) Transformation of yeast by lithium acetate/single-stranded carrier DNA/polyethylene glycol method (Methods Enzymol, 350, 87-96).

Transformation of the strain with the library gives more than $10^6$ independent yeast transformants from which a number of clones are able to grow on a selective medium without uracile, leucine and containing galactose as a carbon source and a low amount of adenine. Among those clones, the interesting ones are white indicating that they contain a LEU2 vector allowing the expression of a meganuclease specific for HIV2 6335 site and that the enzyme is able to cut both URA3 and ADE2 reporters.

The positive clones are isolated and screened for their ability to induce the specific recombination of a plasmidic SSA β-galactosidase target (pCLS0279). This plasmidic reporter was a modified LacZ gene with 2 direct repeats of 825 base pairs separated by 1.3 kb (containing a URA3 selectable marker and the HIV2 6335 cleavage site). The vector (which can be selected on a medium without tryptophan) is used to transform a yeast strain (FYBL2-7B) and clones are maintained on minimal media 35 lacking uracile to maintain the unrecombined LacZ target.

Yeast clones resulting from the selection experiment are mated with the yeast strain containing the SSA β-galactosidase target. Diploids are selected and assayed for induced β-galactosidase activity. A number of clones are expected to behave as false positives at this step. They correspond to the background level of spontaneous recombination of the URA3 and ADE2 SSA targets. All remaining clones (uracile and adenine auxotrophes able to induce recombination of the SSA-LacZ target) are true positives expressing a meganuclease cleaving the HIV2 6335 target in vivo. Also, other experiments, based on the ones described above, can be used to determine more precisely the activity of such novel enzymes.

Example 3

Use of Meganuclease for Antiviral Therapy

Experimental Procedures

Cells

COS-7 cell lines from the American Type culture collection (ATCC) were cultured in DMEM plus 10% fetal bovine serum. PC-12 cells from ATCC were grown in RPMI1640 supplemented with 10% heat-inactivated horse serum and 5% heat-inactivated fetal bovine serum. PC-12 cells were differentiated as previously described (Su et al., 1999, Journal of Virology, 4171-4180). Briefly, cells were seeded on 6 well-plate at 5 10$^4$ cells per well. The following day, cells were incubated in PC-12 medium containing 100 ng/ml of 2.5S NGF (Invitrogen). Medium was changed every three days. After 7 days of incubation, undifferentiated cells were eliminated by adding 2 µM of fluorodeoxyuridine (FdUrd).

Construction of Recombinant HSV-1

HSV-1 was purchased from ATCC. Viruses were propagated on COS-7 cells at low MOI (0.01 PFU/cell). Recombinant virus (rHSV-1) were generated as previously described (Lachmann, R. H., Efstathiou, S., 1997, Journal of Virology, 3197-3207). A 4.6 Kb pstI-bamHI viral genomic DNA fragment was cloned in pUC 19. Based on HSV-1 sequence from data base (ID: NC 001806), this region represents nucleotides 118867 to 123460. A cassette consisting of a CMV promoter driving Lac gene expression was introduced into a168 by HpaI deletion. This region is located within the major LAT locus of HSV-1. I-Sce I cleavage site was finally cloned directly after the CMV promoter. This construct was used to generate recombinant viruses. Plasmid was linearized by XmnI digestion, and 2 µg of this plasmid DNA was contransfected with 15 µg of HSV-1 genomic DNA prepared from COS-7 infected cells by CaCl$_2$ method. After 3 or 4 days, infected cells were harvested and sonicated. Aliquot of the lysed cells were used to infect COS monolayer. Virus recombinant were selected by overlaying COS monolayer with 1% agarose in medium containing 300 µg/ml of X-Gal (5-bromo-4-chloro-3-indolyl-β-D-galactopyranoside). Blue clones were picked and further subjected to three round of plaque purification. Presence of the I-Sce I site was confirmed by PCR and in vitro I Sce-I enzymatic digestion.

Viral Inhibition 6 well-plate were seeded with 2.10$^4$ cells per well. The next day COS-7 cells were transfected with 0.5 µg of plasmid expressing ISce-I or containing the I-Sce-I ORF in the opposite orientation by the EFFEC-TENE method according to the manufacturer protocol. We achieved routinely in our laboratory 60 to 70% efficiency using this methodology. Fourty eight hours later, subconfluent transfected cells were infected with rHSV-1. For infection, rHSV-1 was diluted in PBS containing 1% fetal bovine serum and adsorbed onto cells for 20-40 min at 37°, in humidified incubator with 5% CO2. 6 wells-plates were infected at 30 or 300 PFU per well for respectively viral inhibition or cells survival experiments. Cells were harvested at day 1, 2, and 3 and β-galactosidase activity was assayed and DNA extracted.

β-Galactosidase Activity

Cell monolayer was fixed in 0.5% glutaraldehyde in 100 mM PBS containing 1 mM MgCl$_2$ at 4° for 10 minutes. After one wash with detergent solution (100 mM PBS, 1 mM MgCl$_2$, 0.02% Nonidet p-40) cells were incubated at 37° in X-Gal stain solution (10 mM PBS, 1 mM MgCl$_2$, 150 mM NaCl, 33 mM K$_4$Fe(CN)$_6$.3H$_2$O, 33 mM K$_3$Fe(CN)$_6$, 0.1% X-Gal) until color development. Beta-galactosidase activity was also measured on cell extract with o-nitrophenyl-β-D-galactopyrannoside (ONPG) as substrate. Cell monolayer was washed once with PBS. Cells were then lysed with 10 mM Tris ph 7.5, 150 mM NaCl, 1% Triton X-100, protease inhibitors. After 30 minutes incubation on ice cell lysate was centrifuged and β-galactosidase was assayed. Typically 30 µl of supernatant was combined with 270 µl of reaction buffer (10 mM PBS; ph 7.5, 1 mM MgCl$_2$, 0.3% β-mercaptoethanol) containing 800 µg/ml ONPG. The reaction was carried out at 37° and stopped with 0.5 ml of 1M NaCO$_3$. Optical density was measured at 415 nm. Beta-galactosidase activity is calculated as relative unit normalized for protein concentration and incubation time.

Semi-Quantitative PCR

To measure viral replication of rHSV-1, oligonucleotides were designed to amplify a 217 by fragment from Lac gene. The standard DNA used in this assay was generated by cloning this fragment in a Bluescript plasmid, and by inserting a 50 by fragment downstream to the 5' oligonucleotide. PCR of the standard produced 267 by amplicon. Series of PCR (not shown) were carried out to fix the amount of standard and DNA sample, and the number of cycles to achieve linear response of the amplification. The basic semi-quantitative PCR were carried out in a total volume of 30 µl, using the READYMIX™ TAQ (Sigma) with 20 pmols of each primers and 180 pg of DNA. The tubes were heated for 4 min at 94° and subjected to 22 cycles: 94° for 1 min, 62° for 50 sec, 72° for 2 min, and 72° for 7 min.

Virus Titration

In one series of experiments, the culture medium was collected every day at days 1, 2, 3, and 4, and fresh medium was added. In the other, the medium was not changed during experiment and aliquots were collected every day. To monitor for the release of HSV-1 progeny, aliquot of medium were titred on COS-7 cells by standard plaque assay.

Results

Figure 6A:
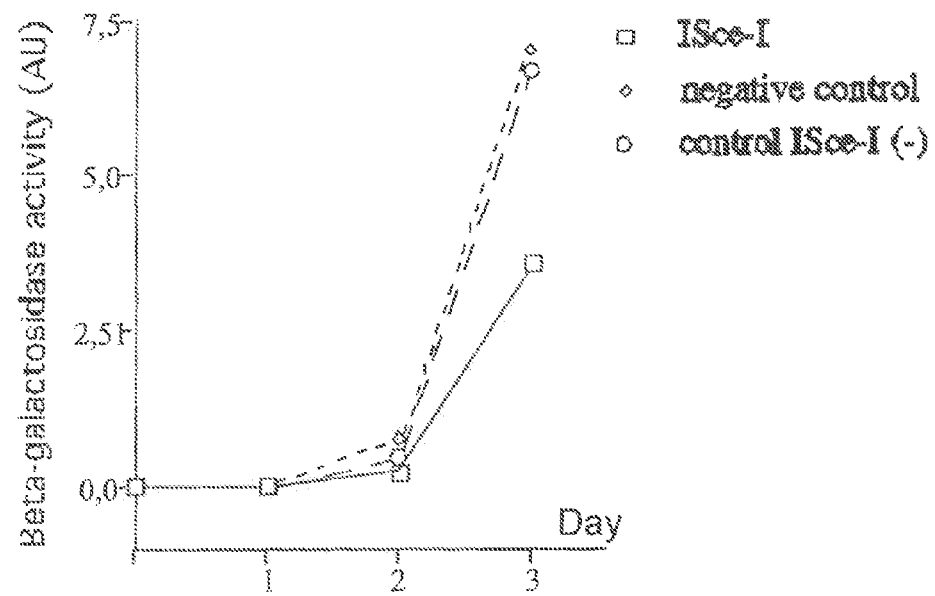
FIG. 6A: cells monolayer was infected with 30 PFU. HSV-1 growth was quantified by β-galactosidase activity in cell lysate.
Figure 6B:
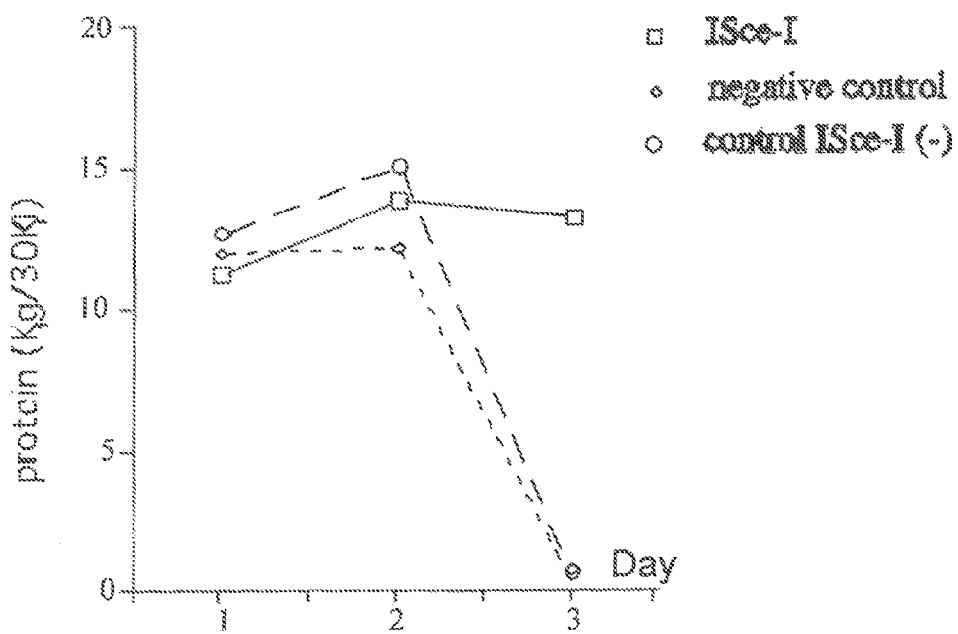
FIG. 6B, cell monolayer was infected with 300 PFU. Cell survival was measured by protein determination in cell lysate. I-Sce I refers to vector expressing I-Sce I; I-Sce I(−) refers to a vector in which ORF of I Sce-I was inserted in reverse orientation; negative control refers to control plasmid.
Figure 7A:
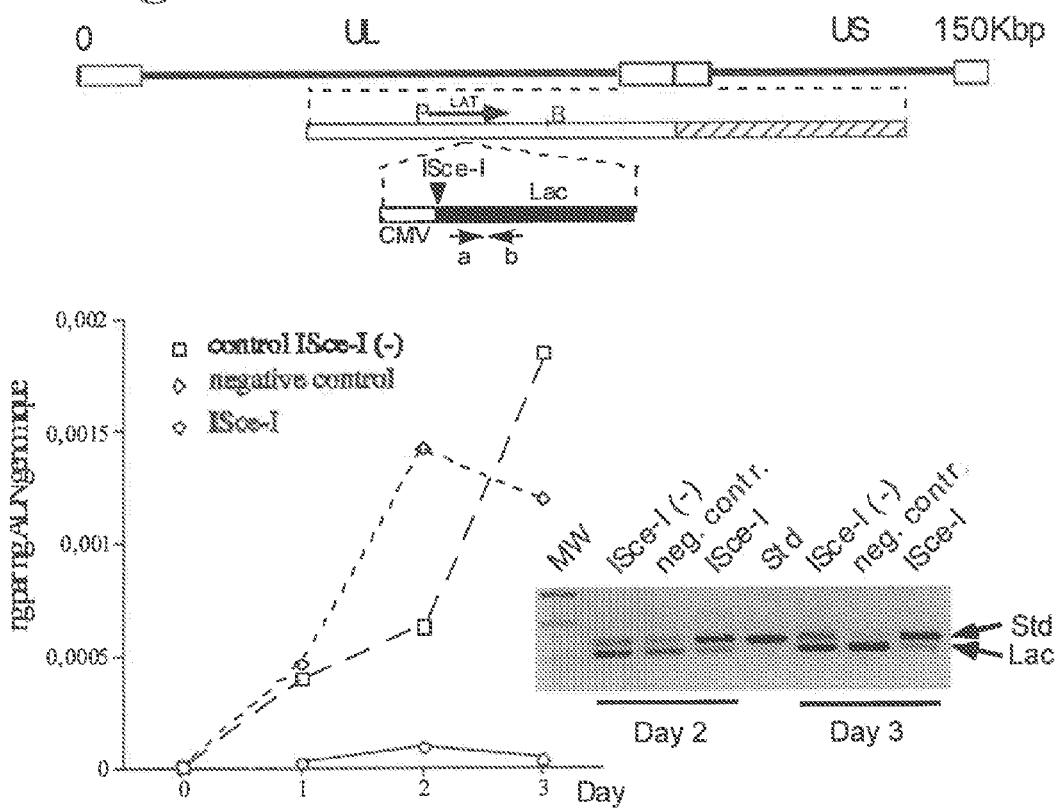
FIG. 7A is a schematic representation of recombinant HSV-1 genomic DNA. Cassette containing CMV promoter driving Lac gene was inserted in the major LAT transcript. I-Sce I restriction site was cloned between promoter and reporter gene. a and b represent primers used for the semi-quantitative PCR. COS-7 monolayers were transfected with vector expressing I-Sce I or with control plasmids. Fourty eight hours after transfection cells were infected with rHSV-1 (30 PFU). DNA was extracted 1, 2 or 3 days after infection. PCR was carried out as described in <<experimental procedures>>. Std refers to Internal standard; Lac refers to an amplicon of the rHSV-1 Lac gene. I-Sce I refers to vector expressing I-Sce I; I-Sce I(−) refers to a vector in which ORF of I-Sce I was inserted in reverse orientation; negative control refers to control plasmid.
Figure 7B:
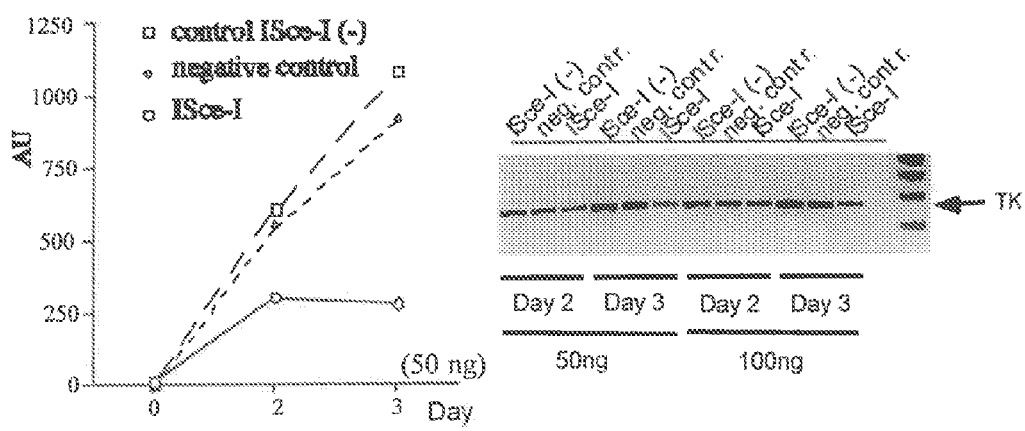
FIG. 7B, PCR quantification of the viral thymidine kinase (TK) gene. PCR was carried out at 2

The effect of I-Sce I on viral replication was examined using a recombinant Herpes simplex virus carrying a I-Sce I restriction site (rHSV-1). For convenience, rHSV-1 was build with a cassette containing CMV promoter driving the Lac gene. I-Sce I site was inserted at the junction of the CMV promoter and Lac gene. The expression cassette was cloned by homologous recombination in the major LAT locus which allowed Beta-galactosidase (β-gal) expression during lytic infection in COS-7 cell monolayer. Strinkingly transfection of I-Sce I expression vector before viral infection virtually completely inhibited HSV-1 plaque formation in COS cells (FIG. 5) as shown by X-Gal coloration. In contrast, control transfection with expression vector containing I-Sce I open reading frame in the reverse orientation which did not allow any functional transcript, did not affect viral replication. Furthermore, 48 hours after infection, the cells were checked for I-Sce I expression. All the lysis plaques formed in cells monolayer transfected with I-Sce I expression vector represented cells which did not expressed I-Sce I (the transient transfection is about 70% efficient). However, cells expressing I-Sce I surrounding the lysis plaque inhibited the viral propagation. The I-Sce I effect was confirmed by measuring the β-galactosidase activity in a cell lysate. After infection of COS-7 cells monolayer transiently expressing I-Sce I with 30 Pfu per well cell monolayer was collected at day 1, 2, and 3 post infection and β-gal was assayed. FIG. 6A shows a drastic decrease of the β-galactosidase activity reflecting the inhibition of rHSV-1 replication. The protective effect of I-Sce I over a time course of rHSV-1 infection was evaluated next. At 3 days after infection, cells transfected with I-Sce I expressing vector shown no sign of cytopathic effect whereas control cultures were completely lysed as shown in FIG. 6B. In an effort to quantify the degree of inhibition of viral DNA replication by I-Sce I, we have set-up a semi-quantitative PCR. Genomic DNA was extracted from cells at day 1, 2, and 3 after infection. PCR was carried out with primers a and b (FIG. 7A)

generating a 217 by amplicon in Lac gene. An internal standard was added in sample before PCR to quantify DNA. Lac gene was virtually not detectable in I-Sce I expressing cells at 3 days post-infection (FIG. 7A). In contrast cells that did not received I-Sce I expression vector shown high levels of virus DNA. This result was confirmed by PCR using primers in viral endogenous gene (FIG. 7B). Amplification of Thymidine Kinase (TK) gene shown that I-Sce I inhibited the viral replication. Finally COS-7 cells expressing active I-Sce I or I-Sce I ORF in the reverse orientation were infected with rHSV-1 and the concentration of virus released in the medium at different time points was measured by plaque assay (FIG. 8). Viruses were quantified in a rough array at day one when I-Sce I was produced. Viruses production was still markly decreased two days after the infection when compared with cells which did not expressed I-Sce I showing that I-Sce I effectively inhibited viral replication. This effect was still observed at day three although in a lesser extent. Probably the high mutation rate occurring during viral replication allowed emergence of mutant HSV-1 which were able to escape the I-Sce I activity.

Taking together, these results demonstrates that I-Sce I and more generally meganucleases can be used to inhibit viral infection. The use of custom-made meganuclease or combination of custom-made meganucleases designed to cut specific viral sequences could represent a powerful new strategy in the antiviral therapy.

Example 4

Meganuclease with Altered Binding Properties Derived from I-CreI Homing Endonuclease The purpose of this experiment was to obtain novel meganucleases binding target sites close to the I-CreI natural target site. A series of 6 targets were used (FIG. 9), including the wild-type natural I-CreI target (named C1234), the HIV2 target described in example 2 (named here 141234), and four additional targets. These four additional targets are 24 by palindromes corresponding to inverted repeats of a 12 by half I-CreI or HIV2 target site: C1221 and C4334 are inverted repeats of the first half and second half, respectively, of the C1234 target; H1221 and H4334 are inverted repeats of the first half and second half, respectively, of the H1234 target.

In contrast with example 2, the method used here did not involve any selection step, but was based on the extensive screening of the Lib2 library (see example 2). Three residues (Q44, R68 and R70) capable of base specific interactions with the DNA target were selected. The combinatorial library was obtained by replacing the three corresponding codons with a unique degenerated VVK codon. Eventually, mutants in the protein library corresponded to independent combinations of any of the 12 amino acids encoded by the VVK codon (ADEGHKNPQRST) at three residue positions. In consequence, the maximal (theoretical) diversity of the protein library was $12^3$ or 1728.

Materials and Methods

Construction of a Phage-Displayed Library of I-CreI Variants.

First, residue D75, which is shielded from solvent by R68 and R70, was mutated to N (Asn) in order to remove the likely energetic strain caused by replacements of those two basic residues in the library. Homodimers of mutant D75N (purified from *E. coli* cells wherein it was over-expressed using a pET expression vector) were shown to cleave the I-CreI homing site. A phagemid vector was then engineered that encodes the D75N mutant (FIG. 2C: <<Template>>) fused to the phage coat protein p3 and phage-displayed D75N monomers were shown to bind the I-CreI natural DNA target (C1234 on FIG. 9).

Then, DNA fragments carrying combinations of the desired mutations were obtained by PCR (several reactions in 50 µl), using degenerated primers (FIG. 2D: UlibIIrev) and as DNA template, the D75N gene. Lib2 was constructed by ligation of the corresponding PCR products, digested with specific restriction enzymes, into the D75N mutant gene, within the phagemid vector, as described in example 2.

Screening of Meganucleases Binding to the 6 Different Targets

Screening was performed by Phage ELISA, as described in example 2.

Results 4560 clones (more than 2.5 times the theoretical mutant library diversity) were individually picked and screened by phage ELISA with the 6 different targets. 28 positives (clones binding one of the six targets) were identified. For validation, these 28 clones were re-assayed by phage ELISA, 8 times in parallel with the 6 different targets; 20 clones were thus confirmed as true positives. Finally, all 28 clones were sequenced.

TABLE 3

Sequence of the proteins found in the four different classes.

| Class I | Class II | Class III | Class IV |
|---------|----------|-----------|----------|
| Q R K   | (NTQH)N  | Q R T (2) | Unknown  |
| Q R R   | Q R N    | (RG) (ED) | sequence |
| H (KEQ) E | Q R A  | Q Q K (2) |          |
|         | Q S R    | Q N K     |          |
|         | Q T R (2)|           |          |
|         | Q Q R    |           |          |
|         | Q H K    |           |          |
|         | D S H    |           |          |
|         | Unknown  |           |          |
|         | sequence |           |          |

Only amino acids from position 44, 68 and 70 are indicated. Clones found twice are labeled with (2).

Four different patterns (ELISA results) could be observed. FIG. 10 features one representative example for each one. The first class (Class I) corresponds to a strong binding of C1234, C1221, C4334 and H4334. The wild-type protein (QRR) was recovered in this class, showing that Class I profile is the regular binding profile of the original scaffold. Two variants were also shown to display such binding (QRK and another yet not completely identified mutant).

Variants from the second class have lowered their affinity for all targets, but H4334, since no binding was observed with C1234, C1221 and C4334. Eight different proteins were found to belong to this class, plus a protein which sequence could not be determined. Among the sequence variants of Class II, five retain the Q44 amino acid from the wild-type sequence, and one of the two arginines in position 68 or 70. However, in one mutant (DSH), none of the amino acids from position 44, 68 and 70 has been retained. Class III (4 different proteins) has a more complex pattern, as it retains apparent binding for the C1221 and H4334 target. Finally, one protein (Class IV) retains only a slight binding for target C1221 as none of the other targets are bound anymore.

It is difficult to draw conclusions from Class IV, since the residual binding with C1221 is very low, and sequencing of the unique Class IV mutant has failed. However, comparison of Class II and III with the wild-type profile of Class I clearly shows that the binding specificity has been altered.

The conclusion is that even from small libraries such as Lib2 (complexity 1.7 $10^3$), variants with altered binding profiles can be isolated, as shown in FIG. 10. Therefore, strategies based on screening, starting with larger mutant libraries, should allow the identification of more dramatic alterations, for instance binding for targets that were not bound by the initial protein scaffold. In addition, this approach leads to the identification of many different proteins for each profile. An extensive study of this kind should also bring the basis of a better understanding of DNA/meganuclease interactions.

Example 5

Meganuclease-Induced Recombination of an Extrachromosomal Reporter In Toto Using I-Sce I Expressing Plasmid A-Optimization of the Reporter System
Experimental Procedures Vectors Construction The target vectors are based on a LagoZ expression vector driven by promoter of the human EF1-alpha gene. This promoter has been shown previously to have wide expression spectrum in vivo (Kim, D. W., Uetsuki, T., Kaziro, Y., Yamaguchi, N., Sugano, S, 1990, Gene, 91, 217-223). The promoter region includes splice donor and acceptor sites in the 5' untranslated region of the h-EF1-alpha gene-LagoZ is a CpG island depleted LacZ gene designed to abolish gene silencing in transgenic mice (Henry I, Forlani S, Vaillant S, Muschler J, Chøulika A, Nicolas J F, 1999, C R Acad Sci III. 322, 1061-70). To construct target vectors with different lengths of homology, the 3' fragment of the LagoZ gene was first deleted (about 2000 bp) and replaced by the I-Sce I cleavage site. The 3' fragments of different lengths were generated by digestion of the parental plasmid. These fragments contained different amounts of homology with the 5' fragment of the LagoZ gene. Finally these DNA fragments were individually cloned adjacent to the I-ScaI cleavage site, creating different target vectors with 0, 70, 220, 570, and 1200 by of homology, respectively.

Cell Culture

COS-7 and CHO-K1 cell lines from the American Type Culture Collection (ATCC) were cultured in DMEM or Ham's F12K medium respectively plus 10% fetal bovine serum. For I-Sce I induced Single Strand annealing (SSA) assays, cells were seeded in 12 well-plates at a $15.10^3$ cells per well one day prior transfection. Transient transfection was carried out the following day with 500 ng of DNA using the EFFEC-TENE transfection kit (Qiagen). Equimolar amounts of target plasmid and I-ScaI expression vector were used. The next day, medium was replaced and cells were incubated for an other 72 hours.

β-Galactosidase Activity

Cell monolayers were fixed in 0.5% glutaraldehyde in 100 mM PBS containing 1 mM $MgCl_2$ at 4° for 10 minutes. After one wash with detergent solution (100 mM PBS, 1 mM $MgCl_2$, 0.02% Nonidet p-40) cells were incubated at 37° in X-Gal stain solution (10 mM PBS, 1 mM $MgCl_2$, 150 mM NaCl, 33 mM $K_4Fe(CN)_6.3H_2O$, 33 mM $K_3Fe(CN)_6$, 0.1% X-Gal) until color development. Beta-galactosidase activity was also measured in cell extracts with o-nitrophenyl-β-D-galactopyrannoside (ONPG) as a substrate. Cell monolayers were washed once with PBS. Cells were then lysed with 10 mM Tris pH 7.5, 150 mM NaCl, 1% Triton X-100, protease inhibitors. After 30 minutes incubation on ice, cells lysates were centrifuged and β-galactosidase was assayed. Typically 30 μl of supernatant was combined with 270 μl of reaction buffer (10 mM PBS; pH 7.5, 1 mM $MgCl_2$, 0.3% β-mercaptoethanol) containing 800 μg/ml ONPG. The reaction was carried out at 37° and stopped with 0.5 ml of 1M $NaCO_3$. Optical density was measured at 415 nm. Beta-galactosidase activity is calculated as relative unit normalized for protein concentration and incubation time.

Results

When a DNA double-strand break (DSB) is introduced between two repeated sequences, it induces homologous recombination resulting in a deletion of the repeats, together with all the intervening sequences. The recombination pathway is often referred to as the single-strand annealing (SSA) pathway. A reporter system was designed to monitor meganuclease-induced SSA in animal models in toto. In order to optimize the reporter system, the correlation between meganuclease-induced SSA efficiency and repeat length was first examined. Different target vectors carrying a LagoZ gene containing duplications of various sizes were constructed (FIG. 11). The presence of the duplication and of the I-SceI cleavage site inactivates the gene. The repair of the LagoZ gene by SSA results in the loss of one repeat and of the cleavage site, and in the restoration of a functional LagoZ gene. LagoZ codes for the β-galactosidase enzyme which can be detected by colorimetry. Transient transfection with equimolar amounts of target vector and I-SceI expression vector or expression vector that doesn't express the meganuclease were carried out in CHO or COS-7 cells. The results obtained with the different constructs are presented in FIG. 12. I-SceI induced DSBs clearly stimulate the SSA repair mechanism. Furthermore, homology of 70 by was sufficient to achieve nearly maximum efficiencies of induced SSA, while the level of spontaneous recombination (without I-SceI induced DSB) was minimal. With duplication of 220 by maximum efficiency was achieved while no additional gains in SSA efficiency were observed with longer duplications. Similar results were obtained with COS-7 cells (data not shown). 70 and 220 by of homology gave the best ratio of activity vs background. Because β-galactosidase is assayed in cell lysates and one single cell can contain several copies of the target plasmid, it is impossible to evaluate the absolute SSA efficiency by this method. Therefore direct coloration of the cellular monolayer was performed 72 hours post-transfection (FIG. 13). Virtually no blue cells were detected in the absence of the meganuclease (FIG. 13A). In contrast, many β-galactosidase-positive cells are present when I-SceI is cotransfected with the target vector, demonstrating the stimulation of homologous recombination by meganuclease induced DSB. The efficiency of I-SceI induced SSA was calculated by counting the blue cells (cells where recombination has taken place) and comparing it with the number of transfected cells (cells that effectively received DNA). FIG. 13B shows that 50 to 60% of the cells undergo homologous recombination when I-SceI is present along with the target vector carrying 70 or 220 by duplications while spontaneous recombination represents less than 0.1% of the events. Thus, the construct with the 70 by and 220 by of homology as well as the transgene were selected for the animal study.

4B. Meganuclease-Induced Recombination of an Extrachromosomal Reporter In Toto

Experimental Procedures

Hydrodynamic-Based Transfection In Vivo

Transduction of the mouse liver cells was performed by hydrodynamic tail vein injections as previously described (Zhang, G., Budker, V., Wolff, A., 1999, Human Gene Therapy, 10, 1735-1737; Liu, F., Song, Y. K., Liu, D., 1999, Gene Therapy, 6, 1258-1266). This method allows efficient transduction and expression of exogenous genes in animals by administration of plasmid DNA by tail vein injection. Briefly, DNA is mixed in 1.5 to 2 ml of PBS, which represents 10% of the animal's weight. Tail vein injections are subsequently performed with a 26-gauge needle over a 5-10 sec period using sterile materials and working conditions. Using such a protocol, almost exclusively liver cells are transduced, thus the 1-SceI-mediated SSA event leading to the correction of the LagoZ gene was studied in the liver. The I-SceI expressing vector used is the pCLS 197 corresponding to the I-SceI-coding sequences (U.S. Pat. No. 5,474,896) under the control of the CMV promoter in a pUC backbone and is 5737 bp long.

OF1 mice weighing fifteen to twenty grams were obtained from Charles River Laboratories, France. A total of twenty micrograms of DNA, containing equal amounts of target vector and either an I-SceI expression or control vector, was injected into mouse tail veins. The target vector contains the LagoZ gene interrupted by an I-SceI cleavage site flanked by direct repeat sequences containing 70 by of homology. Control mice were injected with a mixture of the target vector and a plasmid that does not express I-SceI.

β-Galactosidase Activity

Three days after injection, mice were euthanized by cervical dislocation and X-Gal stainings of their livers were performed. Livers were dissected out of the animals in cold 1×PBS and the lobes were cut in pieces of about one fourth a centimeter in order to allow a better access of the X-Gal in the tissue. Then liver pieces were placed in fresh cold PBS 1× in a 12-well cell culture plate kept on ice, and fixed in 4% paraformaldehyde for 1 hour under agitation at 4° C. Samples were then washed 3 times at room temperature for 30 minutes with wash buffer (100 mM sodium phosphate pH=7.3, 2 mM $MgCl_2$, 0.01% sodium deoxycholate, 0.02% NP-40 by volume). In toto X-Gal staining was performed overnight at 37° C. in staining solution (5 mM potassium ferricyanide, 5 mM potassium ferrocyanide, 1 mg/ml X-gal, 20 mM Tris pH=7.3 in wash buffer). Finally samples were washed extensively with PBS and examined under microscope. Pictures were taken with a Nikon Coolpix camera under a Nikon SMZ 1500 binocular.

Results

Cellular study has shown that homology of 70 by is sufficient to achieve nearly maximal efficiencies of DSB induced SSA, while the level of spontaneous recombination (without I-SceI induced DSB) is minimal. Thus, in a first attempt to stimulate recombination in vivo, transient experiments were performed. A mixture of the target vector (30 µg) and either the I-SceI expression or control plasmid (10 µg) were introduced into the liver via a hydrodynamic tail vein injection method. FIG. 14 shows a magnified picture of liver collected 4nd stained 3 days after injection. Blue dots represent cells where a defective LagoZ gene, bearing an I-SceI site flanked by a 70 by duplication, was repaired. After meganuclease induced DSB, the SSA pathway results in the deletion of one repeat and reconstitution of a functional gene. Active β-galactosidase encoded by the LagoZ gene can then be detected by X-Gal stainings. Furthermore, no gene correction was detected in the absence of the meganuclease expression vector. These data represent the first evidence that meganuclease induced recombination can be stimulated in liver and that in toto repair of an extrachromosomal target can be achieved.

Example 6

Meganuclease-Induced Recombination of a Chromosomal Reporter In Toto Using I-Sce I Expressing Adenovirus In order to demonstrate meganuclease-induced genomic surgery of a chromosomal reporter in toto in different mice tissues, the repair of the lagoZ gene in toto was tested by transducing cells of several organs with an I-SceI-expressing adenovirus, <<Ad.I-SceI>>. Control transgenic littermates were infected with a non-I-SceI-expressing adenovirus, <<Ad.control>>. Adenovirus infections in transgenic mice were performed by intravenous (IV) injections. Repair of the lagoZ gene in toto in several tissues was then tested by two methods that detect β-galactosidase activity in toto: X-gal staining and FDG assays.

Experimental Procedures

Transgenic Mice

The transgene used for the generation of transgenic founders was a BglII/NotI fragment of 5919 by carrying the defective LagoZ gene, inactivated by a LagoZ duplication of 70 by or 220 by and the I-SceI cleavage site, under the control of the human elongation factor 1 alpha promoter (See FIG. 11).

Transgenic founder were generated by classical transgenesis, i.e. by microinjecting the linear and purified BglII/NotI fragment described above at 500 copies/picolitres into the male pronuclei of fertilized ova at the one-cell stage derived from the mating of B6D2F1 males and females purchased from Elevage Janvier. Microinjections were performed under a Nikon TE2000 microscope with Normarski DIC with eppendorf transferMan NK2 micromanipulators and eppendorf Femtojet 5247 micro-injector. After injections, ova were transferred to surrogate pseudopregnant B6CBAF1/J females (Elevage Janvier) for development and delivery. Transgenic mice generated by this procedure were identified by PCR and Southern Blot analysis on genomic DNA extracted from tail biopsies of F0 mice. The molecular characterization of the transgene integration was done by PCR and Southern Blot analysis.

Then the founder were mated to B6D2F1 mice in order to obtain hemizygote transgenic F1 animal. Expression of the transgene was tested by performing an RT-PCR experiment on RNAs extracted from a tail biopsie from a transgenic F1 animal using Qiagen RNeasy kit (cat No 74124). Hemizygote F1 mice were then mated to B6D2F1 mice in order to establish an F2 hemizygote transgenic strain.

Two independent strains were used bearing either 220 by or 70 by long lagoZ gene repeated sequences. These transgenic strains are referred as strain <<361>> and <<58A>>, respectively. The molecular characterization of the transgene integration showed that the integration is about 5 direct repeats of the BglII/NotI transgene in <<361>> and 2 inverted repeats plus 5 direct repeats in <<58A>>. Hemizygote mice were identified by tail biopsies, genomic DNA extraction and PCR analysis. <<361>> and <<58A>> hemizygote mice were then used for in toto I-SceI mediated-lagoZ gene repair and transgenic littermates were used as negative controls.

Adenovirus-Based Transduction In Toto

Recombinant type V adenovirus bearing the I-SceI meganuclease coding region under the control of a CMV promoter, <<Ad.I-SceI>> was provided by Q BIO gene company at $1.58 \cdot 10^{11}$ infectious units concentration scored by the $TCID_{50}$ method. The negative adenovirus control <<Ad.control>> was as well provided by Q BIO gene company at $3.76 \cdot 10^{11}$ infectious units concentration. Recombinant type V adenovirus infections were performed by intravenous (IV) injections in transgenic mice tail veins. Transgenic mice were weighed and anesthetized before infections by intraperitoneal injection of a mixture of Xylisin (100 mg/kg) and Ketamine (10 mg/kg). IV infections were performed with $10^{10}$ infectious units/animal in a volume of 400 µl. Infections were performed in 4 to 7 weeks-old transgenic mice. Adenovirus-infected mice and uninfected control littermates were bred in isolator until sacrificed for β-galactosidase assays.

β-Galactosidase Activity

Adenovirus-infected mice were sacrificed by $CO_2$ inhalation from 5 to 14 days-post-infections (dpi) and their organs were processed for β-galactosidase assays. About 10% of the liver (8 $mm^3$) was employed for protein extraction and the remaining 90% was used for β-galactosidase in toto X-gal assays (protocol described previously).

Fluorescent β-galactosidase assays were incubated at 37° C. in 96 well plate. The assays were performed in a total volume of 100 µl containing 30 µl of protein extract, 1 µM Fluorescein digalactoside (FDG, Sigma), 0.1% β-mercaptoethanol, 1 mM $MgCl_2$, and 100 mM Phosphate buffer, pH 7.0. The plates were scanned on the Fluoroskan Ascent (Labsystem) at 5-minutes intervals. The β-galactosidase activity is calculated as relative unit normalized for protein concentration and incubation time.

Results

Figure 15A:
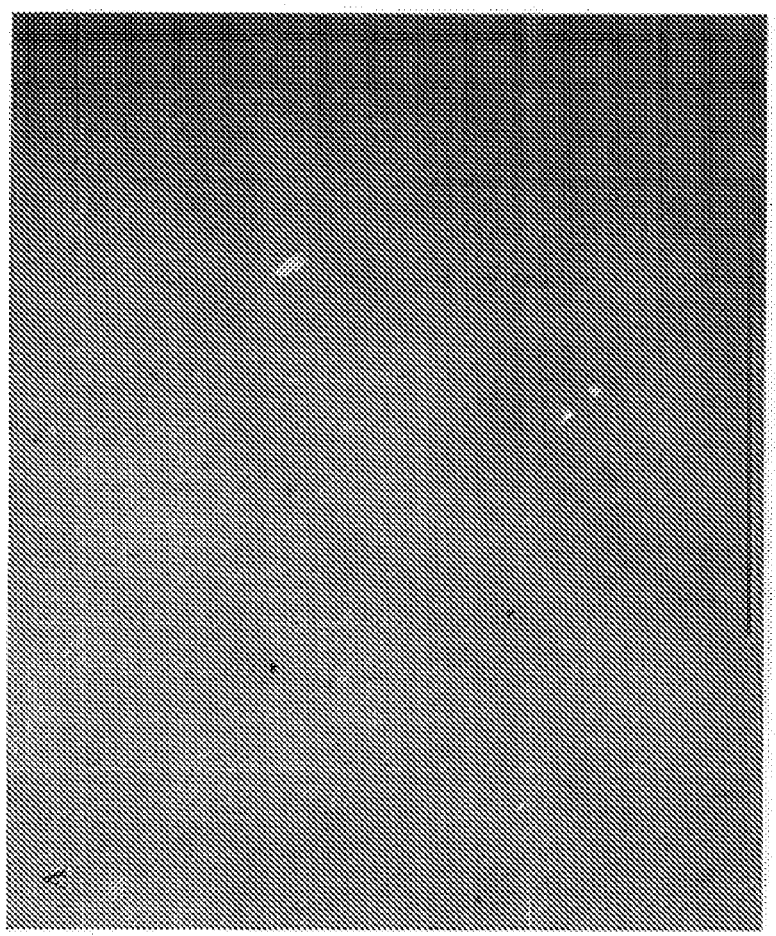
Figure 15B:
Figure 15C:
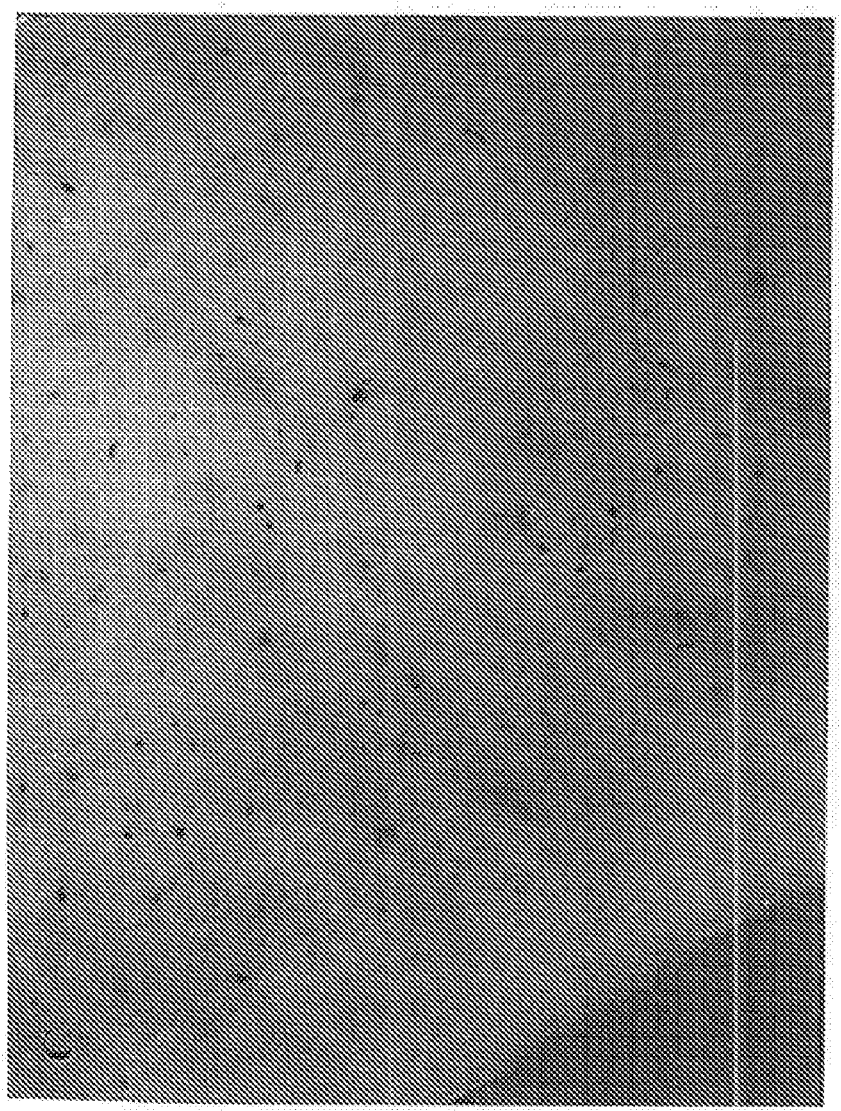

Two <<58A>> transgenic mice were IV-injected with $10^{10}$ infectious units of <<Ad.I-SceI>> adenovirus in order to target a DSB in-between the 70 by duplicated lagoZ sequences and induce the repair of the reporter gene. At various times post-injection the mice were sacrificed and several organs were dissected and analyzed by in toto X-gal assays. Blue staining was detected as dispersed cells over the entire liver of infected mouse euthanized at 5 dpi (FIG. 15A). No staining could be detected in the other organs tested, i.e. kidneys, spleen, heart and lungs. Two <<58A>> transgenic mouse littermates were used as controls, one IV-injected with $10^{10}$ infectious units of the control adenovirus <<Ad.control>> and the other uninfected. No β-galactosidase activity could be detected in the liver of either control (data not shown). Similar results were obtained with two <<361>> transgenic mice injected with $10^9$ and $10^{10}$ infectious units of the Ad.I-SceI adenovirus (FIGS. 15B and 15C respectively). These results were confirmed by measuring the β-galactosidase activity in liver extract (FIG. 16). A high activity was detected in liner of mice injected with Adenovirus expressing I-SceI (Ad.1Sce-I). In contrast, Non-injected mice (NI) shows only a residual background activity similar to the activity detected in mice injected with the control adenovirus (Ad.control).

The IV-injected mouse with $10^{10}$ infectious units of Ad.1-SceI adenovirus exhibited more stained liver cells and more β-galactosidase activity than the IV-injected mouse with $10^9$ infectious units of Ad.1-SceI adenovirus. These results suggest that I-SceI-induced recombination could be dose dependent and that a better yield of I-SceI induced recombination could be obtained by increasing the injected-adenovirus titer. Thus, the detection of I-SceI-induced genome surgery in other organs reported to be less sensitive to type V adenovirus infection should be feasible.

Taken together, these data strongly suggest that the reporter gene repair was induced by the activity of the I-SceI meganuclease. This result is the first evidence that I-SceI and more generally the meganucleases can be used in toto to induce efficient site-specific homologous recombination leading to the repair of a chromosomal gene. Thus, these results open applications in the field of gene therapy in mammals.

Example 7

Meganuclease-Induced Correction of a Mutated Human ApoAI Gene In Toto

Gene correction would be the safest Methodology of gene therapy. Indeed homologous recombination allows precise modification of chromosomal locus and has been widely used in cell culture. Unfortunately its efficiency is extremely low and cannot be envisioned, as it is, as a therapeutic tool. However this mechanism has been shown to be enhanced by double strand break (DSB) in the genomic target. So far, in vertebrates, the use of this technology has been limited to cell applications. This is the report for the first time of the use of DSB induced gene conversion in mammal in toto by direct injection of a mixture of meganuclease expression cassette and DNA repair matrix in the blood stream.

The system is based on the repair of a human Apo A-I transgene in mice in toto. The apolipoprotein A-I (APO A-I) is the main protein constituent of high density lipoprotein (HDL) and plays an important role in HDL metabolism. High density lipoproteins have a major cardio-protective role as the principal mediator of the reverse cholesterol transport. The Apo A-I gene is expressed in the liver and the protein is secreted in the blood. Moreover, Apo A-I deficiency in human leads to premature coronary heart disease. All together, these criteria make Apo A-I gene a good candidate for the study of meganuclease-induced gene correction.

Experimental Procedures

Transgene

The genomic sequence coding for the human Apo A-I gene was used to construct the transgene. Expression of the Apo A-I gene is driven by its own minimal promotor (328 bp) that has been shown to be sufficient to promote transgene expression in the liver (Walsh et al., J. Biol. Chem., 1989, 264, 6488-6494). Briefly, human Apo A-I gene was obtained by PCR on human liver genomic DNA (Clontech) and cloned in plasmide pUC19. The I-SceI site, containing two stop codons, was inserted by PCR at the beginning of exon 4 (FIG. 17). The resulting mutated gene (1-SceI-hApo A-I) encodes a truncated form of the native human APO A-I (80 residues vs. 267 amino-acids for the wild type APO A-I). All the constructs were sequenced and checked against the human Apo A-I gene sequence.

Generation of Transgenic Mice

The EcoRI/XbaI genomic DNA fragment carrying the mutated human Apo A-I gene was used for the generation of transgenic founders. Microinjections were done into fertilized oocytes from breeding of knock out males for the mouse apo a-I gene (WT KO mice) (The Jackson Laboratory, #002055) and B6SJLF1 females (Janvier). Transgenic founder mice (F0) were identified by PCR and Southern blot analysis on genomic DNA extracted from tail. F0 were then mated to WT KO mice in order to derive I-SceI-hApo A-I transgenic lines in knock out genetic background for the endogenous murine apo a-I gene. A total of seven independent transgenic lines were studied. The molecular characterization of transgene integration was done by Southern blot experiments.

Analysis of transgene expression in each transgenic line was performed by RT-PCR on total RNA extracted from the liver (Trizol Reagent, Invitrogen). In order to avoid cross reaction with the murine transcript, we used primers specific for the human transgenic I-SceI-hApo A-I cDNA (oligonucleotides E and F, FIG. 17). Actin primers were used as an internal control.

Hydrodynamic-Based Transduction In Toto

Transduction of transgenic mouse liver cells in toto was performed by hydrodynamic tail vein injection as previously described (Zhang et al., 1999, Human Gene Therapy, 10, 1735-1737). 10 to 20 g animals were injected with circular plasmid DNA in a volume of one tenth their weight in PBS in less than 10 seconds. We used a mixture of 20 or 50 µg of a plasmid coding for I-SceI under the control of the CMV promoter and the same amount of a plasmid carrying the DNA repair matrix (2 kbp or 1.5 kbp as depicted in FIG. 17). We also used 20 or 50 µg of a plasmid carrying the I-SceI expression cassette and the 2 kbp DNA repair matrix in the same vector.

Analysis of Gene Correction

The correction of the transgene in mice after injection of the I-SceI expression cassette and DNA repair matrix was analyzed by nested PCR on total liver RNA reverse transcribed using random hexamers. In order to detect the corrected gene, but not the uncorrected, we used primers sets that specifically amplified the repaired transgene. The specificity was achieved by using reverse oligonucleotides spanning the I-SceI site, forward being located outside the repair matrix (oligonucleotides G and H in the first PCR and E and I in the nested one, FIG. 17). Actin primers were used as an internal control.

Results

Seven transgenic lines carrying one or several copies of the I-SceI-hapo A-I transgene were used in these experiments. Table 4 summarized the molecular characterization and the expression of the transgene in each transgenic line.

TABLE 4

Molecular characterization of transgene integration and level of expression in the liver.

| lines | integration | copy number | expression |
|---|---|---|---|
| 14A | direct repeat | ~5-10 | ++ |
| 14B | single | 1 | + |
| 21 | direct repeat | ≦5 | + |
| 49 | direct repeat | ≦5 | +/− |
| 50 | single | 1 | +/− |
| 66 | single | 1 | + |
| 95 | single | 1 | + |

Because transgene expression was very low in lines 49 and 50 further analyses were done on the five other lines. In these experiments, mice were injected with either a mixture of I-SceI-expressing vector and DNA repair matrix or with a vector carrying both I-SceI-expressing cassette and the DNA repair matrix. The repair of the mutated human Apo A-I gene was monitored by RT-PCR on total liver RNA (FIG. 18) using primers specifically designed to pair only with the corrected human Apo A-I gene (FIG. 17). As a control, RT-PCR was performed on non-injected transgenic mice or injected with I-SceI expressing vector alone or the DNA repair matrix alone. No gene correction could be detected with these experimental conditions. Furthermore, wild type mice injected with either a mixture of I-SceI-expressing vector and DNA repair matrix or with a vector carrying both I-SceI-expressing cassette and the DNA repair matrix did not reveal any PCR-amplified DNA fragment. In contrast, PCR fragments were specifically visualized in transgenic mice where I-SceI-expressing cassette and the DNA repair matrix were injected (FIG. 18). The gene correction was detectable in all the transgenic lines tested containing one or several copies of the transgene (Table 5).

TABLE 5

RT-PCR analysis of transgene correction after I-SceI expression vector and repair matrix injections (IV) in mice. Mice where transgene was repaired/number of injected mice.

| | IV | | | | | | | |
|---|---|---|---|---|---|---|---|---|
| Line | I-SceI/ RM A | I-SceI/ RM B | I-SceI-RM A | Total | I-SceI alone | RM A alone | RM B alone | NI |
| 14A | 3/3 | 2/2 | 6/6 | 11/11 100% | 0/2 | 0/1 | 0/2 | 0/6 |
| 14B | 4/4 | 0/1 | 1/3 | 5/8 62% | | 0/1 | | 0/3 |
| 21 | 2/6 | 1/1 | 0/1 | 3/8 37% | 0/2 | 0/2 | 0/1 | 0/6 |
| 66 | 2/2 | | | 2/2 100% | | | | 0/1 |
| 95 | 0/3 | | 1/4 | 1/7 14% | | | | 0/4 |
| Total | | | | 22/36 61% | | | | |
| WT | 0/6 | 0/1 | 0/8 | | 0/4 | | | 0/1 |

NI: non-injected mice;
WT: wild type mice;
I-SceI: vector carrying the I-SceI expression cassette;
RM A: vector containing the 2 kbp repair matrix;
RM B: vector containing the 1.5 kbp repair matrix and
I-SceI-RM A: I-SceI expression cassette and the 2 kbp repair matrix in the same vector.

Detection of a corrected transgene occurs in 14 to 100% of injected mice depending on the transgenic lines. This heterogeneity probably reflects the high variability of the hydrodynamic tail vein injection methodology. Simple injection of one plasmid carrying the I-SceI-expressing cassette and the DNA repair matrix or injection of two vectors at the same time gave the same results. Finally, results were also similar with 20 or 50 µg of DNA injected. These results demonstrate that human Apo A-I gene correction was induced by I-SceI DSB repair mechanism.

These results give evidence that meganuclease-induced gene conversion can be used to perform in toto genome surgery, and that meganucleases can be used as drugs for such applications.

The invention claimed is:

1. A single chain homing endonuclease, comprising a first variant of I-CreI having the amino acid sequence of SEQ ID NO:23 and a second variant of I-CreI having the amino acid sequence of SEQ ID NO:23 in a single polypeptide, wherein said first variant of I-CreI contains the following substitutions: one to six substitutions in the sequence of amino acid residues 26 to 40 and two to three substitutions in the sequence of amino acid residues 44 to 77, wherein in said first variant of I-CreI there is a substitution at positions 33, 68 and 77, and independently, said second variant of I-CreI contains the following substitutions: four to six substitutions in the sequence of amino acid residues 26 to 40 and two to three substitutions in the sequence of amino acid residues 44 to 77, wherein in said second variant of I-CreI there is a substitution at positions 26, 30, 32, 38, 44, and 68, wherein the endonuclease binds and cleaves DNA.

2. The single chain homing endonuclease according to claim 1, wherein said second variant of I-CreI further contains a substitution at positions 40 and 77.

3. The single chain homing endonuclease according to claim 1, wherein said first variant of I-CreI has a substitution at least at positions 24, 33, 68, and 77, and in said second variant of I-CreI has a substitution at least at positions 26, 30, 32, 38, 40, 42, 44, 68, and 77.

4. The single chain homing endonuclease according to claim 1, wherein said first variant of I-CreI further contains a substitution at position 140.

5. The single chain homing endonuclease of claim 1 wherein the DNA sequence has at least 25% identity with the I-CreI recognition and cleavage site of SEQ ID NO:10.

6. The single chain homing endonuclease of claim 5 wherein the DNA sequence has at least 50% identity with the I-CreI recognition and cleavage site of SEQ ID NO:10.

7. The single chain homing endonuclease of claim 6 wherein the DNA sequence has at least 75% identity, with the I-CreI recognition and cleavage site of SEQ ID NO:10.

* * * * *

(12) EX PARTE REEXAMINATION CERTIFICATE (10406th)
United States Patent
Arnould et al.

(10) Number: US 7,842,489 C1
(45) Certificate Issued: Nov. 14, 2014

(54) USE OF MEGANUCLEASES FOR INDUCING HOMOLOGOUS RECOMBINATION EX VIVO AND IN TOTO IN VERTEBRATE SOMATIC TISSUES AND APPLICATION THEREOF

(75) Inventors: Sylvain Arnould, Paris (FR); Sylvia Bruneau, Paris (FR); Jean-Pierre Cabanios, Saint Leu la Foret (FR); Patrick Chames, Paris (FR); Andre Choulika, Paris (FR); Philippe Duchateau, Cerny (FR); Jean-Charles Epinat, Paris (FR); Agnes Gouble, Paris (FR); Emmanuel Lacroix, Paris (FR); Frederic Paques, Bourg la Reine (FR); Christophe Perez-Michaut, Paris (FR); Julianne Smith, Paris (FR); David Sourdive, Levallois-Perret (FR)

(73) Assignee: Cellectis, Romainville (FR)

Reexamination Request:
No. 90/011,806, Jul. 22, 2011

Reexamination Certificate for:
Patent No.: 7,842,489
Issued: Nov. 30, 2010
Appl. No.: 12/710,969
Filed: Feb. 23, 2010

Related U.S. Application Data

(63) Continuation of application No. 10/543,557, filed as application No. PCT/IB2004/000848 on Jan. 28, 2004, now abandoned.

(60) Provisional application No. 60/491,535, filed on Aug. 1, 2003, provisional application No. 60/442,911, filed on Jan. 28, 2003.

(51) Int. Cl.
*C12N 9/22* (2006.01)
*C12N 15/55* (2006.01)
*A01K 67/027* (2006.01)
*C12N 15/85* (2006.01)
*C12N 15/10* (2006.01)
*A61K 38/17* (2006.01)
*C12N 15/90* (2006.01)
*A61K 48/00* (2006.01)

(52) U.S. Cl.
CPC ........ *A01K 67/0275* (2013.01); *C12N 15/8509* (2013.01); *C12N 15/1058* (2013.01); *A61K 38/1709* (2013.01); *C12N 9/22* (2013.01); *C12N 15/90* (2013.01); *A61K 48/0058* (2013.01); *A01K 67/0278* (2013.01)
USPC .......... 435/199; 435/183; 435/196; 435/69.7; 530/350

(58) Field of Classification Search
None
See application file for complete search history.

(56) References Cited

To view the complete listing of prior art documents cited during the proceeding for Reexamination Control Number 90/011,806, please refer to the USPTO's public Patent Application Information Retrieval (PAIR) system under the Display References tab.

*Primary Examiner* — Sharon Turner

(57) ABSTRACT

A single chain homing endonuclease, comprising a first variant of 1-Cre1 having the amino acid sequence of accession number pdb 1g9y (SEQ 1D NO: 23 is residues 1-153 of pdb 1g9y) and a second variant of 1-Cre1 variant having the amino acid sequence of accession number pdb 1g9y (SEQ 1D NO: 23 is residues 1-153 of pdb 1g9y) in a single polypeptide.

**Attention is directed to the decision of *Precision v. Cellectis*, 5:11cv91; *Precision v. Cellectis*, 5:10cv550; *Cellectis v. Precision*, 1:10cv1033 relating to this patent. This reexamination may not have resolved all questions raised by these decisions. See 37 CFR 1.552(c) for *ex parte* reexamination and 37 CFR 1.906(c) for *inter partes* reexamination.**

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-7 are cancelled.

\* \* \* \* \*

SEQUENCE LISTING

<160> NUMBER OF SEQ ID NOS: 23

<210> SEQ ID NO 1
<211> LENGTH: 264

<212> TYPE: PRT
<213> ORGANISM: Artificial Sequence
<220> FEATURE:
<223> OTHER INFORMATION: Synthetic protein

<400> SEQUENCE: 1

Met Ala Asn Thr Lys Tyr Asn Lys Glu Phe Leu Leu Tyr Leu Ala Gly
1               5                   10                  15
Phe Val Asp Gly Asp Gly Ser Ile Ile Ala Gln Ile Lys Pro Asn Gln
            20                  25                  30
Ser Tyr Lys Phe Lys His Gln Leu Ser Leu Thr Phe Gln Val Thr Gln
        35                  40                  45
Lys Thr Gln Arg Arg Trp Phe Leu Asp Lys Leu Val Asp Glu Ile Gly
    50                  55                  60
Val Gly Tyr Val Arg Asp Arg Gly Ser Val Ser Asp Tyr Ile Leu Ser
65                  70                  75                  80
Glu Ile Lys Pro Leu His Asn Phe Leu Thr Gln Leu Gln Ala Met Leu
                85                  90                  95
Glu Arg Ile Arg Leu Phe Asn Met Arg Glu Phe Leu Leu Tyr Leu Ala
            100                 105                 110
Gly Phe Val Asp Gly Asp Gly Ser Ile Ile Ala Gln Ile Lys Pro Asn
        115                 120                 125
Gln Ser Tyr Lys Phe Lys His Gln Leu Ser Leu Thr Phe Gln Val Thr
    130                 135                 140
Gln Lys Thr Gln Arg Arg Trp Phe Leu Asp Lys Leu Val Asp Glu Ile
145                 150                 155                 160
Gly Val Gly Tyr Val Arg Asp Arg Gly Ser Val Ser Asp Tyr Ile Leu
                165                 170                 175
Ser Glu Ile Lys Pro Leu His Asn Phe Leu Thr Gln Leu Gln Pro Phe
            180                 185                 190
Leu Lys Leu Lys Gln Lys Gln Ala Asn Leu Val Leu Lys Ile Ile Glu
        195                 200                 205
Gln Leu Pro Ser Ala Lys Glu Ser Pro Asp Lys Phe Leu Glu Val Cys
    210                 215                 220
Thr Trp Val Asp Gln Ile Ala Ala Leu Asn Asp Ser Lys Thr Arg Lys
225                 230                 235                 240
Thr Thr Ser Glu Thr Val Arg Ala Val Leu Asp Ser Leu Ser Glu Lys
                245                 250                 255
Lys Lys Ser Ser Pro Ala Ala Asp
            260

<210> SEQ ID NO 2
<211> LENGTH: 795
<212> TYPE: DNA
<213> ORGANISM: Artificial Sequence
<220> FEATURE:
<223> OTHER INFORMATION: Synthetic DNA

<400> SEQUENCE: 2
atggccaaca ctaagtacaa taaagaattt ctcctgtatc tggcaggttt cgtcgacggc      60
gatggctcca ttatcgcaca gatcaagccg aatcagagct acaagtttaa acaccaactg     120
tctctcactt tccaggttac ccagaaaact caacgtcgcg gttcctgga taagctggta      180 gatgagatcg gtgtgggcta tgtacgcgac cgtggctctg tgagcgacta tatcctgtct     240
gagattaaac cactgcataa ttttctgacc cagctgcagg ctatgctgga gcgtatccgt     300
ctgttcaaca tgcgtgagtt cctgctgtac ctggccggct ttgtggacgg tgacggtagc     360

```
atcatcgctc agattaaacc aaaccagtct tataaattca agcatcagct gtccctgacc    420
tttcaggtga ctcaaaagac ccagcgccgt tggtttctgg acaaactggt ggatgaaatt    480
ggcgttggtt acgtacgtga tcgcggtagc gtttccgatt acattctgag cgaaatcaag    540
ccgctgcaca acttcctgac tcaactgcaa ccgtttctga actgaaaaca gaaacaggca    600
aacctggttc tgaaaattat cgaacagctg ccgtctgcaa agaatcccc ggacaaattc    660 ctggaagttt gtacctgggt ggatcagatt gcagctctga cgattctaa gacgcgtaaa    720 accacttctg aaaccgttcg tgctgtgctg acagcctga gcgagaagaa gaaatcctcc    780
ccggcggccg actag                                                    795
```

```
<210> SEQ ID NO 3
<211> LENGTH: 492
<212> TYPE: DNA
<213> ORGANISM: Artificial Sequence
<220> FEATURE:
<223> OTHER INFORMATION: Synthetic DNA

<400> SEQUENCE: 3
atggccaata ccaaatataa caaagagttc ctgctgtacc tggccggctt tgtggacggt     60
gacggtagca tcatcgctca gattaaacca aaccagtctt ataaattcaa gcatcagctg    120
tccctgacct ttcaggtgac tcaaaagacc cagcgccgtt ggtttctgga caaactggtg    180
gatgaaattg gcgttggtta cgtacgtgat cgcggtagcg tttccgatta cattctgagc    240
gaaatcaagc cgctgcacaa cttcctgact caactgcaac cgtttctgaa actgaaacag    300
aaacaggcaa acctggttct gaaaattatc gaacagctgc cgtctgcaaa gaatccccg    360 gacaaattcc tggaagtttg tacctgggtg gatcagattg cagctctgaa cgattctaag    420
acgcgtaaaa ccacttctga aaccgttcgt gctgtgctgg acagcctgag cgagaagaag    480
aaatcctccc cg                                                      492
```

```
<210> SEQ ID NO 4
<211> LENGTH: 492
<212> TYPE: DNA
<213> ORGANISM: Artificial Sequence
<220> FEATURE:
<223> OTHER INFORMATION: Synthetic DNA

<400> SEQUENCE: 4
atggccaaca ctaagtacaa taaagaattt ctcctgtatc tggcaggttt cgtcgacggc     60
gatggctcca ttatcgcaca gatcaagccg aatcagagct acaagtttaa acaccaactg    120
tctctcactt tccaggttac ccagaaaact caacgtcgct ggttcctgga taagctggta    180
gatgagatcg gtgtgggcta tgtacgcgac cgtggctctg tgagcgacta tatcctgtct    240
gagattaaac cactgcataa ttttctgacc cagctgcagc cgttcctcaa gctgaagcaa    300
aaacaggcca atctcgtgct gaagatcatt gagcaactgc catccgccaa agagtctccg    360
gataaatttc tggaggtctg cacttgggtt gaccaaatcg ctgcactcaa cgactccaaa    420
acccgcaaga cgaccagcga gactgtacgc gcagttctgg attctctctc cgaaaaaaag    480
aagtctagcc cg                                                      492
```

```
<210> SEQ ID NO 5
<211> LENGTH: 492
<212> TYPE: DNA
<213> ORGANISM: Artificial Sequence
<220> FEATURE:
```

<223> OTHER INFORMATION: Synthetic DNA

<400> SEQUENCE: 5

| atggccaata ccaaatataa caaagagttc ctgctgtacc tggccggctt tgtggacggt | 60 |
|---|---|
| gacggtagca tcatcgctca gattaaacca aaccagtctt ataagtttaa acatcagcta | 120 |
| agcttgacct ttcaggtgac tcaaaagacc cagcgccgtt ggtttctgga caaactagtg | 180 |
| gatgaaattg gcgttggtta cgtacgtgat cgcggatccg tttccaacta catcttaagc | 240 |
| gaaatcaagc cgctgcacaa cttcctgact caactgcagc cgtttctgaa actgaaacag | 300 |
| aaacaggcaa acctggttct gaaaattatc gaacagctgc cgtctgcaaa agaatccccg | 360 |
| gacaaattcc tggaagtttg tacctgggtg atcagattg cagctctgaa cgattctaag | 420 |
| acgcgtaaaa ccacttctga aaccgttcgt gctgtgctgg acagcctgag cgagaagaag | 480 |
| aaatcctccc cg | 492 |

<210> SEQ ID NO 6
<211> LENGTH: 42
<212> TYPE: DNA
<213> ORGANISM: Artificial Sequence
<220> FEATURE:
<223> OTHER INFORMATION: Synthetic DNA

<400> SEQUENCE: 6

| acgacggcca gtgaattcac catggccaat accaaatata ac | 42 |
|---|---|

<210> SEQ ID NO 7
<211> LENGTH: 75
<212> TYPE: DNA
<213> ORGANISM: Artificial Sequence
<220> FEATURE:
<223> OTHER INFORMATION: Synthetic DNA

<400> SEQUENCE: 7

| cacctgaaag gtcaagctta gmbbatgttt aaacttmbba gactgmbbtg gmbbaatmbb | 60 |
|---|---|
| agcgatgatg ctacc | 75 |

<210> SEQ ID NO 8
<211> LENGTH: 49
<212> TYPE: DNA
<213> ORGANISM: Artificial Sequence
<220> FEATURE:
<223> OTHER INFORMATION: Synthetic DNA

<400> SEQUENCE: 8

| gtttaaacat cagctaagct tgacctttvv kgtgactcaa aagacccag | 49 |
|---|---|

<210> SEQ ID NO 9
<211> LENGTH: 45
<212> TYPE: DNA
<213> ORGANISM: Artificial Sequence
<220> FEATURE:
<223> OTHER INFORMATION: Synthetic DNA

<400> SEQUENCE: 9

| gatgtagttg gaaacggatc cmbbatcmbb tacgtaacca acgcc | 45 |
|---|---|

<210> SEQ ID NO 10
<211> LENGTH: 24
<212> TYPE: DNA
<213> ORGANISM: Artificial Sequence
<220> FEATURE:
<223> OTHER INFORMATION: Synthetic DNA

<400> SEQUENCE: 10
tcaaaacgtc gtgagacagt ttgg                                          24

<210> SEQ ID NO 11
<211> LENGTH: 24
<212> TYPE: DNA
<213> ORGANISM: Artificial Sequence
<220> FEATURE:
<223> OTHER INFORMATION: Synthetic DNA

<400> SEQUENCE: 11
tcaaaacgtc gtacgacgtt ttga                                          24

<210> SEQ ID NO 12
<211> LENGTH: 24
<212> TYPE: DNA
<213> ORGANISM: Artificial Sequence
<220> FEATURE:
<223> OTHER INFORMATION: Synthetic DNA

<400> SEQUENCE: 12
ccaaactgtc tcgagacagt ttgg                                          24

<210> SEQ ID NO 13
<211> LENGTH: 24
<212> TYPE: DNA
<213> ORGANISM: Artificial Sequence
<220> FEATURE:
<223> OTHER INFORMATION: Synthetic DNA

<400> SEQUENCE: 13
ggaagaagcc ttaagacatt ttga                                          24

<210> SEQ ID NO 14
<211> LENGTH: 24
<212> TYPE: DNA
<213> ORGANISM: Artificial Sequence
<220> FEATURE:
<223> OTHER INFORMATION: Synthetic DNA

<400> SEQUENCE: 14
ggaagaagcc ttaaggcttc ttcc                                          24

<210> SEQ ID NO 15
<211> LENGTH: 24
<212> TYPE: DNA
<213> ORGANISM: Artificial Sequence
<220> FEATURE:
<223> OTHER INFORMATION: Synthetic DNA

<400> SEQUENCE: 15
tcaaaatgtc ttaagacatt ttga                                          24

<210> SEQ ID NO 16
<211> LENGTH: 20
<212> TYPE: DNA
<213> ORGANISM: Artificial Sequence
<220> FEATURE:
<223> OTHER INFORMATION: Synthetic DNA

<400> SEQUENCE: 16
tgcggtgctg accttggccg                                               20

<210> SEQ ID NO 17

```
<211> LENGTH: 20
<212> TYPE: DNA
<213> ORGANISM: Artificial Sequence
<220> FEATURE:
<223> OTHER INFORMATION: Synthetic DNA

<400> SEQUENCE: 17
ctgttatccc tagcggatcc                                              20

<210> SEQ ID NO 18
<211> LENGTH: 20
<212> TYPE: DNA
<213> ORGANISM: Artificial Sequence
<220> FEATURE:
<223> OTHER INFORMATION: Synthetic DNA

<400> SEQUENCE: 18
gagaaggagg tcccccacgg                                              20

<210> SEQ ID NO 19
<211> LENGTH: 22
<212> TYPE: DNA
<213> ORGANISM: Artificial Sequence
<220> FEATURE:
<223> OTHER INFORMATION: Synthetic DNA

<400> SEQUENCE: 19
cgcagcttgc tgaaggtgga gg                                           22

<210> SEQ ID NO 20
<211> LENGTH: 22
<212> TYPE: DNA
<213> ORGANISM: Artificial Sequence
<220> FEATURE:
<223> OTHER INFORMATION: Synthetic DNA

<400> SEQUENCE: 20
cttgctgaag gtggaggtca cg                                           22

<210> SEQ ID NO 21
<211> LENGTH: 22
<212> TYPE: DNA
<213> ORGANISM: Artificial Sequence
<220> FEATURE:
<223> OTHER INFORMATION: Synthetic DNA

<400> SEQUENCE: 21
gacggccaag tcatcactat tg                                           22

<210> SEQ ID NO 22
<211> LENGTH: 22
<212> TYPE: DNA
<213> ORGANISM: Artificial Sequence
<220> FEATURE:
<223> OTHER INFORMATION: Synthetic DNA

<400> SEQUENCE: 22
ccacaggatt ccatacccaa ga                                           22

<210> SEQ ID NO 23
<211> LENGTH: 153
<212> TYPE: PRT
<213> ORGANISM: Artificial Sequence
<220> FEATURE:
<223> OTHER INFORMATION: Synthetic protein

<400> SEQUENCE: 23
```

-continued

```
Met Asn Thr Lys Tyr Asn Lys Glu Phe Leu Leu Tyr Leu Ala Gly Phe
1               5                   10                  15

Val Asp Gly Asp Gly Ser Ile Ile Ala Gln Ile Lys Pro Asn Gln Ser
            20                  25                  30

Tyr Lys Phe Lys His Gln Leu Ser Leu Thr Phe Gln Val Thr Gln Lys
        35                  40                  45

Thr Gln Arg Arg Trp Phe Leu Asp Lys Leu Val Asp Glu Ile Gly Val
    50                  55                  60

Gly Tyr Val Arg Asp Arg Gly Ser Val Ser Asp Tyr Ile Leu Ser Glu
65              70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp
145             150
```